(12) United States Patent
Sinha et al.

(10) Patent No.: US 9,238,795 B2
(45) Date of Patent: Jan. 19, 2016

(54) POPULATIONS OF SMOOTH MUSCLE CELLS OF SPECIFIC EMBRYONIC LINEAGES

(75) Inventors: Sanjay Sinha, Cambridge (GB); Roger Pedersen, Cambridge (GB); Andreia Bernardo, Cambridge (GB); Christine Cheung, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 14/126,212

(22) PCT Filed: Jun. 13, 2012

(86) PCT No.: PCT/GB2012/051334
§ 371 (c)(1),
(2), (4) Date: Dec. 13, 2013

(87) PCT Pub. No.: WO2012/172328
PCT Pub. Date: Dec. 20, 2012

(65) Prior Publication Data
US 2014/0127173 A1 May 8, 2014

(30) Foreign Application Priority Data

Jun. 13, 2011 (GB) .................................. 1109882.9

(51) Int. Cl.
| | | |
|---|---|---|
| C12N 5/077 | (2010.01) | |
| C12N 5/071 | (2010.01) | |
| C12N 5/073 | (2010.01) | |
| C12N 5/0775 | (2010.01) | |

(52) U.S. Cl.
CPC ............ *C12N 5/0661* (2013.01); *C12N 5/0662* (2013.01); *C12N 5/0691* (2013.01); *C12N 2501/115* (2013.01); *C12N 2501/155* (2013.01); *C12N 2506/03* (2013.01)

(58) Field of Classification Search
CPC ...................... C12N 2501/115; C12N 2501/16; C12N 2501/155; C12N 5/0606; C12N 2501/119; C12N 5/0661; C12N 5/0623; C12N 5/0691
See application file for complete search history.

(56) References Cited

U.S. PATENT DOCUMENTS

| | | | | |
|---|---|---|---|---|
| 8,323,971 | B2 * | 12/2012 | Pedersen et al. ............... | 435/377 |
| 2005/0112106 | A1 | 5/2005 | Gerecht-Nir et al. | |
| 2010/0184212 | A1 * | 7/2010 | Stice et al. ..................... | 435/366 |
| 2011/0002897 | A1 * | 1/2011 | Snyder et al. ................. | 424/93.7 |
| 2011/0027886 | A1 * | 2/2011 | Han et al. ...................... | 435/377 |
| 2012/0322151 | A1 * | 12/2012 | Gerecht et al. ................ | 435/366 |
| 2014/0030236 | A1 * | 1/2014 | Wanjare et al. ............... | 424/93.7 |
| 2014/0045265 | A1 * | 2/2014 | Belmonte et al. ............. | 435/377 |

FOREIGN PATENT DOCUMENTS

| | | |
|---|---|---|
| WO | WO-2008/056166 A2 | 5/2008 |
| WO | WO-2008/056173 A2 | 5/2008 |
| WO | WO-2009/120762 A2 | 10/2009 |

OTHER PUBLICATIONS

Zhang et al., Blood, 2008 111:1933-1941.*
Willems and Leyns, Differentiation (2008) 76:745-759.*
Shiraki et al., Biochemical and Biophysical Research Communications 381 (2009) 694-699.*
Aihara, Yuko, et al. "Induction of neural crest cells from mouse embryonic stem cells in a serum-free monolayer culture," International Journal of Developmental Biology; 54(8-9): 1287-1294 (2010).
Kane, Nicole M., et al. "Pluripotent stem cell differentiation into vascular cells: A novel technology with promises for vascular re(generation)," Pharmacology & Therapeutics 129(1): 29-49 (Jan. 1, 2011).
Majesky, Mark W. "Developmental basis of vascular smooth muscle diversity," Arteriosclerosis, Thrombosis, and Vascular Biology; 27(6): 1248-1258 (Jun. 2007).
Ross, Jeffrey J., et al. "Cytokine-induced differentiation of multipotent adult progenitor cells into functional smooth muscle cells," Journal of Clinical Investigation; 116(12): 3139-3149 (Dec. 2006).
Smith, Joseph R., et al. "Inhibition of Activiin/Nodal signaling promotes specification of human embryonic stem cells into neuroectoderm," Developmental Biology; 313(1): 107-117 (2007).
Vallier, Ludovic, et al. "Early Cell Fate Decisions of Human Embryonic Stem Cells and Mouse Epiblast Stem Cells Are Controlled by the Same Signalling Pathways," PLoS One; 4(6): e6082(pp. 1-13) (Jun. 2009).
Vazão, Helena, et al. "Towards the Maturation and Characterization of Smooth Muscle Cells Derived from Human Embryonic Stem Cells," PLoS One; 6(3): e17771 (pp. 1-14) (Mar. 1, 2011).
Vo, Elaine, et al. "Smooth-Muscle-Like Cells Derived from Human Embryonic Stem Cells Support and Augment Cord-Like Structures in Vitro," Stem Cell Reviews and Reports 6(2): 237-247 (Jun. 2010).
European Search Report for GB1109882.9 mailed Feb. 13, 2012.
International Search Report for PCT/GB2012/051334 mailed Oct. 15, 2012.

* cited by examiner

*Primary Examiner* — Daniel C Gamett
(74) *Attorney, Agent, or Firm* — Foley Hoag LLP

(57) ABSTRACT

This invention relates to the production of populations of Smooth Muscle Cells (SMCs) of specific embryonic lineages, such as neuroectodermal and mesodermal SMCs. Pluripotent stem cells are cultured in one or more lineage induction media to produce progenitor cells of a defined embryonic lineage, which are then cultured in an SMC induction medium to produce a population of SMCs of the embryonic lineage. Populations of SMCs of defined lineages may be useful, for example, in accurately modelling vascular disease.

19 Claims, 40 Drawing Sheets

POPULATIONS OF SMOOTH MUSCLE CELLS OF SPECIFIC EMBRYONIC LINEAGES

This application is a 371 national stage application of PCT/GB2012/051334, filed Jun. 13, 2012, which claims priority to GB 1109882.9, filed Jun. 13, 2011. The entire contents of each of these applications are hereby incorporated by reference.

This invention relates to the production of populations of Vascular Smooth Muscle Cells (V-SMCs) from specific embryonic lineages.

Smooth Muscle Cells (SMCs) make up the medial layer of blood vessels and are essential for the development of a mature and stable vasculature. They stabilise nascent vessels, mediate haemodynamics and are responsible for synthesis of extracellular matrix which provides essential vascular elasticity and durability. Moreover, they have the ability to change phenotype from the usual contractile state in healthy vessels to a reparative synthetic phenotype in response to vessel injury. Interestingly, lineage tracking studies have shown that vascular SMCs in different vessels and vascular territories have distinct embryonic origins. For example, the aortic root is derived from secondary heart field, while the ascending aorta and cerebral vessels are neural crest derived. The descending thoracic aorta originates from paraxial/somitic mesoderm while the descending abdominal aorta is derived from splanchnic/lateral mesoderm. Coronary arteries originate from the pro-epicardial organ which is of mesodermal origin. In summary, different SMC populations arise from neural crest (which in turn originates from neuroectoderm) or various types of mesoderm. These different SMC populations display distinct lineage-specific biological properties and responses to cytokines, which may influence their responses to physiological and/or pathological stimuli.

Deriving SMCs from human ESCs and iPS cells, collectively known as human pluripotent stem cells (hPSCs), has great potential for disease modelling and regenerative medicine. However, current models for deriving SMCs from human PSCs are poor and do not recapitulate the lineage restricted origins of SMCs. Several in vitro models have been described in which SMCs may be generated with high efficiency from hESCs. Huang et al (2006) treated a monolayer of hESCs with all trans-retinoic acid (Huang et al 2006) while other groups used EB-derived progenitor cells treated with a combination of growth factors and extracellular matrix coatings (Xie et al 2007, Ferreira et al. 2007) or hESC monolayers treated with growth factor combinations (Vo et al 2010). Recently, Vazao et al (2011) investigated the factors required to maximise SMC differentiation from hESCs and characterised the resulting cell phenotype in detail.

SUMMARY OF INVENTION

The present inventors have developed methods for producing populations of Smooth Muscle Cells (SMCs) of specific embryonic lineages, including neuroectodermal and mesodermal SMCs.

An aspect of the invention provides a method for producing a population of embryonic-lineage specific smooth muscle cells (SMCs) comprising;
(i) providing a population of pluripotent stem cells,
(ii) culturing the population of pluripotent stem cells in one or more lineage induction media to produce a population of progenitor cells of a defined embryonic lineage, and;
(iii) culturing the population of progenitor cells in an SMC induction medium to produce a population of SMCs of the embryonic lineage.

Step ii) of the method may comprise;
(a) culturing the population of pluripotent stem cells in a first lineage induction medium to produce a population of early progenitor cells,
(b) culturing the population of early progenitor cells in second lineage induction medium to produce a population of progenitor cells of a defined embryonic lineage and optionally,
(c) culturing the population of progenitor cells in one or more additional lineage induction media induction medium to produce a population of late progenitor cells of a defined lineage.

Another aspect of the invention provides a method for producing a population of mesodermal smooth muscle cells (SMCs) may comprise;
(i) providing a population of pluripotent stem cells,
(ii) culturing the population of pluripotent stem cells in early mesoderm induction medium,
wherein the early mesoderm induction medium is a chemically defined medium (CDM) which has fibroblast growth factor activity, stimulates SMAD1, SMAD5 and SMAD9 mediated signalling pathways and inhibits phosphatidylinositol 3-kinase (PI3K) activity,
(iii) either a) further culturing the population in a lateral mesoderm induction medium to produce a population of lateral mesodermal progenitor cells,
wherein the lateral mesoderm induction medium is a chemically defined medium (CDM) which has fibroblast growth factor activity and stimulates SMAD1, SMAD5 and SMAD9 mediated signalling pathways, or;
b) further culturing the population in a paraxial mesoderm induction medium to produce a population of paraxial mesodermal progenitor cells,
wherein the paraxial mesoderm induction medium is a chemically defined medium (CDM) which has fibroblast growth factor activity and inhibits phosphatidylinositol 3-kinase (PI3K) activity; and
(iv) culturing the population of lateral or paraxial mesodermal progenitor cells in an SMC induction medium to produce a population of lateral or paraxial mesodermal SMCs,
wherein the SMC induction medium is a chemically defined medium (CDM) which has platelet derived growth factor (PDGF) activity and activates Smad2 and/or Smad3 mediated signalling pathways.

Another aspect of the invention provides a method for producing a population of neuroectodermal smooth muscle cells (SMCs) comprising;
(i) providing a population of pluripotent stem cells,
(ii) culturing the population of pluripotent stem cells in a neuroectoderm induction medium to produce a population of neuroectodermal progenitor cells,
wherein the neuroectoderm induction medium is a chemically defined medium (CDM) which has fibroblast growth factor (FGF) activity and activin inhibition activity, and;
(iii) further culturing the population in an SMC induction medium to produce a population of neuroectodermal SMCs,
wherein the SMC induction medium is a chemically defined medium (CDM) which has platelet derived growth (PDGF) factor activity and activates Smad2 and/or Smad3 mediated signalling pathways.

Other aspects of the invention relate to the production of two of more different populations of neuroectodermal and mesodermal smooth muscle cells (SMCs) from a clonal population of pluripotent cells, as described above.

BRIEF DESCRIPTION OF FIGURES

FIGS. 1 to 6 show the induction and characterisation of mesoderm subtypes

FIG. 2 shows QRTPCR analysis of markers of early mesoderm subtypes in differentiating hESCs and the effects of BMP4 (B) concentration and presence of activin (A). High BMP4 concentration favours lateral plate mesoderm (KDR) while its absence favours paraxial mesoderm development (Meox1). Activin was not required for mesoderm patterning. hESCs were grown according to the protocol depicted in FIG. 1Ai and harvested at day 5.

FIG. 3 shows the results of QRTPCR analysis of lateral plate and paraxial mesoderm markers LMO2, PECAM1, NKX2.5, ISL1, MEOX1, TBX6, TCF15 and PAX1 in hESCs differentiated for 36 h in FLyB and then 3.5 additional days in FGF2 (F) or FGF2+BMP4 (FB50, where BMP4 is 50 ng/ml), with or without LY294002 (Ly). Ly was found to promote paraxial mesoderm patterning but had no effect or inhibited lateral mesoderm.

FIG. 4 shows a time-course QPCR to validate the conditions established for mesoderm specification. After a common 36-h treatment of FLyB, lateral and paraxial mesoderms were specified using FB50 and Fly, respectively.

FIG. 5 shows flow cytometric analysis of the percentage of KDR+ and TCF15+ gene-expressing cells for hESCs differentiated for 36 hours in FLyB and then in the conditions indicated for up to day 3 (D3) or day 5 (D5).

FIGS. 20 to 28 show validation of the origin-specific characteristics of hPSC-derived SMC subtypes using MKL2 knockdown and cytokine treatments.

FIG. 20 shows qRT-PCP analysis which verifies 60-65% knockdown of the MKL2 expression levels in the intermediate populations (NE, LM and PM) by MKL2 siRNA.

FIG. 21 shows western blot analysis confirming the effects of MKL2 siRNA knockdown on the protein levels compared to scrambled siRNA controls.

FIG. 22 shows SMC gene expression levels after SMC differentiation of the siRNA-treated intermediate populations, as determined, by qRT-PCR.

FIG. 23 shows the percentage of MYH11+ACTA2+ SMCs obtained from the siRNA-treated intermediate populations, as determined by flow cytometry FIG. 24 shows the proliferation responses of the SMC subtypes as monitored by MTT assay every 24 h over 3 d of treatment with the cytokines indicated.

FIG. 25 shows cell cycle analysis of the SMC subtypes after 24 h of cytokine treatments (FIG. 25A). The percentage of cells in different phases of the cell cycle was quantified by the areas under the peaks (FIG. 25B). Black dashed lines divide the growth arrested cells in G0-G1 from the proliferating cells in S and G2-M of the control groups. PI, propidium iodide.

FIG. 26 shows gene expression levels in control and TGF-β1-treated SMCs as determined by qRT-PCR after 10 h of treatment.

FIG. 27 shows western blot analysis was done to confirm the distinct secretory responses exhibited by TGF-β1-treated SMC subtypes.

FIGS. 28 to 30 show that HPSC-derived SMC subtypes predict MMP and TIMP expression and activity in rat aortic SMCs of corresponding origins.

FIG. 29 shows Western blot analysis confirming the differential amounts of MMP9 and TIMP1 proteins in the IL-1β-treated SMCs of unique origins.

FIG. 30 shows the proteolytic abilities of the SMCs, as assessed by elastase and collagenase assays over 2.5 d. The origin-specific SMCs (top panels) replicated similar trends of elastin and collagen degradation as the rat aortic SMCs (bottom panels) in response to IL-1β.

FIG. 34 shows RTQPCR validation of selected genes from microarray data in human pluripotent stem cell-derived SMCs. Data demonstrated distinct transcriptional signatures found in origin-specific SMC subtypes where GATA4 and HAND2 mark SMCs of lateral plate mesoderm origin; HOXA4 and HOXA5 mark SMCs of paraxial mesoderm origin; MSX2 and GBX2 mark SMCs of neuroectoderm origin.

FIG. 35 shows further RTQPCR validation with human foetal aortic SMCs using origin specific markers. Root SMCs originate from lateral plate mesoderm; arch SMCs originate from paraxial mesoderm; thoracic descending SMCs originate from neuroectoderm.

DETAILED DESCRIPTION OF INVENTION

Figure 1A:
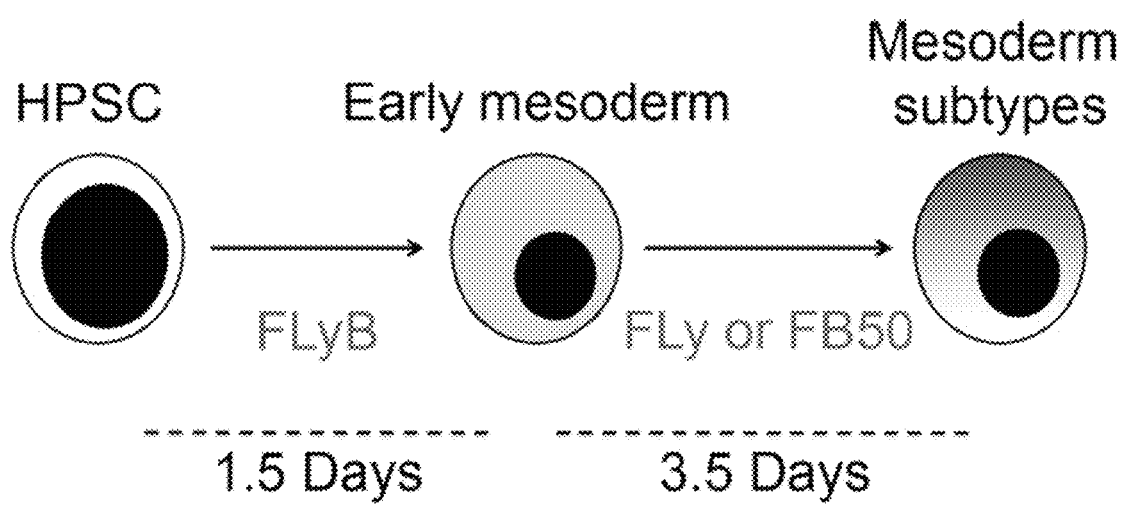
FIG. 1A shows a protocol for mesoderm differentiation.

A pluripotent cell is a cell which exhibits an undifferentiated phenotype and is potentially pluripotent i.e. it is capable of differentiating into any foetal or adult cell type of any of the three germ layers (endoderm, mesoderm and endoderm).

A pluripotent cell is distinct from a totipotent cell and cannot give rise to extraembryonic cell lineages.

A pluripotent cell may express one or more of the following pluripotency associated markers: Oct4, Sox2, Alkaline Phosphatase, SSEA-3, Nanog, SSEA-4, Tra-1-60, KLF-4 and c-myc. A human pluripotent cell may lack markers associated with specific differentiative fates, such as Bra, Sox17, FoxA2, αFP, Sox1, NCAM, GATA6, GATA4, Hand1 and CDX2.

Pluripotent cells may be mammalian cells, preferably human cells.

The population of pluripotent cells may be clonal i.e. genetically identical cells descended from a single common ancestor cell.

A population of pluripotent calls suitable for use in the present methods may be substantially free from one or more other cell types. Pluripotent cells may, for example, be separated from other cell types, using any technique known to those skilled in the art, including those based on the recognition of extracellular epitopes by antibodies and magnetic beads or fluorescence activated cell sorting (FACS) including the use of antibodies against extracellular regions of molecules found on stem cells such as SSEA4.

Pluripotent cells may include embryonic stem cells (ESCs), fetal and adult somatic stem cells and iPS cells Suitable embryonic stem cells may be obtained using conventional techniques. For example, ESCs cells may be obtained from a cultured ESC cell line, for example a hESC line. Numerous cultured hESC lines are publically available from repositories (e.g. NIH Human Embryonic Stem Cell Registry), such as CHB-1 to CHB-12, RUES1 to RUES3, HUES1 to HUES28, HUES45, HUES48, HUES49, HUES53, HUES62 to HUES66, WA01 (H1), WA07 (H7), WA09 (H9), WA13 (H13), WA14 (H14), to NYUES1 to NYUES7, MFS5, and UCLA1 to UCLA3. Further examples of suitable human embryonic stem cell lines are described in (Thomson J A et al Science 282: 1145-1147 (1998); Reubinoff et al. Nat Biotechnol 18:399-404 (2000); Cowan, C. A. et al. N. Engl. J. Med. 350, 1353-1356 (2004), Gage, F. H., et al. Ann. Rev. Neurosci. 18 159-192 (1995); and Gotlieb (2002) Annu. Rev. Neurosci 25 381-407); Carpenter et al. Stem Cells. 5(1): 79-88 (2003). Potentially clinical grade hESCs are described in Klimanskaya, I. et al. Lancet 365, 1636-1641 (2005) and Ludwig, T. E. et al. Nat. Biotechnol. 24, 185-187 (2006).

In some preferred embodiments, suitable hESCs are obtained without destroying a human embryo.

In other embodiments, the pluripotent cells are not hESCs, and may, for example, be iPS cells or fetal or adult somatic stem cells.

iPS cells are pluripotent cells which are derived from non-pluripotent, fully differentiated ancestor cells. Suitable ancestor cells include adult fibroblasts and peripheral blood cells. Ancestor cells are typically reprogrammed by the introduction of pluripotency genes or proteins, such as Oct4, Sox2 and Sox1 into the cell. The genes or proteins may be introduced into the differentiated cells by any suitable technique, including plasmid or more preferably, viral transfection or direct protein delivery. Other genes, for example Kif genes, such as Kif-1, -2, -4 and -5; Myc genes such as C-myc, L-myc and N-myc; nanog; and Lin28 may also be introduced into the cell to increase induction efficiency. Following introduction of the pluripotency genes or proteins, the ancestor cells may be cultured. Cells expressing pluripotency markers may be isolated and/or purified to produce a population of iPS cells. Techniques for the production of iPS cells are well-known in the art (Yamanaka et al Nature 2007; 448:313-7; Yamanaka 6 2007 Jun. 1; 1(1):39-49. Kim et al Nature. 2008 Jul. 31; 454(7204):646-50; Takahashi Cell. 2007 Nov. 30; 131(5): 861-72. Park et al Nature. 2008 Jan. 10; 451(7175):141-6; Kim et al Cell Stem Cell. 2009 Jun. 5; 4(6):472-6; Vallier, L., et al. Stem Cells, 2009. 9999(999A) p. N/A.).

iPS cells may be derived from cells, such as fibroblasts, obtained, from an individual without a genetic disorder. iPS cells derived from an individual without a genetic disorder may be used as described herein to produce lineage specific SMCs with a normal (i.e. non-disease associated) genotype.

iPS cells may be derived from cells, such as fibroblasts, obtained from individuals with distinct genetic backgrounds. For example, iPS cells may be produced from cells from individuals having a cardiovascular or atherosclerotic disease, individuals having a high risk of a cardiovascular or atherosclerotic disease and/or individuals with a low risk of cardiovascular or atherosclerotic disease. SMCs produced as described herein from individuals with distinct genetic backgrounds may be useful in studying the mechanisms of cardiovascular or atherosclerotic disease and identifying therapeutic targets Cardiovascular or atherosclerotic diseases include atherosclerosis, cardiovascular ischaemia, such as ischaemic (coronary) heart disease; myocardial ischaemia (angina); chronic and critical lower limb ischaemia; and visceral ischaemia; infarction, such as myocardial infarction; aneurysm and aneurysmal disease; atheromatous peripheral vascular disease; aortoiliac disease; renal artery disease; cerebrovascular disease; stroke; atherosclerotic retinopathy; hypercoagulative disorder; thrombosis and aberrant blood clotting; restenosis, for example, after angioplasty and/or stenting; transplant arteriopathy and hypertension.

iPS cells may be derived from cells, such as fibroblasts, obtained from an individual with a genetic disorder, for example a genetic disorder associated with SMC dysfunction or death, such as Marfan syndrome, Loeys-Dietz syndrome, Ehlers-Danlos syndrome, or CADASIL, or a genetic disorder which has vascular symptoms or complications. Any cell with the genotype of the disorder, for example a genetic mutation or defect, may be used to produce iPS cells, although samples of fibroblasts, e.g. dermal fibroblasts, may be conveniently obtained.

iPS cells which are produced from cells obtained from an individual with a genetic disorder may be used as described herein to produce SMCs of defined lineages which have the genotype of the genetic disorder. Typically, the SMCs will contain the genetic mutation or defect which is associated with the genetic disorder. These cells may be useful in treating patients with the genetic disorder as described above or in disease modelling and screening.

Pluripotent cells for use in the present methods may be obtained by culturing cells from a pluripotent cell line using conventional techniques (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)) For example, pluripotent cells suitable for use in the present methods may be conventionally cultured in a culture dish, on a layer of feeder cells, such as irradiated mouse embryonic fibroblasts (MEF), at an appropriate density (e.g. $10^5$ to $10^6$ cells/60 mm dish), or on an appropriate substrate with feeder conditioned or defined medium. Pluripotent cells for use in the present methods may be passaged by enzymatic or mechanical means. Suitable culture media for pluripotent cells include Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml FGF2.

Other suitable culture media for pluripotent cells include Knockout (KS) medium supplemented with 4 ng/ml FGF2; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml human FGF2; and DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin.

In preferred embodiments, a population of pluripotent cells for use in the present methods may be cultured in chemically defined medium (CDM) with activin A (10 ng/mL) and FGF2 (20 ng/mL) to maintain pluripotency before differentiation is induced as described below (Vallier et al., 2005). Pluripotent cells may be harvested using collagenase-free reagents, for example Accutase™ (BioWest).

A progenitor cell is a partially differentiated precursor cell which is a daughter or descendant of an undifferentiated pluripotent cell, with a more committed phenotype and/or a more reduced differentiation potential compared to the original pluripotent cell. Progenitor cells are committed to a specific development lineage which is capable of giving rise to SMCs, e.g. neuroectodermal progenitor cells are able to differentiate under appropriate conditions into SMCs found in the ascending and arch of the aorta, the ductus arteriosus, the innominate and right subclavian, both common carotids, cerebral vessels, and in all the arteries found in the head and neck; lateral mesodermal progenitor cells are able to differentiate under appropriate conditions into SMCs found in abdominal blood vessels, such as the descending abdominal aorta, iliac, femoral, aortic root and coronary arteries, and placental vessels; and paraxial mesodermal progenitor cells are able to differentiate under appropriate conditions into SMCs found in the descending thoracic aorta.

Culturing of the pluripotent cells in a chemically defined medium (CDM), preferably a humanised CDM, supplemented with one or more differentiation factors as described herein induces the pluripotent cells to differentiate into progenitor cells of a defined embryonic lineage.

The expression of one or more progenitor cell markers and/or one or more pluripotent cell markers may be monitored and/or detected in the population of differentiating cells. This allows the extent of differentiation of the cell population to be determined during cell culture.

To induce differentiation of the pluripotent cells into early mesoderm or primitive streak cells, the population of pluripotent cells is cultured in an early mesoderm induction medium. The early mesoderm induction medium is a chemically defined medium (CDM) which (i) stimulates signalling pathways mediated by SMAD1, SMAD5 and SMAD9; (ii) inhibits phosphatidylinositol 3-kinase (PI3K) and (iii) has fibroblast growth factor (FGF) activity.

Early mesoderm or primitive streak cells express Brachyury (T), TBX6, MIXL1, EOMES, and MESP1, but do not express Oct4 or Nanog.

A chemically defined medium is a nutritive solution for culturing cells which contains only specified components, preferably components of known chemical structure. In embodiments in which the pluripotent cells are human, the chemically defined medium may be humanised. A humanised chemically defined medium is devoid of components or supplements derived from non-human animals, such as Foetal Bovine Serum (FBS), Bovine Serum Albumin (BSA), end mouse-feeder cells The media described herein may comprise a chemically defined basal medium. Suitable chemically defined basal media include IMDM and/or F12 supplemented with insulin, for example at 0.5 µg/ml to 70 µg/ml, transferrin, for example at a concentration of 1.5 µg/ml to 150 µg/ml, an antioxidant, such as 1-thiolglycerol, for example at a concentration of 45 µM to 4.5 mM, and lipids and one or more of human serum albumin, polyvinyl alcohol (PVA), Plasmanate™ (human albumin, alpha-globulin and beta globulin: Talecris Biotherapeutics NC USA) or Buminate™ (human albumin: Baxter healthcare), for example at a concentration of 0.5 mg/ml to 50 mg/ml.

Suitable chemically defined basal media include Johansson and Wiles CDM (Johansson and Wiles (1995) Mol Cell Biol 15, 141-151) which is supplemented with polyvinyl alcohol, insulin, transferrin and defined lipids. Johansson and Wiles CDM consists of: 50% IMDM (Gibco) plus 50% F12 NUT-MIX (Gibco); 7 µg/ml insulin; 15 µg/ml transferrin; 1 mg/ml polyvinyl alcohol (PVA; 1% chemically defined lipid concentrate (Invitrogen); and 450 µM 1-thiol glycerol.

Other suitable chemically defined basal media include RPMI-1640. RPMI-1640 (Moore, G. E, and Woods L. K., (1976) Tissue Culture Association Manual, 3, 503-503) is a serum-free basal medium containing inorganic salts, amino acids, vitamins, antioxidants and buffers. RPMI-1640 is well known in the art and readily available from commercial sources (e.g. Sigma-Aldrich MI USA). Other suitable chemically defined basal medium are known in the art.

In some embodiments, the chemically defined basal medium may be supplemented with polyvinyl alcohol (PVA) at a concentration of 0.5 mg/ml to 50 mg/ml to avoid the use of Bovine or Human serum albumin. Chemically defined basal medium supplemented with polyvinyl alcohol is commonly referred to as CDM-PVA.

In the media described above, the chemically defined basal medium may be supplemented with additional factors, including growth factors, preferably recombinant human factors, to provide the activities set out above. Preferably the media described herein are serum-free. The use of serum-free conditions and the absence of animal products facilitate scale-up for clinical applications A medium described herein with fibroblast growth factor (FGF) activity may be supplemented with fibroblast growth factor.

Fibroblast growth factor is a protein factor which stimulates cellular growth, proliferation and cellular differentiation by binding to a fibroblast growth factor receptor (FGFR). Suitable fibroblast growth factors include any member of the FGF family, for example any one of FGF1 to FGF14 and FGF15 to FGF23.

Preferably, the fibroblast growth factor is FGF2 (NCBI GeneID: 2247, nucleic acid sequence NM_002006.3 GI: 41352694, amino acid sequence NP_001997.4 GI: 41352695); FGF4 (NCBI GeneID: 2249, nucleic acid sequence NM_002007.2 GI: 196049393, amino acid sequence NP_001998.1 GI: 4503701); FGF5 (NCBI GeneID: 2250, nucleic acid sequence NM_004464.3 GI: 73486654, amino acid sequence NP_004455.2 GI: 73486655); FGF7 (also known as keratinocyte growth factor (or KGF), NCBI GeneID: 2252, nucleic acid sequence NM_002009.3 GI: 219842354, amino acid sequence NP_002000.1 GI: 4503705); FGF8 (NCBI GeneID: 2253 nucleic acid sequence NM_001206389.1 GI: 329755302, amine acid sequence NP_001193318.1 GI: 329755303); or FGF10 (NCBI GeneID: 2255, nucleic acid sequence NM_004465.1 GI: 4758359, amino acid sequence NP_004456.1 GI: 4758360).

Most preferably, the fibroblast growth factor is FGF2 (Amit, M., et al. *Embryonic Biology* 227:271-278 (2000)).

Fibroblast growth factors, such as FGF2, may be produced using routine recombinant techniques or obtained from commercial suppliers (e.g. R&D Systems, Minneapolis, Minn.; Stemgent Inc, USA).

Conveniently, the concentration Of FGF in a medium described herein may be from 1 to 150 ng/ml, for example, 10 to 50 ng/ml, 10 to 50 ng/ml or 5 to 25 ng/ml, preferably about 20 ng/ml.

A medium described herein which stimulates SMAD1, SMAD5 and SMAD9 mediated intracellular signalling pathway may be supplemented with a TGFβ ligand.

The TGFβ ligand may be a Bone Morphogenic Protein (BMP). Bone Morphogenic Proteins bind to Bone Morphogenic Protein Receptors (BMPRs) and stimulate intracellular signalling through pathways mediated by SMAD1, SMAD5 and SMAD9. Suitable Bone Morphogenic Proteins include any member of the BMP family, for example BMP2, BMP3, BMP4, BMP5, BMP6 or BMP7. Preferably, the second TGFβ ligand is BMP2 (NCBI GeneID; 650, nucleic acid sequence NM_001200.2 GI: 80861484; amino acid sequence NP_001191.1 GI: 4557369) or BMP4 (NCBI GeneID: 652, nucleic acid sequence NM_001202.3 GI: 157276592; amino acid sequence NP_001193.2 GI: 157276593).

Bone Morphogenic Proteins may be produced using routine recombinant techniques or obtained from commercial suppliers (e.g. R&D, Minneapolis, USA, Stemgent Inc, USA).

Conveniently, the concentration of a Bone Morphogenic Protein, such as BMP2 or BMP4 in the medium may be from 1 to 500 ng/ml, preferably, from 1 to 150 ng/ml, for example about 10 ng/ml or 30-100 µM.

A medium described herein which inhibits PI3K may be supplemented with a PI3K inhibitor.

PI3K inhibitors inhibit the activity of phosphatidylinositol 3-kinases, such as phosphatidylinositol-4,5-bisphosphate 3-kinase (EC 2.7.1.153).

Suitable PI3K inhibitors include wortmannin; LY301497 (17-b-hydroxywortmannin); LY294002 (2-morpholin-4-yl-8-phenylchromen-4-one: Maclean et al (2007) *Stem Cells* 25 29-38); CLB1309 (FN309: (±)-2-((1-[7-methyl-2-(morpholin-4-yl)-4-oxo-pyrido[1,2-a]pyrimidin-9-yl]ethyl)amino) benzoic acid); PX-866 ((1E,4S,4aR,5R,6aS,9aR)-5-(Acetyloxy)-1-[(di-2-propen-1-ylamino)methylene]-4,4a,5,6,6a,8,9,9a-octahydro-11-hydroxy-4-(methoxymethyl)-4a,6a-dimethylcyclopenta[5,6]naphtho[1,2-c]pyran-2,7,10(1H)-trione); IC87114 (quinolone pyrrolopyrimidine); GDC-0941 (2-(1H-Indazol-4-yl)-6-[[4-(methylsulfonyl)-1-piperazinyl] methyl]-4-(4-morpholinyl)-thieno[3,2-d]pyrimidine); TGX-221 (7-methyl-2-(4-morpholinyl)-9-[1-(phenylamino) ethyl]-4H-pyrido[1,2-a]pyrimidin-4-one), quercetin; BEZ235; XL147; X1765; PX-866; ZSTK474 (2-(2-difluoromethylbenzimidazol-1-yl)4,6-dimorpholino-1,3,5-triazine); and SF1126 (2-[2-methoxyethylamino]-8-phenyl-4H-1-benzopyran-4-one). Other PI3K inhibitors are available in the art.

In some preferred embodiments, the PI3K inhibitor is LY301497.

Suitable PI3K inhibitors may be obtained from commercial suppliers (e.g. Calbiochem CA USA).

For example, the medium may contain 1 to 100 µM PI3K inhibitor, such as LY294002, for example, 5-10 µM and preferably about 10 µM.

In some embodiments, the early mesoderm induction medium may consist of CDM supplemented with FGF2 (for example 5 to 25 ng/ml, preferably about 20 ng/ml), BMP-4 (for example at 5 to 20 ng/ml, preferably about 10 ng/ml) and a phosphatidylinositol 3-kinase inhibitor, preferably LY294002 (for example at 5-30 µM, preferably 5-10 µM).

The pluripotent cells may be cultured for 24 to 48 hours, preferably 36 hours in the early mesoderm induction medium to produce the early mesoderm or primitive streak progenitor cells.

To induce differentiation of the early mesoderm cells into lateral mesodermal cells, the population of early mesoderm cells is cultured in a lateral mesoderm induction medium. The lateral mesodermal medium is a chemically defined medium (CDM) which (i) has fibroblast growth factor activity and (ii) stimulates SMAD1, SMAD5 and SMAD9 mediated signalling pathways.

Suitable chemically defined medium (CDM) and differentiation factors which have fibroblast growth factor activity and stimulate SMAD1, SMAD5 and SMAD9 mediated signalling pathways are described above.

Lateral mesoderm cells express CDX2, PDGFRa, GATA4, FLK1, MESP2, KDR, NKX2.5 and ISL1 but do not express Brachyury (T).

The lateral mesoderm induction medium may consist of CDM supplemented with FGF2 (for example 5 to 25 ng/ml, preferably about 20 ng/ml), and BMP-4 (for example at 30-100 µM).

The early mesoderm cells may be cultured for at least 2 days or at least 3 days, for example 2 to 6 days, preferably about 3.5 days, in the lateral mesoderm induction medium to produce the lateral mesodermal progenitor cells.

To induce differentiation of the early mesoderm cells into paraxial mesodermal cells, the population of early mesoderm cells is cultured in a paraxial mesoderm induction medium. The paraxial mesodermal medium is a chemically defined medium (CDM) which (i) has fibroblast growth factor activity and (ii) inhibits phosphatidylinositol 3-kinase (PI3K) activity.

Suitable chemically defined medium (CDM) and differentiation factors which have fibroblast growth factor activity and inhibit phosphatidylinositol 3-kinase (PI3K) activity are described above.

Paraxial mesoderm cells express TBX6, MEOX1, TCF15 and PAX1 but do not express FLK1, KDR, NKX2.5 or ISL1.

The paraxial mesoderm induction medium may consist of CDM supplemented with FGF2 (for example 5 to 25 ng/ml, preferably about 20 ng/ml), and a phosphatidylinositol 3-kinase inhibitor, preferably LY294002 (for example at 5-30 µM, preferably 5 to 10 µM).

The early mesoderm cells may be cultured for at least 2 days, or at least 3 days, for example 2 to 6 days, preferably about 3.5 days, in the paraxial mesoderm induction medium to produce the paraxial mesodermal progenitor cells.

To induce differentiation of the pluripotent cells into neuroectoderm cells, the population of pluripotent cells is cultured in a neuroectoderm mesoderm induction medium. The neuroectoderm induction medium is a chemically defined medium (CDM) which (i) has fibroblast growth factor (FGF) activity and (ii) has activin inhibition activity.

In some embodiments, the neuroectoderm induction medium may also have (iii) BMP signalling inhibition activity.

Suitable chemically defined medium (CDM) and differentiation factors which have fibroblast growth factor activity are described above.

A medium described herein which has activin inhibition activity may be supplemented with an activin antagonist.

Suitable activin antagonists may inhibit the activity of Activin Receptor-Like Kinases, such as ALK4, ALK5 and ALK7.

Activin A (NCBI GeneID: 3624 nucleic acid reference sequence NM_002192.2 GI: 62953137, amino acid reference sequence NP_002183.1 GI: 4504699) is a dimeric polypeptide which exerts a range of cellular effects via stimulation of the Activin/Nodal pathway.

A number of antagonists of Activin/Nodal are known, including inhibitors of smad2/3 signalling, such as SB431542 (4-(5-Benzol[1,3]dioxol-5-yl-4-pyridin-2-yl-1H-imidazol-2-yl)-benzamide hydrate; Sigma, Tocris Bioscience, Bristol UK; (Inman et al Mol Pharmacol (2002) 62 1 65-74), naringenin (5,7-dihydroxy-2-(4-hydroxyphenyl)chroman-4-one), SIS3 (6,7-Dimethoxy-2-((2E)-3-(1-methyl-2-phenyl-1H-pyrrolo[2,3-b]pyridin-3-yl-prop-2-enoyl))-1,2,3,4-tetrahydroisoquinoline), and soluble protein factors, such as lefty (e.g. human lefty 2: NP_003231.2 GI: 27436881), cerberus (e.g. human Cerberus 1; NP_005445.1 GI: 4885135) or follistatin (e.g. human follistatin; NP_006341.1 GI: 5453652). Conveniently, the concentration of antagonist in the medium may be from 1 to 100 µM, preferably about 10 µM.

A medium described herein which has BMP signalling inhibition activity may be supplemented with a BMP inhibitor.

Various BMP inhibitors are known in the art, including LDN-193189 (4-(6-(4-(piperazin-1-yl)phenyl)pyrazolo[1,5-a]pyrimidin-3-yl)quinoline; Yu et al (2008) Nat Chem Biol 4 33-41)), GDF3, Noggin, and dorsomorphin (6-[4-[2-(1-Piperidinyl)ethoxy]phenyl]-3-(4-pyridinyl)pyrazolo[1,5-a]pyrimidine; Yu et al (2008) Nat Chem Biol 4 33-41)). Conveniently, the concentration of BMP inhibitor in the medium may be from 1 to 100 µM, preferably about 10 µM.

Neuroectoderm cells express Sox2 in absence of Oct4 and may also express OLIG3, SIX1, SIP1, Sox1, Sox3, Nestin, GBX2 and HOXA1.

The neuroectoderm induction medium may consist of CDM supplemented with FGF2 (for example 5 to 25 ng/ml, preferably about 20 ng/ml), and an activin antagonist, for example SB431542 (for example at 5-20 µM, preferably 10 µM).

The pluripotent cells may be cultured for at least 3 days, or at least 5 days, for example 6 to 9 days, preferably 7 days, in the neuroectoderm induction medium to produce the neuroectodermal progenitor cells.

The culture of mammalian cells is well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho WY et al J Immunol Methods. (2006) 310:40-52, Handbook of Stem Cells (ed. R. Lanza) ISBN: 0124366430). Media and ingredients thereof may be obtained from commercial sources (e.g. Gibco, Roche, Sigma, Europa bioproducts, R&D Systems). Standard mammalian cell culture conditions may be employed, for example 37° C., 21% Oxygen, 5% Carbon Dioxide. Media is preferably changed every two days and cells allowed to settle by gravity.

Progenitor cells with a defined embryonic lineage produced by the present methods may be substantially free from other cell types, for example pluripotent cells or cells of other embryonic lineages. In some embodiments, progenitor cells may be separated from other cell types using any technique known to those skilled in the art.

Early mesoderm progenitors, lateral mesodermal progenitors, paraxial mesodermal progenitors and neuroectoderm progenitors produced in the methods described herein may be isolated and/or purified. Progenitor cells may be separated from other cell types in the population using any convenient technique, including methods based on the recognition of extracellular epitopes by antibodies and magnetic bead or fluorescence activated cell sorting (MACS or FACS) including the use of antibodies against extracellular regions of characteristic markers as described above. For example, lateral mesoderm progenitor cells may be isolated by flow cytometry based on the expression of KDR, a cell surface marker.

In some embodiments, the pluripotent cells may comprise a reporter, preferably a fluorescent reporter, which is operably linked to a tissue-specific promoter (i.e. a neuroectoderm, lateral mesoderm or paraxial mesoderm specific promoter). Following differentiation into lineage specific progenitor cells as described herein, cells which express the reporter may be isolated and/or purified from other cell types, for example by fluorescence activated cell sorting (FACS).

Populations of progenitor cells may, for example, be expanded or propagated in culture using standard mammalian cell culture techniques before further differentiation into SMCs.

Further aspects of the invention provide a population of isolated lateral mesoderm progenitor cells obtained or obtainable by a method described herein and a population of isolated paraxial mesoderm cells obtained or obtainable by a method described herein.

To induce differentiation of the lineage specific progenitor cells progenitor cells into lineage specific SMCs, the population of progenitor cells is cultured in an SMC induction medium. The SMC induction medium is a chemically defined medium (CDM) which (i) has platelet derived growth (PDGF) factor activity and (ii) activates Smad2/3 mediated signalling pathways.

Smooth Muscle Cells may include vascular smooth muscle cells.

A medium described herein which has platelet derived growth (PDGF) factor activity may be supplemented with a PDGF receptor ligand. PDGF receptor ligands include platelet derived growth factor (PDGF), vascular endothelial growth factor (VEGF; Ball, et al (2007) The Journal of Cell Biology 177(3): 489-500), for example VEGF isoforms A, B, C and D, and placental growth factor (PGF), for example PGF isoforms 1 to 4.

PDGF may be a PDGF-AA, PDGF-BB or PDGF-CC homodimer (PDGF-B; NCBI GeneID: 5155 nucleic acid reference sequence NM_002608.2 GI: 208879461, amino acid reference sequence NP_002599.1 GI: 4505681; PDGF-A; NCBI GeneID: 5154 nucleic acid reference sequence NM_002607.5 GI: 197333758, amino acid reference sequence NP_002598.4 GI: 77695917; PDGF-C; NCBI GeneID: 5134 nucleic acid reference sequence NM_016205.2 GI: 307691204, amino acid reference sequence NP_057289.1 GI: 9994187) or may be a PDGF-AB heterodimer. PDGF exerts a range of mitogenic effects via binding to the PDGF-Receptor. PDGF is available from commercial suppliers. For example, the SMC induction medium may contain 1 to 100 ng/ml PDGF, for example, 5-20 ng/ml and preferably about 10 ng/ml.

A medium described herein which activates Smad2/3 signalling pathways may be supplemented with a TGFβ ligand, such as TGF-β1, TGF-β2, TGF-β3; Activin, Nodal, Growth and differentiation factor (GDF), e.g. GDF1 and GDF11; retinoic acid and its derivatives or sphingosine-1-phosphate.

TGFβ1 (NCBI GeneID; 7040 nucleic acid reference sequence NM_000660.4 GI: 260655621, amino acid reference sequence NP_000651.3 GI: 63025222) is a homodimeric polypeptide which regulates proliferation and differentiation (Watabe, T. et al (2009). Cell Res. 19:103-115).

Recombinant human TGFβ is readily available from commercial sources (e.g. Stemgent Inc. MA USA). The SMC induction medium may contain 0.5 to 50 ng/ml TGF-β1, for example, about 2 ng/ml.

The SMC induction medium may consist of CDM supplemented with PDGF (for example 5-20 ng/ml and preferably about 10 ng/ml.), and TGF-β1 (for example at 1 to 5 ng/ml for example, about 2 ng/ml).

The progenitor cells may be cultured for at least 3 days, at least 6 days or at least 9 days, for example 9 to 15 days, preferably about 12 days, in the SMC induction medium to produce the lineage specific SMCs.

An SMC produced as described herein may express MYH11, SMTN, CNN1, ACTA2 TAGLN, TAGLN2, CALD1, VIM, DES, MYLK, RGS5, AXL, PDGFRB, CSRP2 and AEBP1.

An SMC produced as described herein may lack lineage specific markers, for example one or more of the mesodermal or neuroectodermal markers described above.

SMCs of different embryonic origins may be distinguished by their gene expression profiles. Gene expression profiles may be determined using conventional methods, such as microarrays.

The expression of one or more SMC markers may be monitored and/or detected in the population of cells. For example, the expression or production of MYH11, SMTN, CNN1, ACTA2 and TAGLN by the population of SMCs may be determined. This allows the extent of differentiation in the population of cultured to be determined and/or monitored. The expression of cell markers may be determined by any suitable technique, including immunocytochemistry, immunofluorescence, RT-PCR, immunoblotting, fluorescence activated cell sorting (FACS), and enzymatic analysis.

The ability of SMCs in the population to perform one or more SMC functions may be monitored and/or determined. For example, the contractile properties of the SMCs, the response of the SMCs to a vasoconstrictor or the distribution of the SMCs in a model system may be monitored and/or determined.

Suitable vasoconstrictors are well-known in the art and include carbachol, potassium chloride, angiotensin II, catecholamines (e.g. adrenaline, noradrenaline, phenylephrine), serotonin, histamine and cholinergic agonists (e.g. acetylcholine).

The effect of a vasoconstrictor on calcium signalling in the SMCs may be determined, for example using a calcium sensitive fluorescent dye, such as fluo-4.

The effect of a vasoconstrictor on contraction of the SMCs may be determined. For example, SMCs may be embedded in an extracellular matrix, such as a collagen gel, and the contractile responses of the matrix to vasoconstrictors determined.

In some embodiments, the distribution of cells in three dimensional cell culture may be determined. For example, the ability of the SMCs to occupy periendothelial regions in luminal structures may be determined. SMCs may be cultured with endothelial cells in an extracellular matrix (e.g. a gel such as Matrigel™). Following culture, the distribution of the SMCs in the matrix may be determined.

Functional SMCs may be distributed in the peri-endothelial regions around endothelial derived chords in the matrix.

Following culturing in the medium as described above, the population of lineage specific SMCs may be isolated and/or removed from the medium and/or purified.

The population of lineage specific SMCs may be substantially free from other cell types. For example, the population may contain 70% or more, 80% or more, 85% or more, 90% or more, or 95% or more lineage-specific SMCs, following culture in the medium. If required, the population of lineage-specific SMCs may be purified by any convenient technique, including those based on the recognition of extracellular epitopes by antibodies and magnetic beads or fluorescence activated cell sorting (FACS) including the use of antibodies against extracellular regions of SMC characteristic markers, as described above.

Lineage specific SMCs may be expanded or maintained in culture, for example for up to 3 months.

Lineage specific SMCs may be stored, for example by freezing using conventional cell storage techniques.

Lineage specific SMCs may be used in cell-based therapies, disease modelling or screening assays, as described below.

In some embodiments, populations of SMCs of different embryonic lineages may be produced from the same clonal population of pluripotent cells. This allows the production of genetically identical SMC populations with different embryonic lineages. This may be useful in comparative studies. For example, disease mechanisms (disease modelling) and susceptibility may be identified in different populations of SMCs of different lineages in order to identify disease resistant populations of SMCs.

In some embodiments, the effect of an inflammatory mediator or cytokine, such as histamine, IFNγ, IL-8, leukotriene B4, nitric oxide, prostaglandin, TNFα or IL-1, on a population of SMCs of a defined Lineage may be determined.

The responses of populations of SMCs of different lineages may be determined and compared.

The population of lineage specific SMCs may be admixed with other reagents, such as buffers, carriers, diluents, preservatives or pharmaceutically acceptable excipients. Suitable reagents are described in more detail below.

As described above, lineage specific SMCs may be generated from iPS cells from an individual with a genetic disorder. Lineage specific SMCs with the genotype of a genetic disorder may be useful in modelling or characterising the genetic disorder and its vascular effects. A lineage specific SMC with the genotype of a genetic disorder may display a genetic disorder associated phenotype or one or more vascular pathologies associated with the genetic disorder. This may be useful in disease modelling and screening for therapeutic compounds.

Genetic disorders include diseases associated with SMC dysfunction or death, such as Marfan syndrome, in which a fibrillin-1 mutation leads to SMC death in the ascending aorta, leading to aortic dilatation and dissection (Milewicz D M et al Circulation. 2005 Mar. 22; 111(11):e150-7); CADASIL (cerebral autosomal dominant arteriopathy and subcortical ischaemic leucoencephalopathy), in which a Notch3 mutation leads to degeneration of SMCs in the small arterioles supplying the brain, causing multiple cerebral haemorrhages and infarcts (Ayata C. Stroke. 2010 October; 41(10 Suppl):S129-34) and Loeys-Dietz syndrome (Loeys B L, et al. Nat Genet. 2003 March; 37(3):275-81.), in which mutations in ACTA2 or MYH11 lead to thoracic aortic aneurysms and dissection.

A method of producing a population of lineage specific SMCs with a genetic disorder genotype may comprise;
providing iPS cells from an individual with a genetic disorder, and;
producing a population of lineage specific SMCs from the iPS cells as described above,
said lineage specific SMCs having thus genetic disorder genotype.

Once produced, a population of lineage specific SMCs with the genetic disorder genotype may be cultured, expanded and maintained, for example for use in disease modelling or screening.

Lineage specific SMCs may be generated from iPS cells from an individual in need of increased tissue vascularisation, or with diseased, damaged or dysfunctional vascular tissue. These lineage specific SMCs may be useful in treating the individual, for example by direct administration of the SMCs to the individual or co-administration with endothelial cells, such that blood vessels are formed or repaired in vivo; or in the in vitro or ex vivo production of a bio-engineered blood vessel for use as a graft or bypass, for example a coronary artery bypass grafting, peripheral artery bypass or haemodialysis graft, which is surgically implanted in the individual.

Suitable methods for the production of bio-engineered blood vessels are known in the art. The SMCs of the appropriate lineage may be selected, depending on the vascular tissue or the tissue being vascularised or revascularized.

Another aspect of the invention provides a population of isolated lineage specific (e.g. neuroectodermal, lateral mesodermal or paraxial mesodermal) SMCs. The population may be substantially pure, for example at least 70%, at least 80% or at least 90% of the cells in the population may be SMCs of the defined lineage. Suitable populations of lineage specific SMCs may be produced by a method described above.

Another aspect of the invention provides a combination of two, three or more separate populations of isolated SMCs, each population having a different embryonic lineage (e.g. one of neuroectodermal, lateral mesodermal or paraxial mesodermal SMCs).

Lineage specific SMCs produced by the methods described herein may display one or more functions or functional characteristics specific to mature SMCs. For example, the SMCs may be able display contraction and/or increased calcium signalling in response to a vasoconstrictor, occupy periendothelial regions in luminal structures and/or be able to regulate blood flow/pressure in model systems.

A population of neuroectodermal, lateral mesodermal or paraxial mesodermal SMCs, for example, produced by a method described herein for use in a method of treatment of the human or animal body, for example in the vascularisation or revascularisation of tissue or the treatment of damaged, diseased or dysfunctional vascular tissue. The treatment of damaged, diseased or dysfunctional vascular tissue may include coronary artery disease, peripheral vascular disease and other atherosclerotic vascular disease, post angioplasty/stent restenosis, transplant vasculopathy, generation of bio-engineered grafts for bypass surgery, such as coronary or peripheral artery bypass, haemodialysis grafts, or aortic dilatation due to Marfan syndrome or other genetic diseases.

A population of neuroectodermal SMCs may be useful, for example, in the vascularisation or revascularisation of tissue or in the treatment of damaged, diseased or dysfunctional neuroectodermal vascular tissue, such as the ascending and arch of the aorta, the ductus arteriosus, the innominate and right subclavian, both common carotids, cerebral vessels, and head and neck arteries, a population of lateral mesodermal SMCs may be useful in the vascularisation or revascularisation of tissue or in the treatment of damaged, diseased or dysfunctional lateral mesodermal vascular tissue, such as the descending abdominal aorta, iliac, femoral, aortic root, and coronary arteries, and placental vessels, for example lateral mesodermal SMCs may be useful in the treatment of congenital heart abnormalities due to lateral mesoderm defects, and a population of paraxial mesodermal SMCs may be useful in the vascularisation or revascularisation of tissue or in the treatment of damaged, diseased, or dysfunctional paraxial mesodermal vascular tissue, such as the descending thoracic aorta. For therapeutic applications, the lineage specific SMCs are preferably clinical grade SMCs.

A population of lineage specific SMCs, for example produced by a method described herein, may also be used in the production of bioengineered blood vessels. A bioengineered vessel may be produced in vitro or ex vivo and implanted into an individual, for example as a bypass or graft. For example, lineage specific SMCs may be seeded into a tubular biomimetic scaffold material (such as poly-glycolic acid (PGA)) and cultured in a bio-reactor to allow the SMCs to attach to the underlying scaffold. Pulsatile stretch and pressure may be applied inside the graft in combination with the addition of growth factors (such as TGFβ1 and PDGF-BB) to mature the SMCs. The luminal surface of the construct may then be seeded with endothelial cells to produce the engineered graft.

In other embodiments, the lineage specific SMCs may be seeded onto a flat scaffold to form a sheet of cells which may then be rolled into a tubular multilayered structure, the luminal surface of which may then be seeded with endothelial cells.

In these synthetic scaffolds, SMCs may produce extracellular matrix components, such as elastin and collagen, which confer the structural integrity to the construct.

The choice of lineage specific SMC may depend on the site of implantation of the bioengineered vessel. For example, SMCs of a neuroectodermal lineage may be used to repair or replace neuroectodermal vascular tissue, SMCs of a lateral mesodermal lineage may be used to repair or replace lateral mesodermal vascular tissue, and SMCs of a paraxial mesodermal lineage may be used to repair or replace paraxial mesodermal vascular tissue In other embodiments, a population of lineage specific SMCs, for example produced by a method described herein, may be used in the manufacture of a medicament for use in the treatment of damaged, diseased or dysfunctional vascular tissue. For example, a population of neuroectodermal SMCs may be used in the manufacture of a medicament for use in the treatment of damaged, diseased or dysfunctional neuroectodermal vascular tissue, such as the ascending and arch of the aorta, the ductus arteriosus, the innominate and right subclavian, both common carotids, cerebral vessels, and any arteries found in the head and neck; a population of lateral mesodermal SMCs may be used in the manufacture of a medicament for use in the treatment of damaged, diseased or dysfunctional lateral mesodermal vascular tissue, such as the abdominal vascular tissue, such as the descending abdominal aorta, iliac, femoral, aortic root and coronary arteries, and placental vessels; and a population of paraxial mesodermal SMCs may be used in the manufacture of a medicament for use in the treatment of damaged, diseased or dysfunctional paraxial mesodermal vascular tissue, such as the descending thoracic aorta.

A method of increasing the vascularisation or tissue or treating damaged, diseased or dysfunctional vascular tissue as described herein may comprise;

administering a population of lineage specific SMCs produced as described above to an individual in need thereof.

The lineage specific SMCs may be co-administered with endothelial cells, optionally in a scaffold or matrix as described above.

In preferred embodiments, autologous patient matched SMCs may be administered to an individual. Lineage specific SMCs may be produced from iPS cells derived from the individual. For example a method may comprise;

producing iPS cells from a cell sample obtained from an individual, producing a population of lineage specific SMCs from the iPS cells using a method described herein, and optionally formulating the lineage specific SMCs with a pharmaceutically acceptable carrier or excipient.

The population of lineage specific SMCs may be administered to the individual from whom the cell sample was obtained.

Aspects of the invention also extend a pharmaceutical composition, medicament, drug or other composition comprising a population of lineage specific SMCs as described herein, a method comprising administration of such a population or composition to a patient, e.g. for treatment (which may include preventative treatment) of damaged, disease or dysfunctional vascular tissue, as described above, and a method of making a pharmaceutical composition comprising admixing such a population of SMCs with a pharmaceutically acceptable excipient, vehicle or carrier, and optionally one or more other ingredients, such as buffer, preservative, stabiliser or anti-oxidant. Such materials should be non-toxic and should not interfere with the viability of the SMCs. The precise nature of the carrier or other material will depend on the route of administration.

In some embodiments, the lineage specific SMCs may be provided in a scaffold or matrix to facilitate revascularisation, for example as an artificial, blood vessel, graft or bypass for implantation.

Suitable scaffolds may be composed of artificial polymers such as polyglycolic acid (PGA), biological matrix components, such as collagen, or decellularised blood vessels from donors.

A population of lineage specific SMCs which is administered to an individual may be genetically manipulated to produce a therapeutic molecule, for example a drug, growth factor or survival factor (Behrstock S et al, Gene Ther 2006 March; 13(5):379-88, Klein S M et al, Hum Gene Ther 2005 April; 16(4):509-21) or a reporter gene, such as a fluorescent reporter gene, which allows the SMC to be detected and tracked in vivo.

Liquid compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included. The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection.

Lineage specific SMCs may be implanted or infused into a patient by any technique known in the art (e.g. Lindvall, O. (1998) Mov. Disord. 13, Suppl. 1:83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-1555, Le Blanc et al, Lancet 2004 May 1; 363(9419):1439-41). In particular cell suspensions may be injected at a site in a patient which has dysfunction, disease or damaged vascular tissue. SMCs may be injected alone or in combination with other cells such as endothelial cells, to revascularise ischaemic tissues. Cells may be injected intramuscularly or intra-arterially or used to form vascularised tissues ex-vivo before implantation.

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and timecourse of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

A population of lineage specific SMCs produced as described above may be useful in modelling the interaction of test compounds with SMCs, for example in toxicity screening, modelling vascular disease and screening for compounds with potential therapeutic effects.

A method of screening for a compound useful in the treatment of damaged or dysfunctional vascular tissue may comprise;

contacting a population of lineage specific SMCs produced by a method described above with a test compound and determining the effect of the test compound on the lineage specific SMCs and/or the effect of said lineage specific SMCs on the test compound.

The lineage specific SMCs may display a normal genotype or a genetic disorder genotype.

For example the effect of the test compound on the growth, viability, proliferation, phenotypic state, migration, cytokine production, contraction, calcium handling of the lineage specific SMCs may be determined.

An increase in the growth, viability, proliferation, phenotypic state, migration, cytokine production, contraction or calcium handling of the lineage specific SMCs in the presence of the test compound, relative to controls, is indicative that the test compound is useful in the treatment of damaged or dysfunctional vascular tissue. For example, a population of neuroectodermal SMCs may be useful in screening for compounds useful in the treatment of damaged, diseased or dysfunctional neuroectodermal vascular tissue. An increase in the growth, viability, proliferation, phenotypic state, migration, cytokine production, contraction or calcium handling of the neuroectodermal SMCs may be indicative that the test compound is useful in the treatment of damaged, diseased or dysfunctional neuroectodermal vascular tissue. A population of lateral mesodermal SMCs may be useful in screening for compounds useful in the treatment of damaged, diseased or dysfunctional lateral mesodermal vascular tissue, such as the descending abdominal aorta, aortic root and coronary arteries. An increase in the growth, viability, proliferation, phenotypic state, migration, cytokine production, contraction or calcium handling of the lateral mesodermal SMCs may be indicative that the test compound is useful in the treatment of damaged, diseased or dysfunctional lateral mesodermal vascular tissue. A population of paraxial mesodermal SMCs may be useful in screening for compounds useful in the treatment of damaged, diseased or dysfunctional paraxial mesodermal vascular tissue, such as the descending thoracic aorta. An increase in the growth, viability, proliferation, phenotypic state, migration, cytokine production, contraction or calcium handling of the paraxial mesodermal SMCs may be indicative that the test compound is useful in the treatment of damaged, diseased or dysfunctional paraxial mesodermal vascular tissue.

A decrease in growth or viability may be indicative that the compound has a cytotoxic effect on SMCs.

The growth, viability, proliferation, phenotypic state, migration, cytokine production, contraction and/or calcium handling of a lineage specific SMC may be determined using routine techniques.

Gene expression may be determined in the presence relative to the absence of the test compound. For example, the expression of an SMC marker such as SMCs express MYH11, SMTN, CNN1, ACTA2 TAGLN, TAGLN2, CALD1, VIM, DES, MYLK, RGS5, AXL, PDGFRB, CSRP2 and/or AEBP1, may be determined. A decrease in expression is indicative that the compound has a cytotoxic effect. Gene expression may be determined at the nucleic acid level, for example by RT-PCR, or at the protein level, for example, by immunological techniques, such as ELISA, or by activity assays.

One or more functions of the lineage specific SMCs may be determined and/or measured in the presence relative to the absence of the test compound. For example, growth, viability, proliferation, phenotypic state, migration, cytokine production, contraction or calcium handling may be determined and/or measured in the presence relative to the absence of the test compound.

An increase in one or more of these functions in the presence relative to the absence of the test compound may be indicative that the test compound is useful in increasing tissue vascularisation or in the treatment of damaged, diseased or dysfunctional vascular tissue A decrease in one or more of these functions in the presence relative to the absence of the test compound is indicative that the compound has a cytotoxic effect.

In some embodiments, phenotypic state of the SMCs may be determined by high-content screening. Suitable techniques and apparatus for high content screening are well known in the art and include confocal imaging platforms, such as ImageXpress Ultra™ (Molecular Devices USA), Opera™ (PerkinElmer Inc MA USA, and IN Cell 3000™ (GE Amersham Biosciences, UK), and widefield imaging platforms, such as Arrayscan VTI™ (Cellomics) and IN Cell Analyzer 2000™ (GE Healthcare NJ USA).

A method of screening for a compound useful in the treatment of vascular symptoms of a genetic disorder may comprise;

contacting a population of lineage specific SMCs produced as described above with a test compound, and; determining the effect of the test compound on said SMCs.

In some embodiments, lineage specific SMCs with a genetic disorder genotype may be employed and the effect of the test compound on the Lineage specific SMCs may be determined.

The effect may be determined relative to SMCs of other defined lineages. For example, the effect of the test compound on one or more of growth, viability, proliferation, phenotypic state, migration, cytokine production, contraction or calcium handling may be determined. Suitable techniques are well known in the art and include immunostaining, mass spectrometry, Western blots, and enzymatic assays.

A test compound which reduces or minimise phenotypes associated with the genetic disorder in the SMCs may be identified.

Methods as described herein may comprise the step of identifying a test compound which reduces or ameliorates one or more SMC phenotypes or vascular symptoms of a genetic disorder in the lineage specific SMCs. Compounds which reduce disease symptoms or phenotypes may be useful in the development of therapeutics for the treatment of the genetic disorder or its symptoms.

Following identification of a compound which one or more vascular symptoms of a genetic disorder in the lineage specific SMCs, the compound may be modified to optimise its pharmaceutical properties. This may be done using modelling techniques which are well-known in the art.

A test compound identified using one or more initial screens as having a beneficial effect on the SMCs may be assessed further using one or more secondary screens.

A secondary screen may involve testing for a biological function or activity in vitro and/or in vivo, e.g. in an animal model. For example, the ability of a test compound to reduce or ameliorate the progression of the disorder or one or more vascular symptoms or pathologies associated with the genetic disorder in an animal model of the disease may be determined.

Following identification of a test compound which reduces or ameliorates one or more vascular symptoms of a genetic disorder in the lineage specific SMCs, the compound may be isolated and/or purified or alternatively it may be synthesised using conventional techniques of recombinant expression or chemical synthesis. Furthermore, it may be manufactured and/or used in preparation, i.e. manufacture or formulation, of a composition such as a medicament, pharmaceutical composition or drug. These may be administered to individuals for the treatment of vascular symptoms of a genetic disorder.

Other aspects and embodiments of the invention provide the aspects and embodiments described above with the term "comprising" replaced by the term "consisting of" and the aspects and embodiments described above with the term "comprising" replaced by the term "consisting essentially of".

Various further aspects and embodiments of the present invention will be apparent to those skilled in the art in view of the present disclosure.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect, or embodiment of the invention and apply equally to all aspects and embodiments which are described.

Certain aspects and embodiments of the invention will now be illustrated by way of example and with reference to the figures describe above.

EXPERIMENTS

Materials & Methods

Human Embryonic Stem Cell Maintenance and Differentiation

Human embryonic stem cells (hESCs) were cultured in chemically defined medium (CDM) with activin A (10 ng/mL) and FGF2 (20 ng/mL) to maintain pluripotency (Vallier et al, 2005).

An efficient 36 h protocol to differentiate hESCs into early mesoderm was named FlyB (F, FGF2 at 20 ng/ml; Ly, LY294002 at 10 µM and B, BMP4 at 10 ng/ml). Differentiation of paraxial mesoderm can be induced by removal of BMP4 and blockage of the PI3K pathway (1.5 day FLyB+3.5 days FLy, where F is FGF2 at 5-25 ng/ml and Ly is LY294002 at 5-10 µM). Differentiation of lateral plate mesoderm can be induced by increasing the levels of BMP4 and removal of Ly (1.5 day FLyB+3.5 days FB, where F is FGF2 at 5-25 ng/ml and B is BMP4 at 30-100 µM).

Alternatively, treatment with FGF2 (20 ng/mL) and SB431542 (10 µM) for 7 days induces neuroectoderm differentiation (previously described by Vallier et al. 2009). Based upon the intermediate populations namely the neuroectoderm, lateral mesoderm and paraxial/somitic mesoderm, further differentiation to vascular SMCs was done by treating each intermediate population to PDGF-BB (10 ng/mL) and TGF-β1 (2 ng/mL) for 12 additional days. Range of concentrations for SMC differentiation is estimated to be PDGF-BB (5-20 ng/mL) and TGF-β1 (1-5 ng/mL).

Quantitative Polymerase Chain Reaction

Total RNA was extracted with RNeasy Mini kit according to the manufacturer's instructions (QIAGEN). One microgram of RNA was reverse-transcribed with Fermentas Maxima First Strand cDNA Synthesis Kit. Quantitative polymerase chain reaction (QPCR) mixtures were prepared as described (Applied Biosystems SYBR Green PCR Master Mix). QPCR reactions were performed by Applied Biosystems 7500 Fast Real-Time PCR System with technical duplicates and normalized to Porphobilinogen Deaminase (PBGD) in the same run. Error bars on all QPCR graphs represent standard error of mean from three independent biological replicates.

Immunocytochemistry

Detailed immunostaining methods are described in Vallier et al. (2005).

Protein Extraction and Western Blot

To obtain protein extracts, cells were washed twice with ice-cold PBS. Ice-cold RIPA buffer was then added to the cells. Cells were scraped off the culture dishes and transferred into a centrifuge tube. Suspension was agitated by an orbital shaker for 15 minutes to lyse the cells at 4° C. Lysate was centrifuged at 14,000 g in a precooled centrifuge for 15 minutes and the supernatant was kept frozen at −80. Protein concentrations were determined using Thermo Scientific BCA Protein Assay Kit. 20 µg total protein was separated by SDS-PAGE and on stacking gel (30% acrylamide, 1M Tris, 10% SDS, 10% APS, TEMED) then transferred to a nitrocellulose membrane. The membrane was probed with primary antibodies—beta-act in (A1978, Sigma), MYH11 (made in-house), smoothelin (D-10, Santa Cruz) and secondary rabbit-HRP antibody (A0545, Sigma).

Contraction Study and Calcium Flux Measurement

On culture dishes, SMCs were loaded with the calcium-sensitive fluorophore, Fluo-4 AM (2.5 µM; Molecular Probes). Cells were typsinised into single-cell suspension for calcium flux measurement using the CyAn ADP flow cytometer (Packman Coulter). Contraction was induced by treating the cells with carbachol (100 µM). Fluo-4 was excited by the 488 nm laser and the fluorescence emission was measured by the FL1 channel. Cells were analysed just before addition of carbachol, 1 minute and 3 minutes after addition. On the other hand, contraction images of adherent SMCs were acquired by an inverted microscope (Olympus) before and after 10 minutes of carbachol treatment.

Experiments

The protocol used is shown schematically in FIG. 1A, depicting the growth factors used and the duration of the treatment. For the first 36 hours, growth factors used were FLyB10 [FGF2 (20 ng/mL), BMP4 (10 ng/mL) and LY294002 (10 µM)] to induce primitive streak). The subsequent 3.5 days of differentiation specifies mesoderm subtypes. FLy [FGF2 (20 ng/mL) and LY294002 (10 µM)] for somitic mesoderm; FB50 [FGF2 (20 ng/mL) and BMP4 (50 ng/mL)] for lateral mesoderm.

Figure 1B:
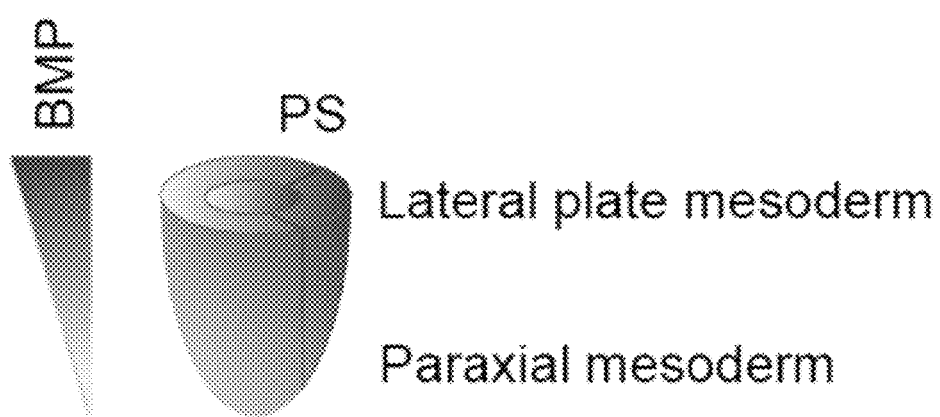
FIG. 1B shows the BMP4 gradient (dark to light green) along the primitive streak (PS, black line).

The BMP4 gradient (dark to light green) along the primitive streak (PS, black line) is shown in FIG. 1B. The locations along the gradient where the Blood and Heart (lateral mesoderm derivatives) or the Muscle (somitic derivatives) progenitors emerge were determined from fate map studies. This provides the rationale behind the optimization of BMP4 concentrations in FIG. 2.

Figure 2:
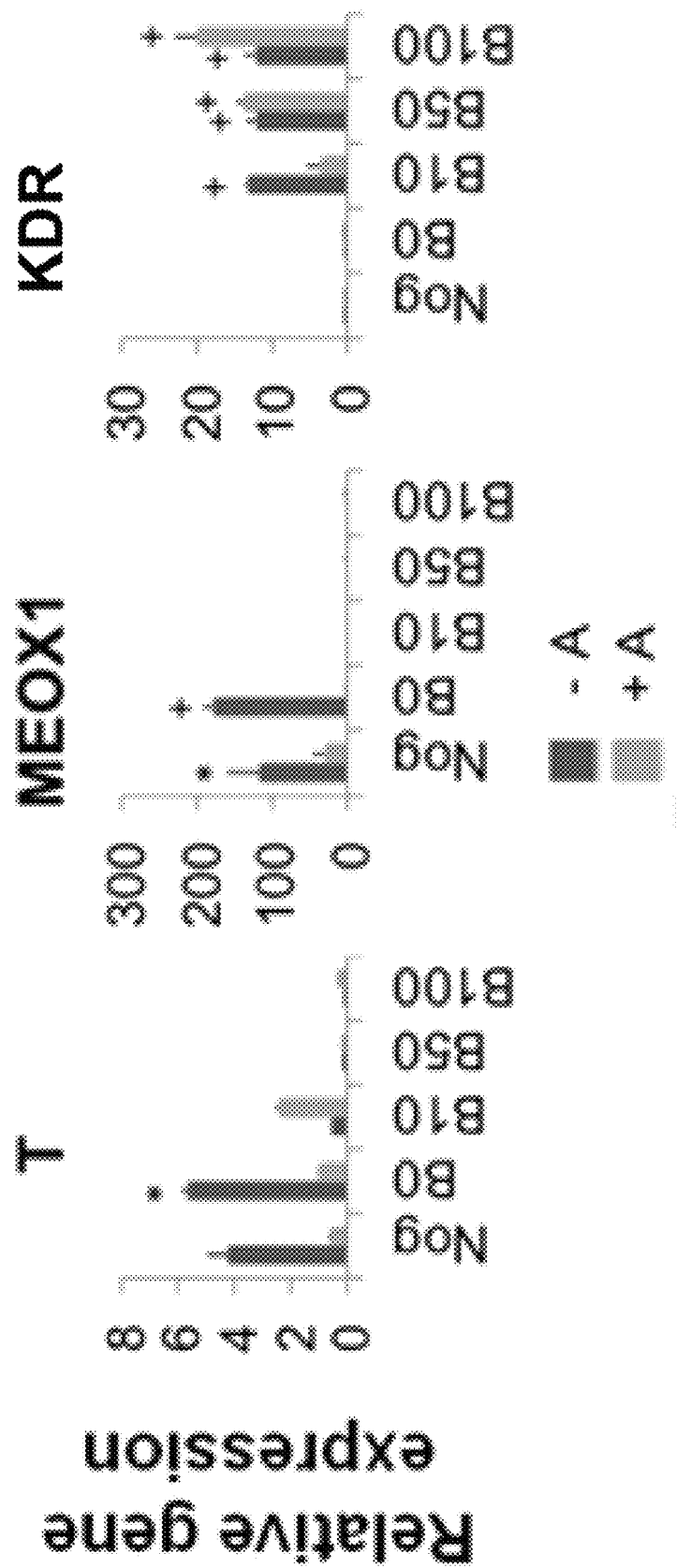

QPCR analysis was performed for Brachyury, MEOX1 and FLK1 in hESCs grown according to the protocol depicted in FIG. 1A and harvested at day 5. The BMP4 gradient tested ranged from 0 ng/mL (Nog) to 100 ng/mL (B100). The bars in FIG. 2 represent the absence or presence of activin A (A) added at 10 ng/ml respectively. Brachyury (T) a primitive streak and mesoderm progenitor marker, was significantly upregulated in the absence of activin A. Likewise, absence of activin A upregulated the paraxial and somatic marker MEOX1, and FLK1, a lateral mesoderm marker. Therefore, absence of activin A promoted mesoderm formation. Expression of FLK1 was increased by BMP4 in a dosage-dependent manner, indicating that high BMP4 enhances lateral mesoderm specification, but inhibited paraxial mesoderm specification. In the presence of activin A (10 ng/ml), BMP4 was also found to promote the expression of the lateral plate marker KDR in a dose-dependent way (from 0 ng/ml to 100 ng/ml, that is, B0 to B100, respectively). Endogenous BMP signalling (B0 condition) was insufficient to promote KDR expression since Noggin, a BMP antagonist, produced the same effect as B0. The absence of activin A did not affect the development of lateral plate mesoderm as KDR was expressed as long as BMP4 was added.

Figure 3:
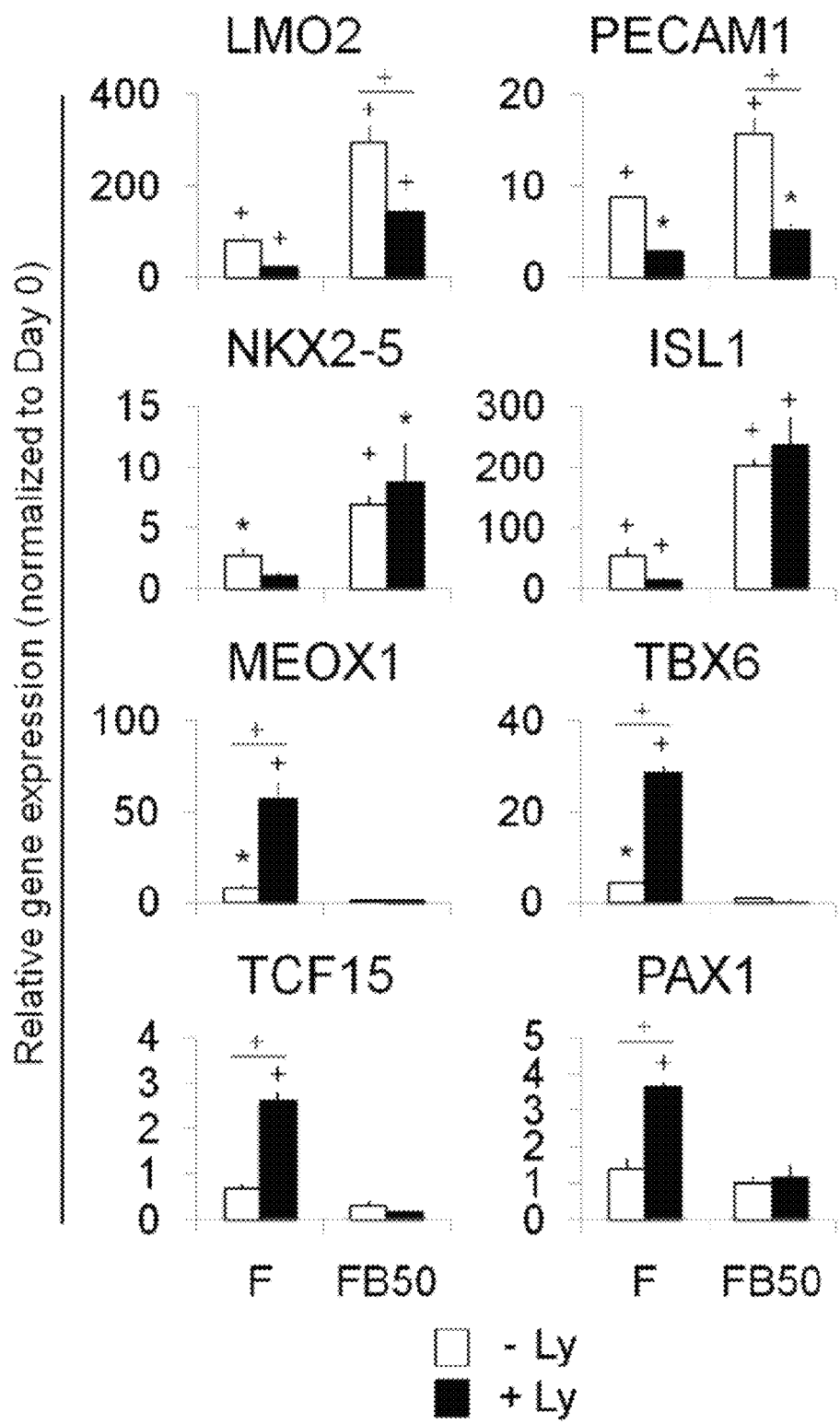

We then evaluated the effect of 10 µM LY294002 (Ly) on mesoderm subtype specification. QPCR analysis of LMO2, CD31, PECAM1, NKX2.5, ISL1, MEOX1, TBX6, TCF15 and PAX1 was performed in hESCs grown for 36 h in FLyB10 and then for 3.5 additional days in F or FB50, with (RH bars) or without (LH bars) by. The absence of Ly was found to upregulate the expressions of various lateral mesoderm markers—LMO2, CD31, NKX2.5 and ISL1 (FIG. 3). On the other hand, the presence of Ly promoted the expressions of somitic markers—MEOX1 and TBX6. In the presence of 20 ng/ml FGF2 (F) alone, Ly significantly promoted the expression of a panel of paraxial markers, MEOX1 (P=0.0051), TBX6 (P=0.0027), TCF15 (P=0.0001) and PAX1 (P=0.0087), versus no LY294002 (FIG. 3). Again, the presence of 50 ng/ml BMP4 (B50) inhibited the expression of all paraxial markers and promoted the expression of lateral plate markers. On the other hand, Ly significantly downregulated the lateral plate markers, LMO2 (P=0.00024 in F, P=0.00002 in FB50); PECAM1 (P=0.0037 in F, P=0.00167 in FB50); NKX2-5 (P=0.0170 in F); and ISL1 (P=0.0132 in F) compared to the no LY294002 condition. Hence, we established the optimal conditions for lateral plate and paraxial mesoderm subspecification to be FB50 and FLy, respectively.

Figure 4:
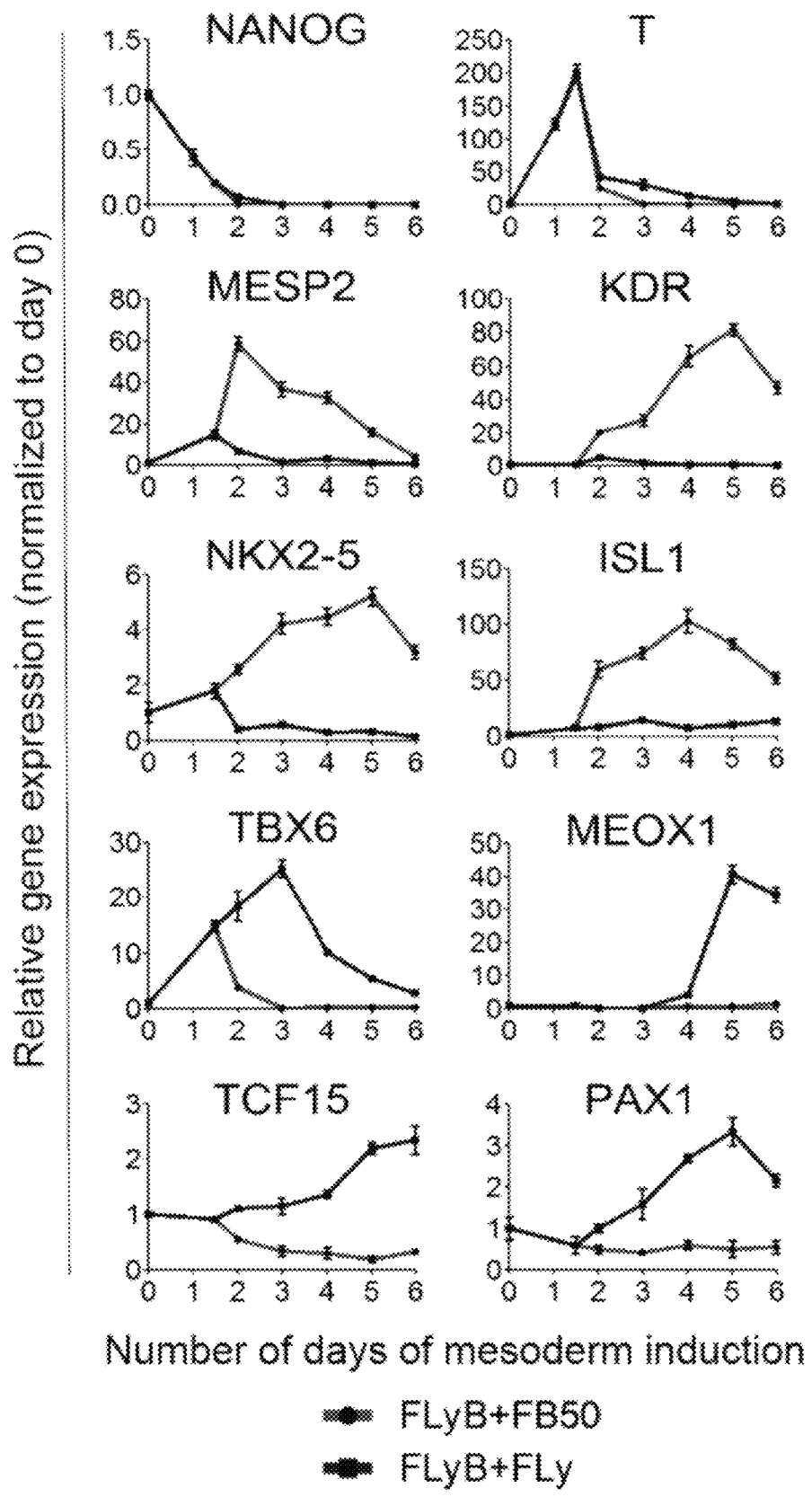

Time-course QPCR was performed to validate the conditions established for mesoderm specification. Both mesoderm subtypes began with a common 36-hour protocol of FLyB10. Thereafter, for lateral and somitic mesoderm development, FB (light line) and FLy (dark line) were employed respectively. NANOG, a pluripotency marker, decreased sharply soon after differentiation began (FIG. 4). Brachyury (T), a primitive streak marker, peaked at 36 hours. After the 36-hour time point, FB (light line) was found to upregulate the lateral mesoderm markers—MESP2, KDR, NKX2.5 and ISL1; while FLy (dark line) upregulated the somitic markers—TBX6, MEOX1, TCF15 and PAX1. Some markers peaked at day 5, indicating that distinctive mesoderm subtypes nave developed by day 5.

Figure 5:
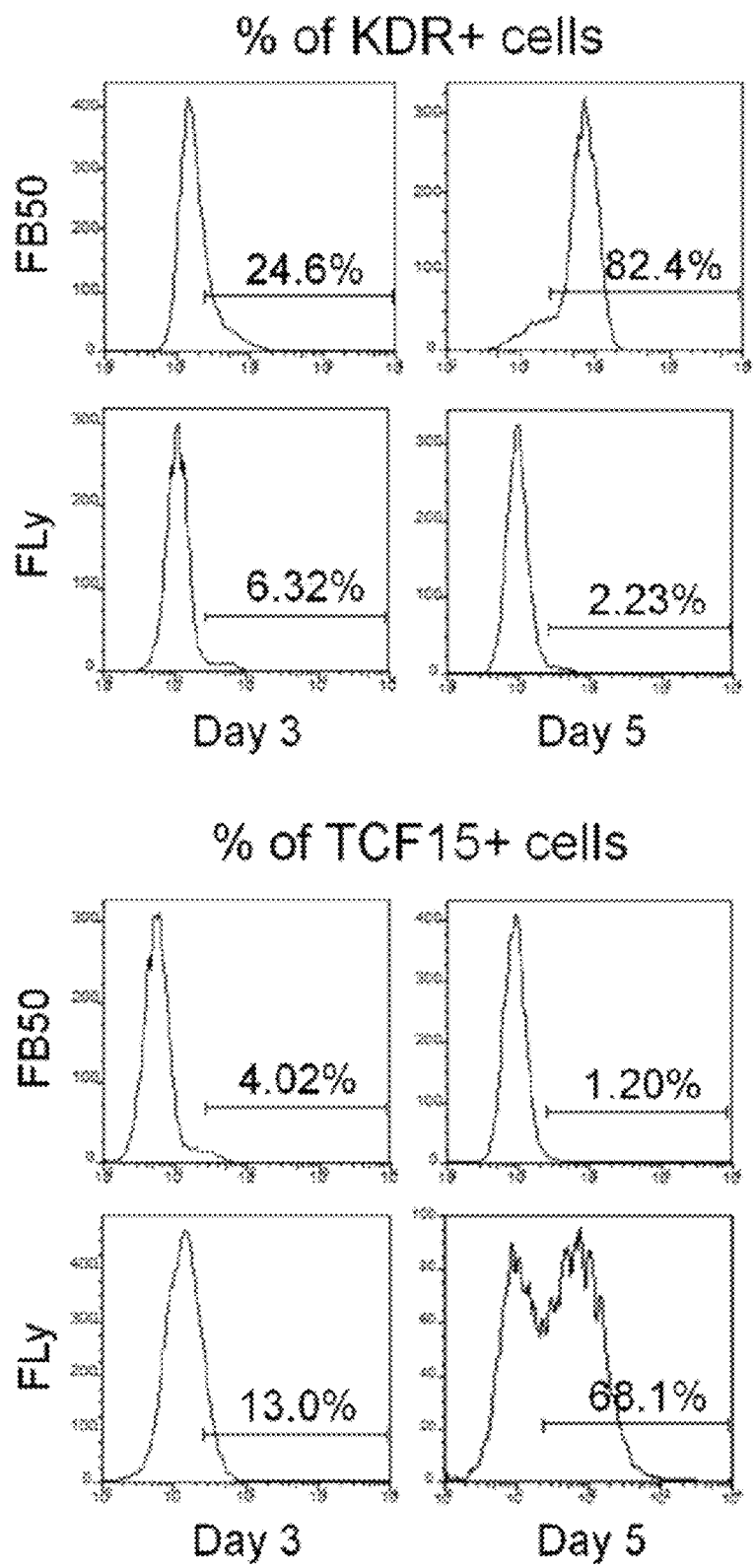

Flow cytometric analysis was performed of the percentage of gene expressing cells for hESCs differentiated for 36 hours in FLyB10 and then in the conditions indicated, for up to day 3 (D3) or day 5 (D5). FB50 was found to promote a majority of KDR-expressing cells (82.4%) FIG. 5 top panels). FLy was found to promote a significant proportion of TCF15-expressing cells (61.3%) by D5 (FIG. 5 bottom panels).

Figure 6A:
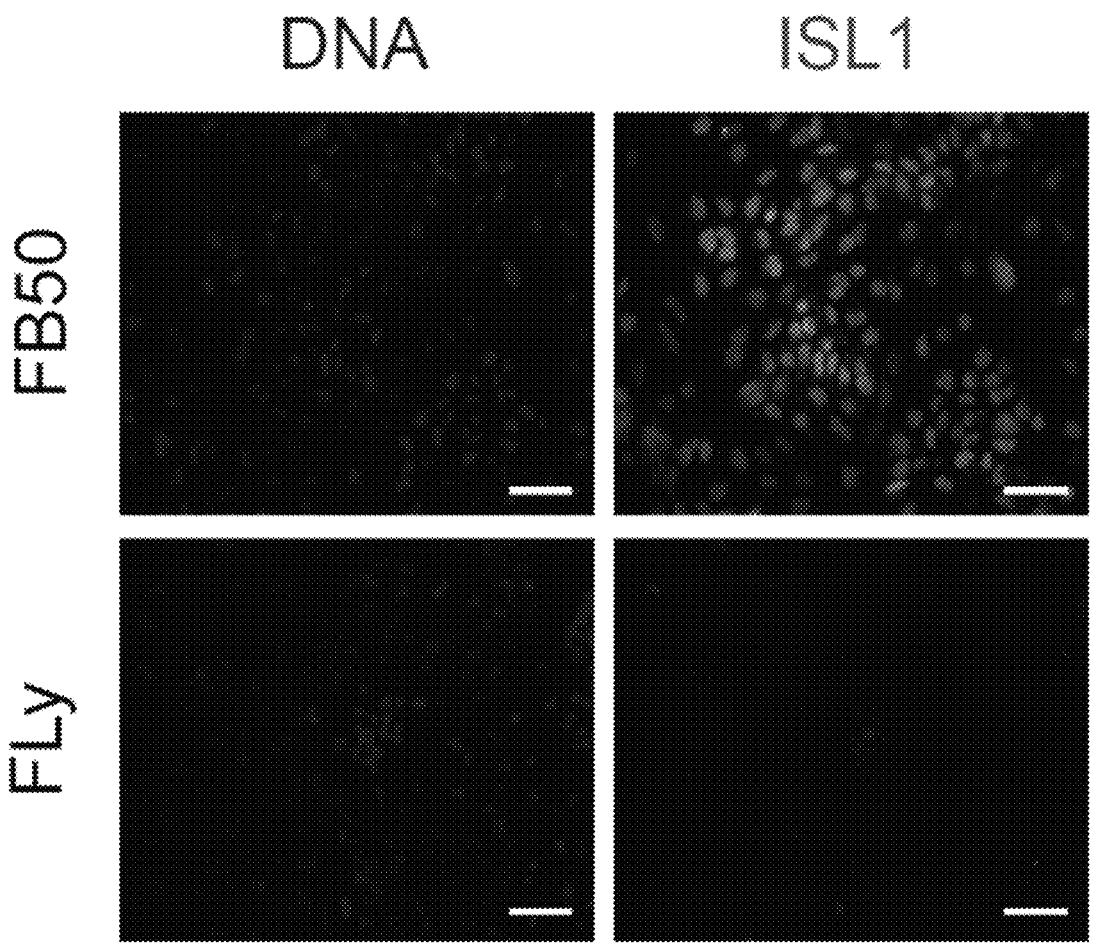
FIG. 6A to 6D show representative fluorescent images for hESCs grown for 36 h in FLyB and then for 3.5 additional days in FLy or FB. Samples were immunostained for mesoderm subtype-specific markers ISL1 (6A), NKX2-5 (6B), TCF15 (6C) and TBX6 (6D). Lateral and paraxial mesoderms were specified using FB50 and Fly, respectively.
Figure 6B:
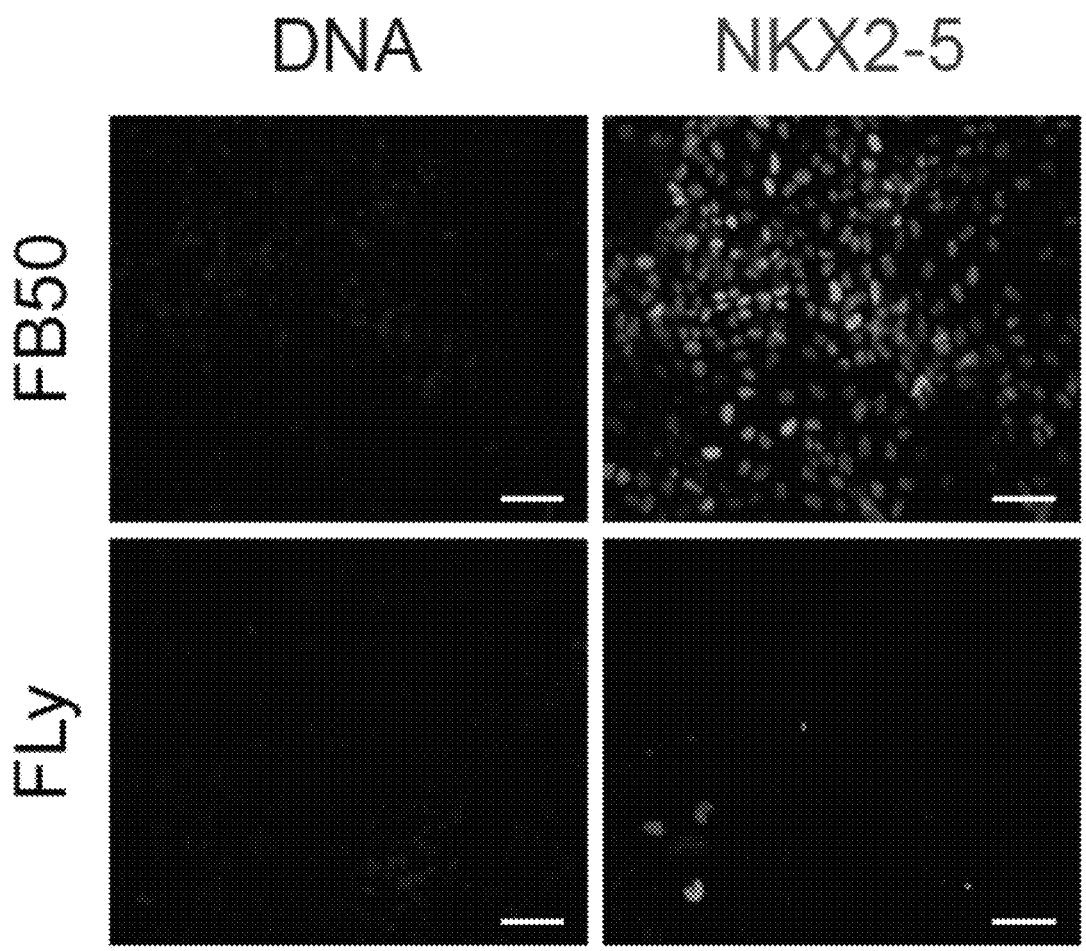
Figure 6C:
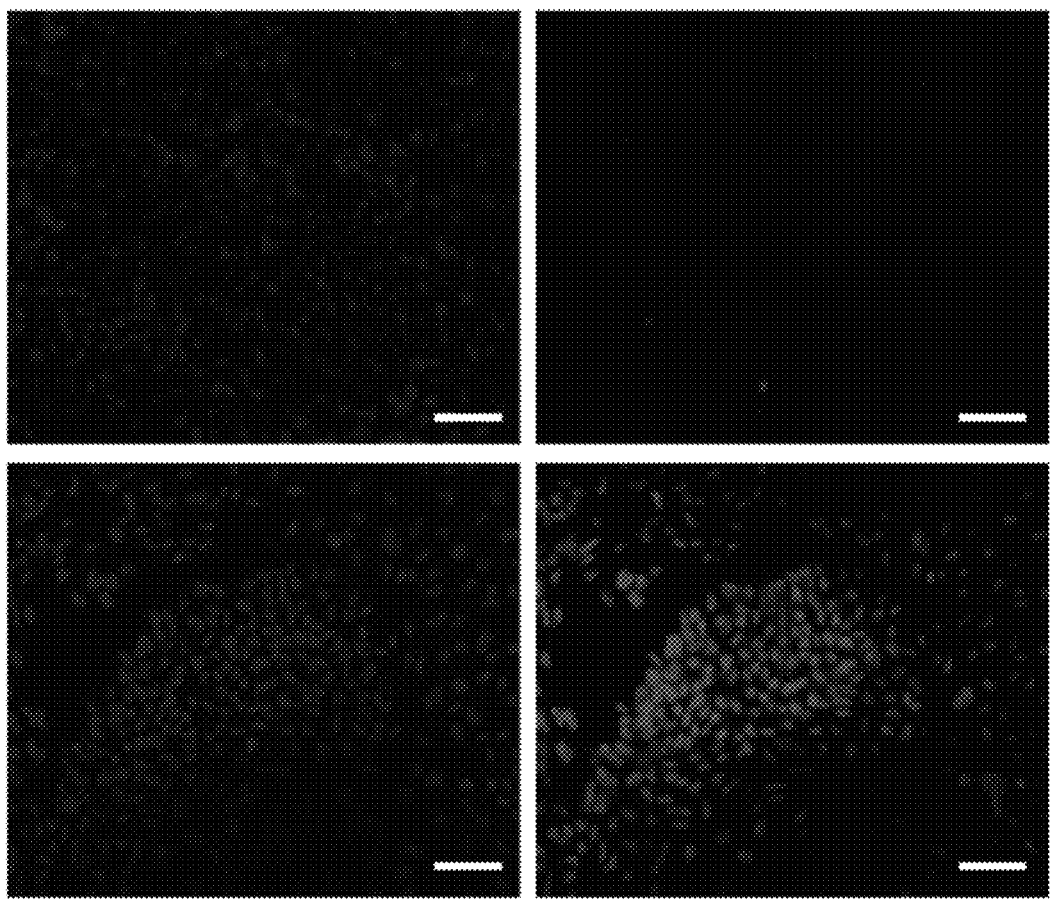
Figure 6D:
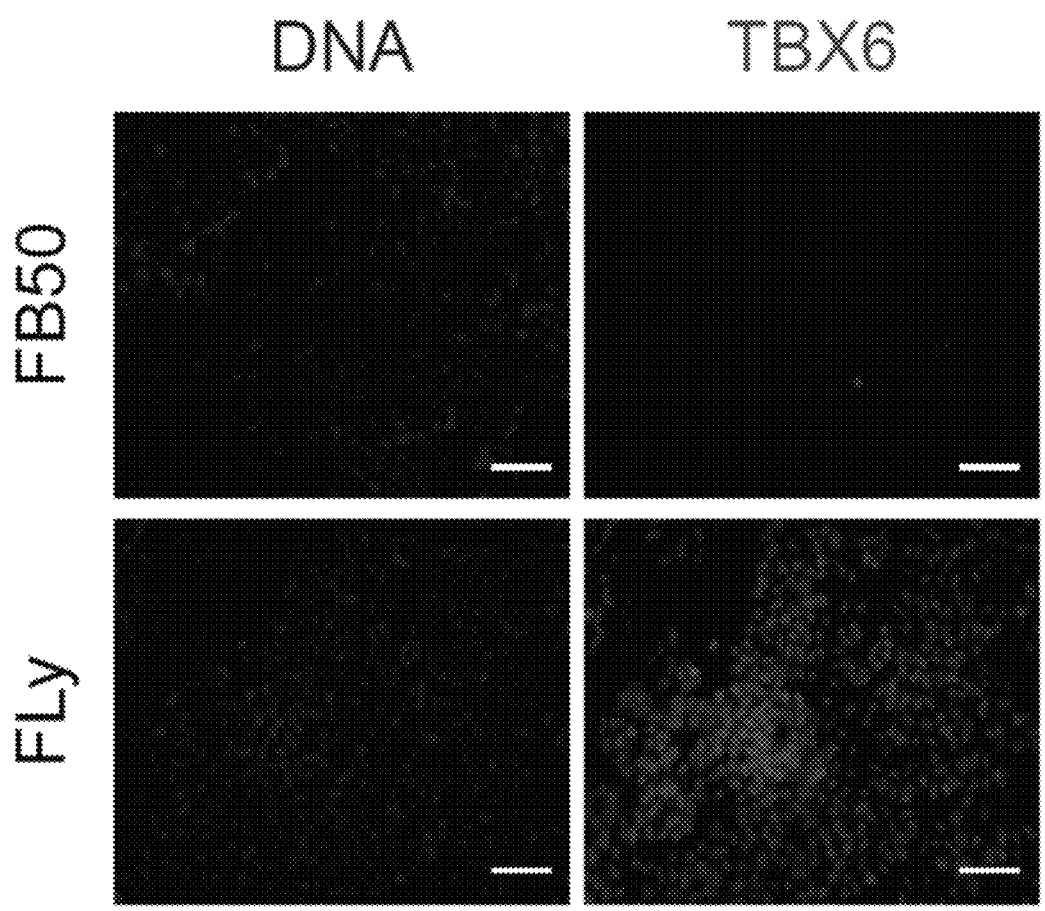

Representative fluorescent images were produced of hESCs grown for 36 h in FLyB and then for 3.5 additional days in FLy or FB, followed by immunostaining for ISL1 (FIG. 6A), NKX2-5 (FIG. 6B), TCF15 (FIG. 6C), TBX6 (FIG. 6D) and MESP2 (not shown). The images show nucleus-focal staining, confirming the localisation of the aforementioned transcription factors.

We tested the effects of PDGF-BB and TGF-β1, as well as two other SMC inducers, retinoic acid (1 µM) and sphingosylphosphorylcholine (5 µM), on our derived intermediate populations, namely neuroectoderm, lateral plate mesoderm and paraxial mesoderm. Treatment with a combination of the two best inducers, PDGF-BB (10 ng/ml) and TGF-β1 (2 ng/ml) (PT treatment), promoted the highest expression of the SMC marker MYH11 from all the intermediate populations.

Figure 7:
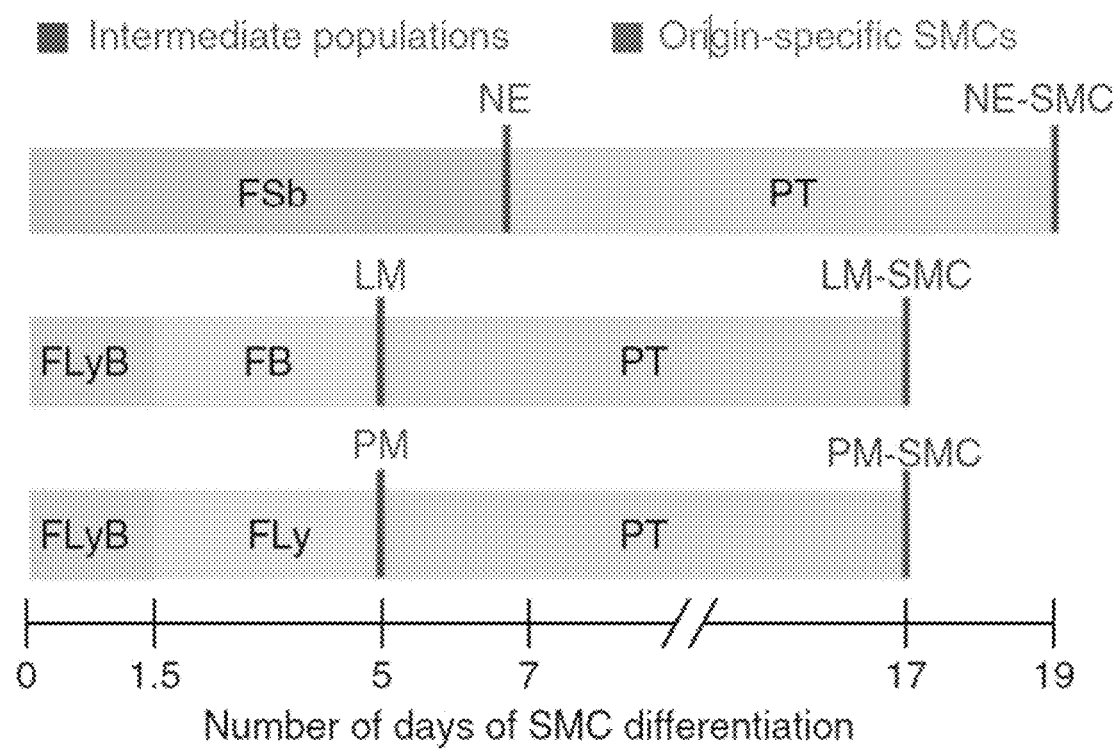
FIG. 7 shows a schematic which outlines a step-wise differentiation protocol for deriving origin-specific SMCs. FLyB+FB and FLyB+Fly generate the lateral plate mesoderm (LM) and paraxial mesoderm (PM), respectively. HPSCs were treated with FGF2+SB431542 (FSb) for 7 d to induce neuroectoderm (NE) differentiation. For further differentiation into vascular SMCs, each intermediate population was subjected to PDGF-BB+TGF-β1 (FT) for 12 additional days. The SMC subtypes, namely the neuroectoderm-derived SMCs, lateral mesoderm-derived SMCs, paraxial mesoderm-derived SMCs are abbreviated as NE-SMC, LM-SMC and PH-SMC, respectively.

The step-wise differentiation protocol for deriving origin-specific SMCs is shown schematically in FIG. 7. FLyB-FB and FLyB-Fly were used to generate the lateral and somitic mesoderm respectively. Treatment of hESCs with FSb [FGF2 (20 ng/mL) and SB431542 (10 µM)] for 7 days induces neuroectoderm differentiation (Vallier et al. 2009). The three intermediate populations (neuroectoderm, lateral mesoderm and somitic mesoderm) are referred to as NE, LM and SM. For further differentiation to vascular SMCs, each intermediate population was subjected to PT [PDGF-BB (10 ng/mL) and TGF-β1 (2 ng/mL)] for 12 additional days. The resulting origin-specific SMCs (neuroectoderm-derived SMC, lateral mesoderm-derived SMC, and somitic mesoderm-derived SMC) are abbreviated as NE-SMC, LM-SMC and SM-SMC respectively.

Figure 8:
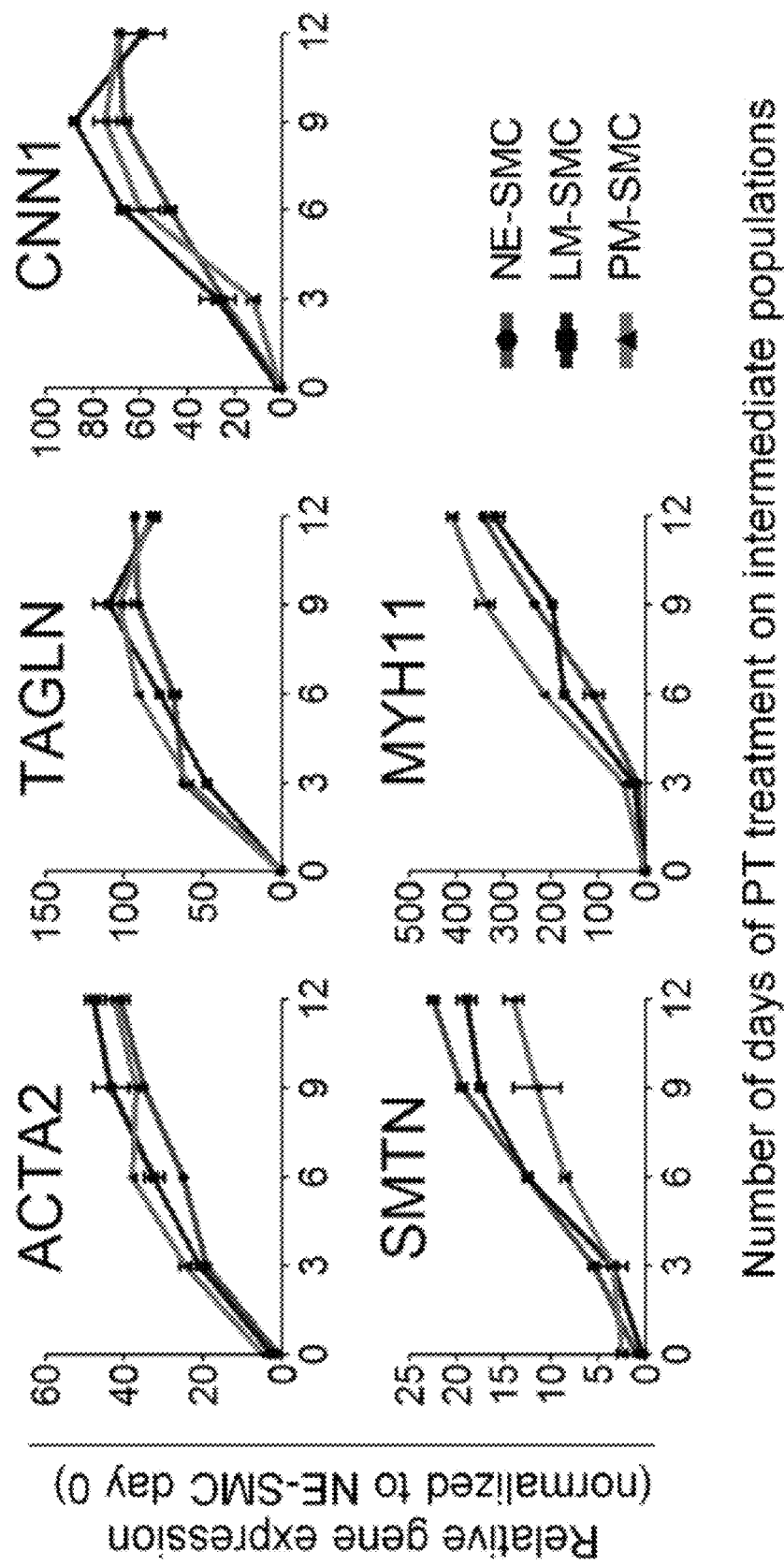
FIG. 8 shows time-course gene expression analysis of vascular SMC markers during differentiation on three intermediate populations using qRT-PCR.

Time-course gene expression analysis of vascular SMC markers ACTA2, TAGLN, CNN1, SMTN and MYH11 during differentiation showed that expression of all five markers peaked between day 9 and day 12 after PT treatment on the intermediate populations (FIG. 8), with upregulation of early SMC markers (ACTA2, TAGLN and CNN1) preceding the late markers (SMTN and MYH11). The derived SMCs after 12 d of PT treatment demonstrated similar gene expression levels to those of the positive control, human aortic SMCs. Flow cytometric analysis correlated with the gene expression data, documenting an increment in the percentage of cells positive for both MYH11 and ACTA2 over this period. Twelve days of PT treatment culminated in >80% MYH11+ ACTA2+ cells generated from the three intermediate populations, similar to human aortic SMCs.

Figure 9:
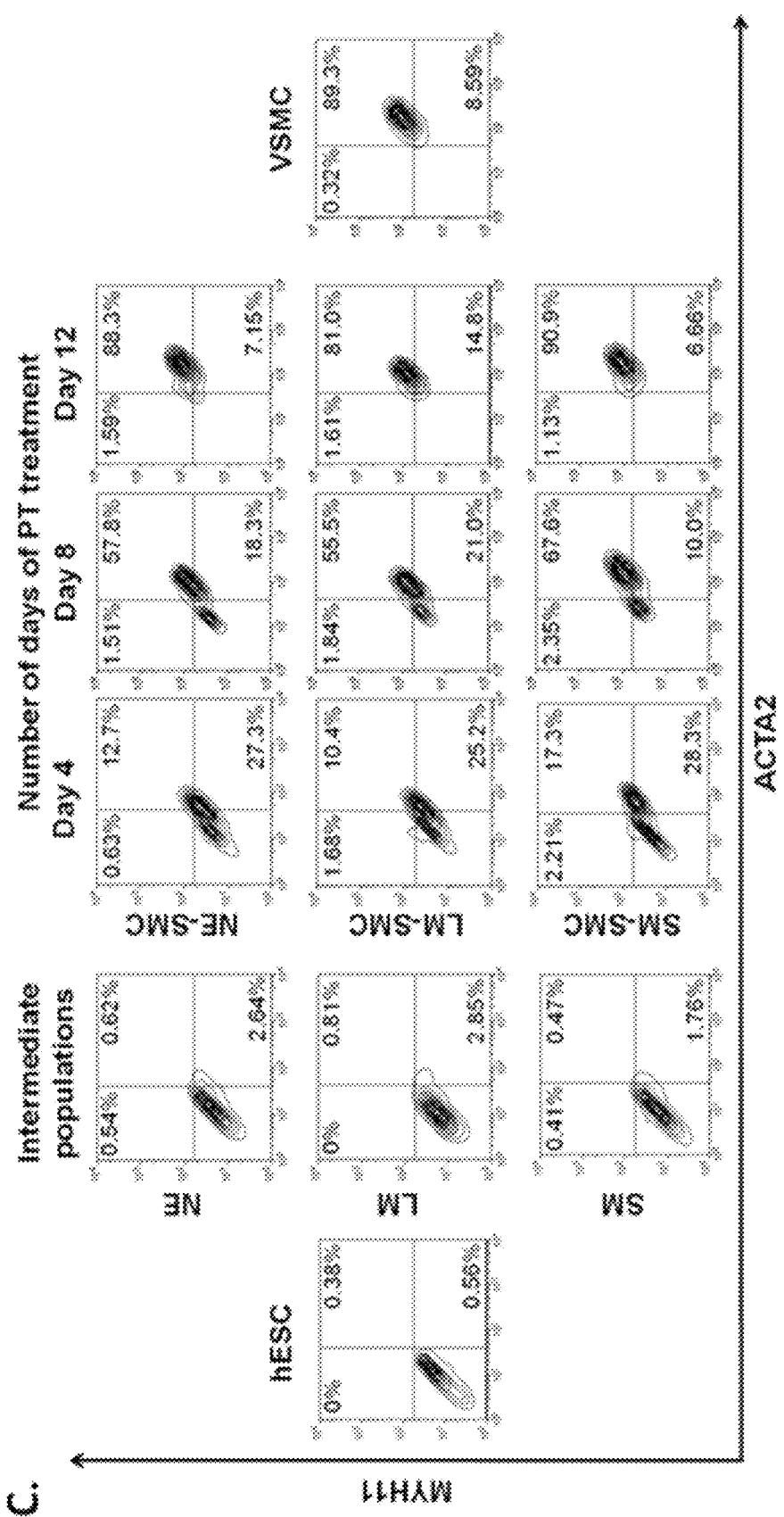
FIG. 9 shows flow cytometric analysis of the percentage of MYH11/ACTA2 doubly expressing cells after SMC differentiation.

Flow cytometric analysis of the percentage of MYH11/ACTA2 doubly expressing cells was performed (FIG. 9). The percentage of positive cells increased with the number of days of PT treatment. By day 12, more than 80% of the cells from each lineage were doubly positive. VSMC, human aortic SMC, was used as a positive control, showing comparable result with the origin-specific SMCs. The highly efficient process to derive origin-specific SMCs was reproducible in two hESC lines (H1 and H9) and a wild-type iPSC line.

Because vascular SMCs arise more precisely from the neural crest, a descendant of neuroectoderm, we investigated whether there was transient formation of neural crest during neuroectoderm to SMC differentiation. Indeed, expression of BMP4 and BMP7, required for neural crest differentiation, increased after PT treatment, before the peak expression of neural crest markers SNAI1 and SNAI2 at day 3. The other neural crest markers PAX3 and SOX10 displayed higher expression during the first 2 d of PT treatment as BMP expression levels increased. We reasoned that the spontaneous formation of neural crest could be due to the endogenous production of BMP4 and BMP7. Microarray analysis was carried out to characterize the hPSC-derived SMCs. Differentiated SMCs demonstrated downregulation of pluripotency genes, accompanied by upregulation of vascular SMC genes. Furthermore, genes relating to neuronal, cardiac/endothelial/hematopoietic and skeletal muscle lineages, which are the other potential derivatives of neuroectoderm, lateral plate mesoderm and paraxial mesoderm, respectively, were repressed.

Figure 10:
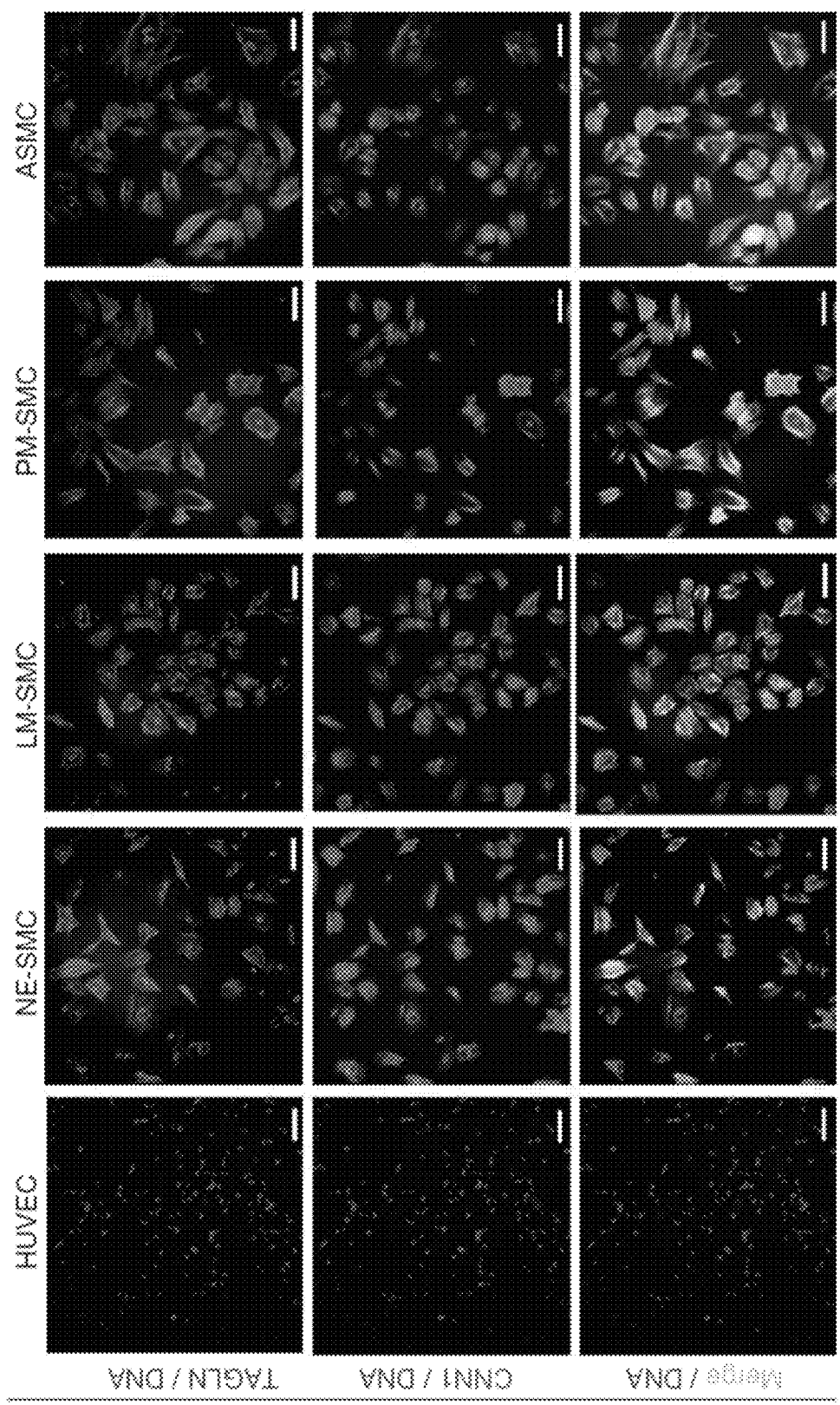
FIG. 10 shows immunofluorescent staining of the SMC markers, CNN1 and TAGLN, on the origin-specific SMCs after 12 days of PDGF-BB and TGF-β1 (PT) treatment.

Immunofluorescent staining of SMC markers CNN1 and TAGLN was performed on the origin-specific SMCs after 12 days of PT treatment. HUVEC, human umbilical vein endothelial cell, was used as a negative control, while VSMC was used as a positive control. The majority of the derived SMCs were found to be stained doubly positive (FIG. 10).

Figure 11:
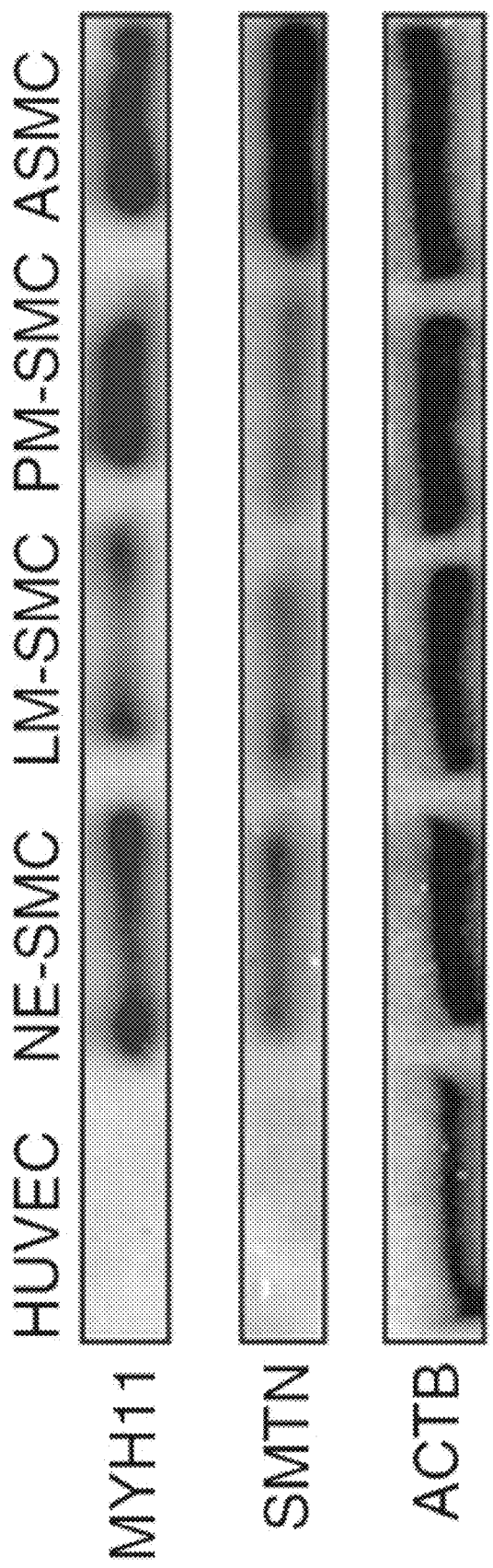
FIG. 11 shows a western blot demonstrating the presence of mature SMC proteins, MYH11 and SMTN, in hPSC derived SMCs and human aortic SMCs, but not HUVEC cells.

The presence of mature SMC proteins, MYH11 and SMTN, in the origin-specific SMCs was demonstrated by western blot (FIG. 11). These proteins were absent in HUVECs.

Figure 12:
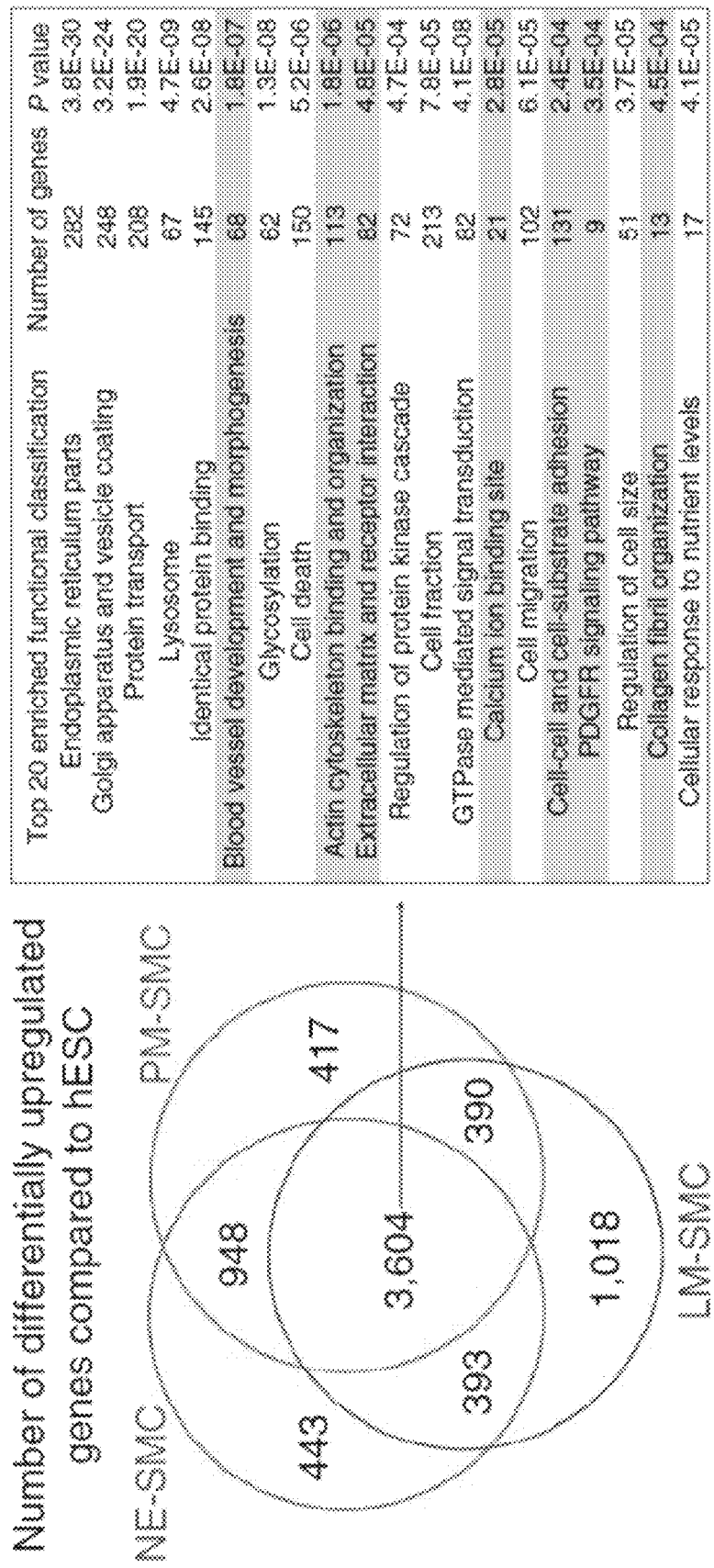
FIG. 12 shows a Venn diagram representing subsets of genes that were differentially upregulated in the SMC subtypes compared to hESC (false-discovery rate, 0.1%). The commonly upregulated 3,604 genes were analyzed using the functional annotation clustering from DAVID bioinformatics resources. Among the top 20 highly enriched groups, functional characteristics pertaining to vascular SMCs are highlighted.

Despite the divergent initial differentiation routes, microarray analysis revealed that the three types of derived SMCs shared many genes (3,604) differentially upregulated compared to hESCs (false-discovery rate, 0.1%) (FIG. 12). Among the highly enriched, functional classifications of the 3,604 genes, there were the classical SMC functionality categories, such as blood vessel morphogenesis, extracellular matrix (ECM) interaction and actin cytoskeleton organization (FIG. 12). Alternatively, the significantly enriched functional classifications of the non-overlapping gene subsets revealed inherent differences among SMC subtypes. For example in neuroectoderm (NE)-SMC, there were categories related to myelination and synaptic transmission, both of which are neuronal characteristics, supporting the common neuroectoderm origin of NE-SMC and neurons. In particular, lateral plate mesoderm (LM)-SMC was highly enriched in genes promoting cell migration and consistent with this enrichment, these cells also displayed the greatest migration in a scratch assay.

Figure 13:
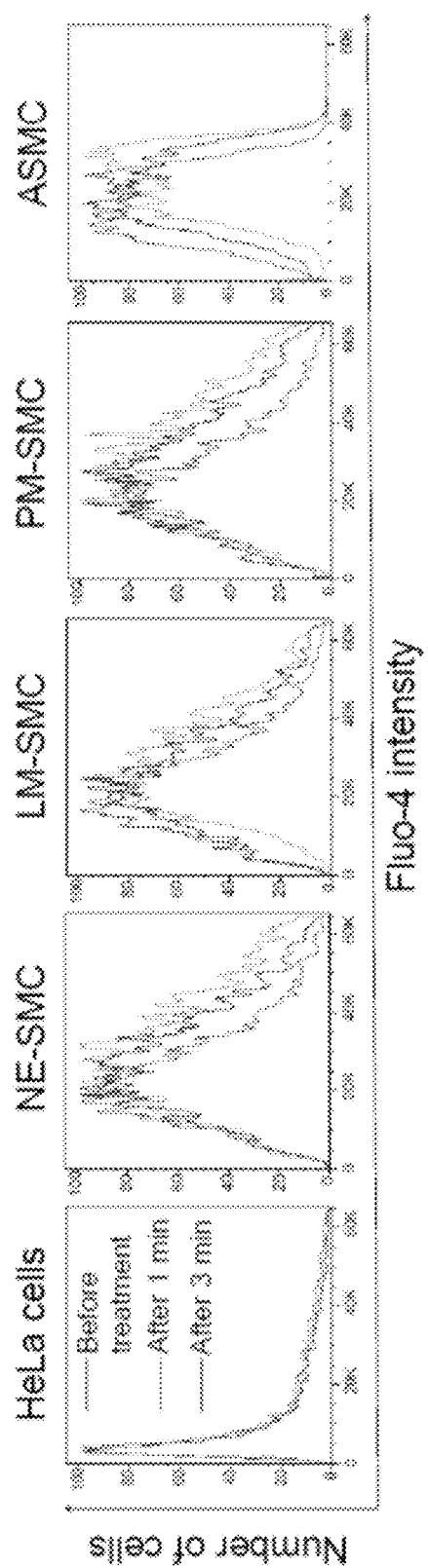
FIG. 13 shows calcium signalling in NE-SMC, LM-SMC, SM-SMC, negative control Hela cells and positive control aortic SMCs in response to carbachol.

Changes of calcium signalling in cells are indicative of their contractile properties in response to carbachol, a potent vasoconstrictor. The origin-specific SMCs were loaded with fluo-4, a calcium-sensitive dye, prior to the addition of carbachol (FIG. 13) and fluorescent emission from the fluo-4 measured over time (T) after the addition of carbachol to the origin-specific SMCs. Hela cells were used as negative control. The origin-specific SMCs were found to display a transient increase in fluo-4 intensity after 1 minute, indicating increased calcium signalling in response to carbachol.

Figure 14:
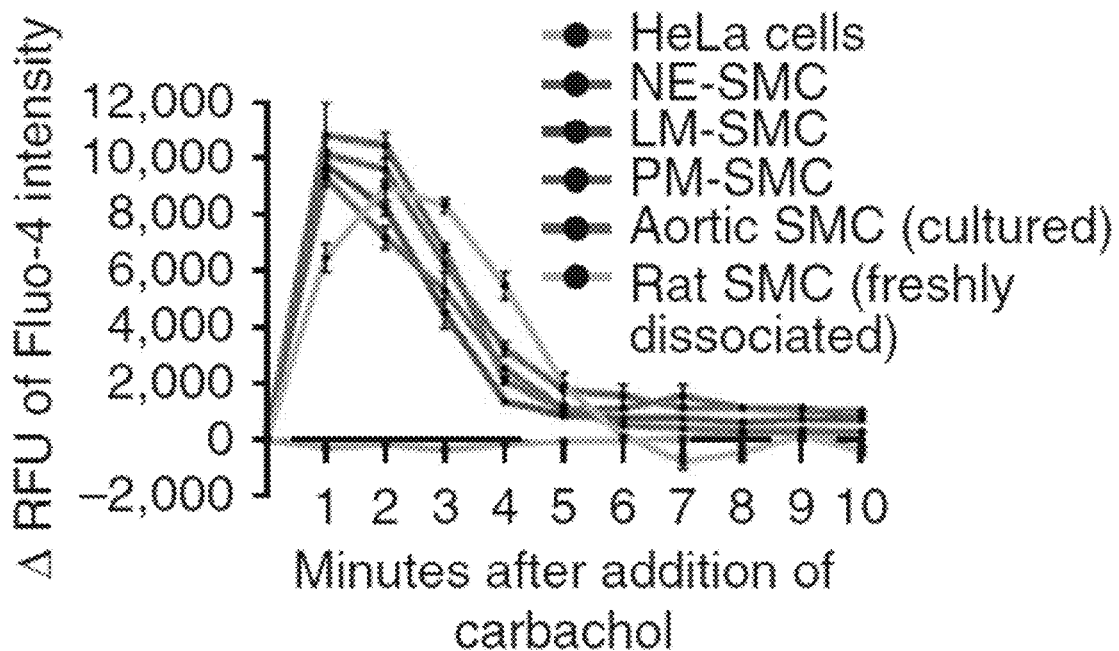
FIG. 14 shows changes in the relative fluorescence unit ($\Delta$ RFU) of Fluo-4 loaded cells as monitored by flow cytometry over 10 min after the addition of carbachol, an inducer of contraction.
Figure 15:
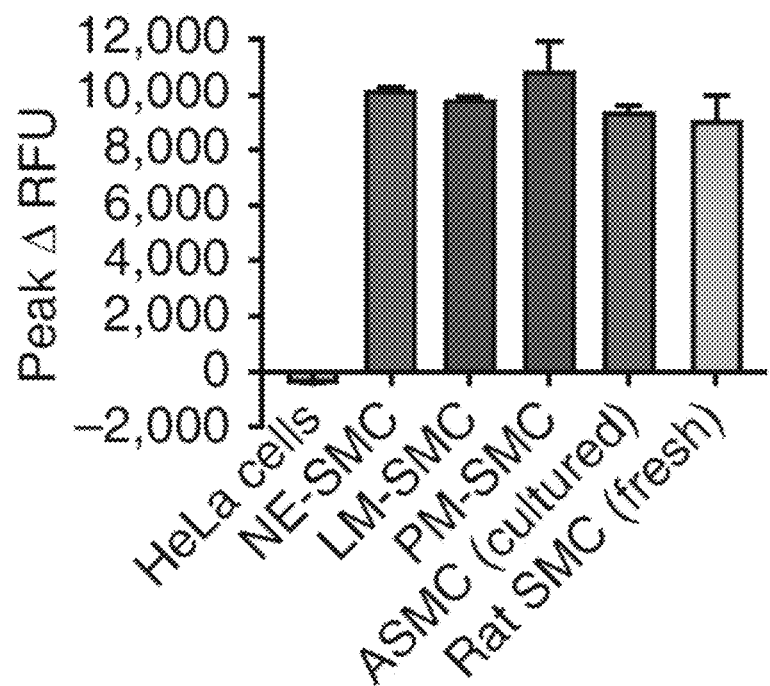
FIG. 15 shows peak $\Delta$ RFU of Fluo-4 intensity in response to carbachol in the derived SMCs and the SMC controls (n=3).

To assess SMC contractile potential, we initially performed immunostaining for vinculin and phalloidin staining for actin filaments, Well-developed focal adhesion complexes were detected in all three SMC subtypes. The cells were then preloaded with a calcium-sensitive dye, Fluo-4. Carbachol (100 µM) stimulated an increase in Fluo-4 fluorescence intensity in the derived SMCs within 1 min of treatment (FIG. 14), indicating increased intracellular calcium flux. After 2 min of treatment, Fluo-4 intensity decreased, approaching original basal levels by 5 min. The same trend was observed in the positive control, human aortic SMCs but not in the negative control HeLa cells. Freshly dissociated rat aortic SMCs served as the optimal physiological control and demonstrated prolonged increase in intracellular calcium over the first 3 min. The derived SMCs exhibited similar peak fluorescence responses to both the cultured and freshly dissociated SMC controls (FIG. 15).

Figure 16A:
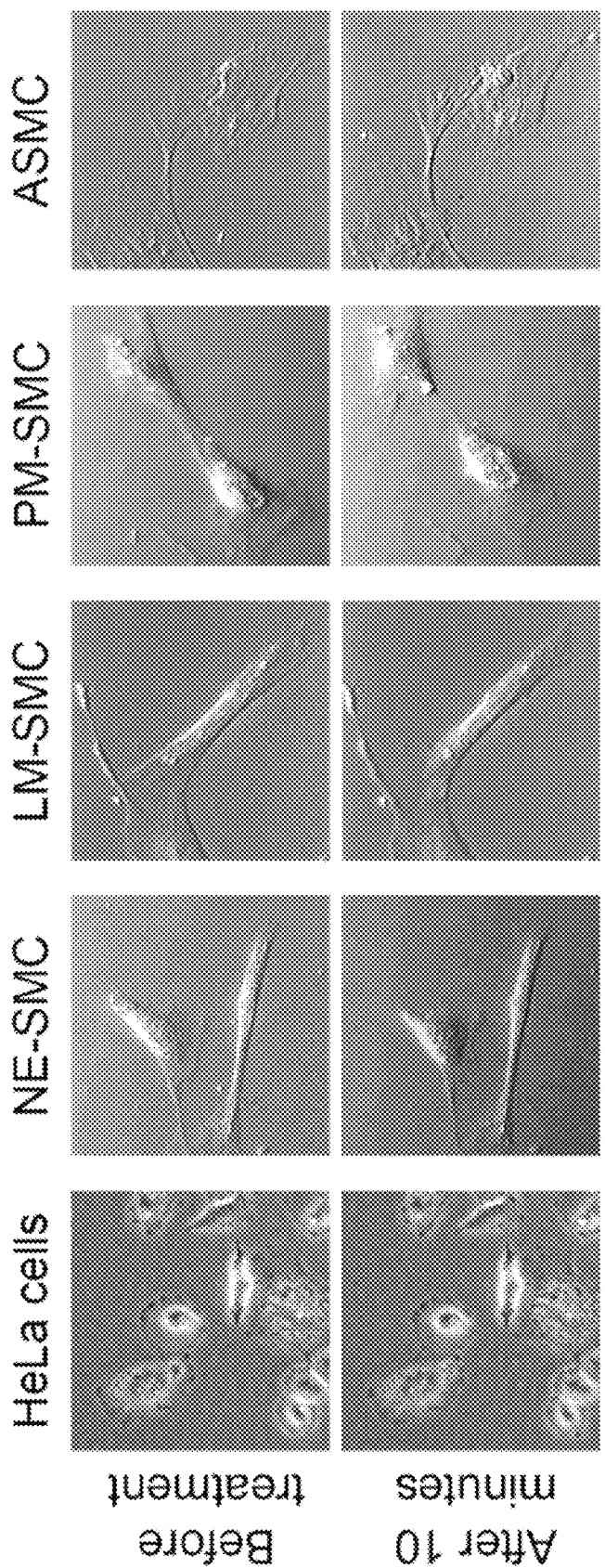
FIG. 16A shows phase contrast microscopic images of the contraction of the origin-specific SMCs and human aortic SMCs 10 minutes after the addition of carbachol.
Figure 16B:
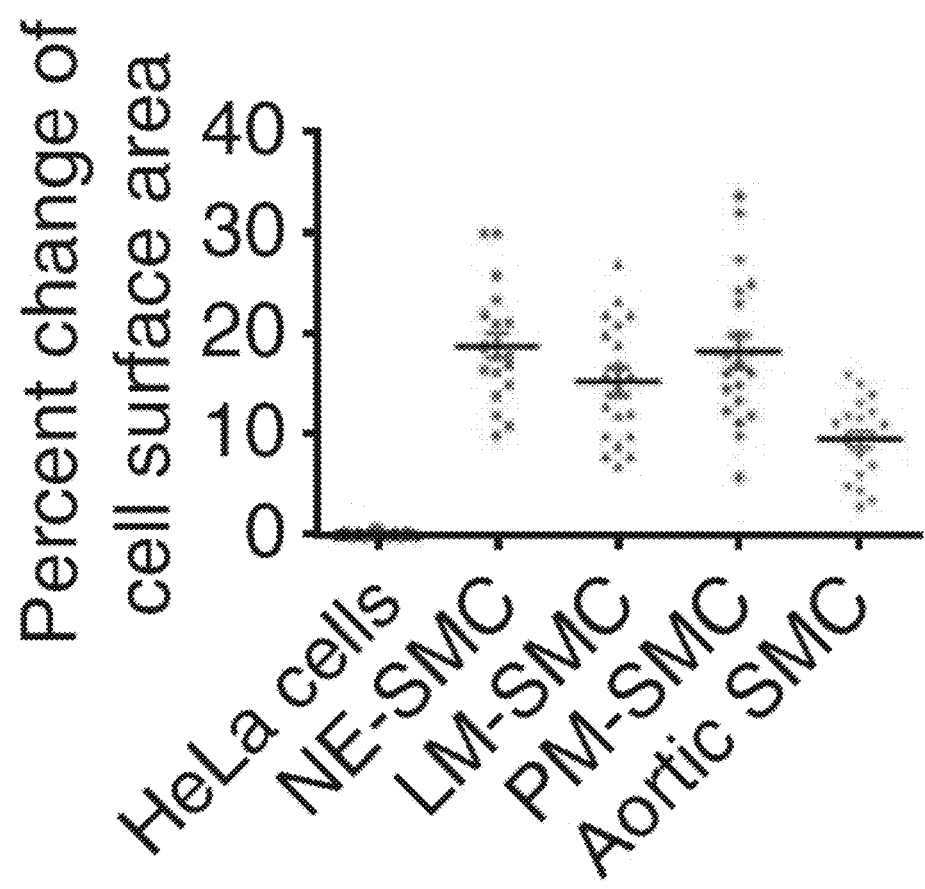
FIG. 16B shows the percentage change in surface area for origin-specific SMCs and human aortic SMCs exposed to carbachol. There was a 10-20% change of surface area in contracting cells of all SMCs except the negative control HeLa cells (n=20).

The contraction of the origin-specific SMCs 10 minutes after the addition of carbachol was confirmed by phase contrast microscopy (FIG. 16A), which showed that our SMCs and human aortic SMCs contracted in a tonic fashion during the 10 min of carbachol treatment, consistent with the sustained contraction usually manifested by vascular SMCs in controlling vessel tone. Contracting cells exhibited a 10-20% change of cell surface area (n=20) (FIG. 16B). These results confirm the presence of functional origin-specific SMCs. Over 50% and 20% of all derived SMCs contracted upon carbachol and angiotensin II treatments, respectively. Paraxial mesoderm (PM)-SMC demonstrated a significantly higher percentage of contractile cells than other SMC subtypes (P=0.036 versus NE-SMC in carbachol; P=0.027 versus NE-SMC and P=0.013 versus LM-SMC in angiotensin II).

Figure 17:
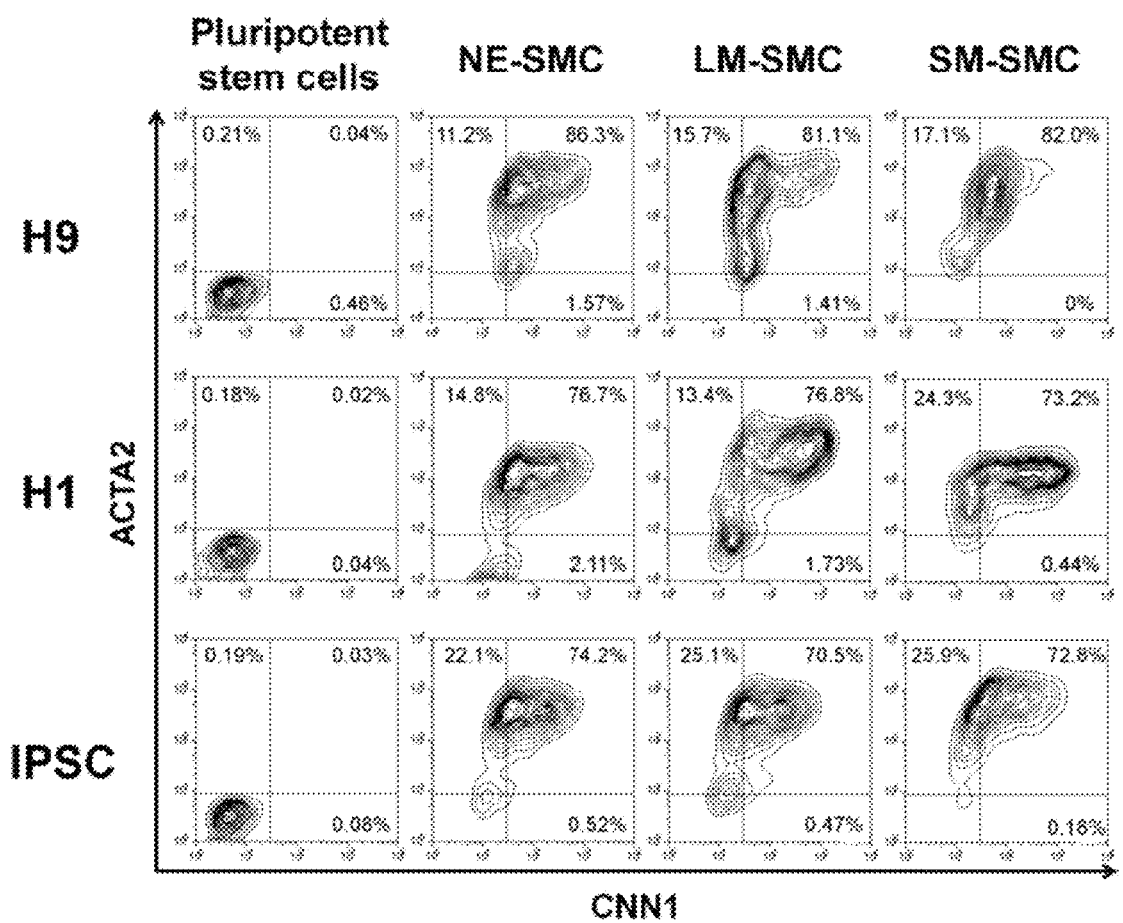
FIG. 17 shows flow cytometric analysis of the percentage of CNN1/ACTA2 doubly expressing cells after SMC differentiation of induced pluripotent stem cells (IPSC) or two different human ESC lines (H1 & H9).

The percentage of CNN1/ACTA2 doubly expressing cells after SMC differentiation was analysed by flow cytometry (FIG. 17). The data show that the differentiation protocol that has been established using the hESC line H9 was also reproducible on another cell line H1, as well as an IPSC.

Figure 18:
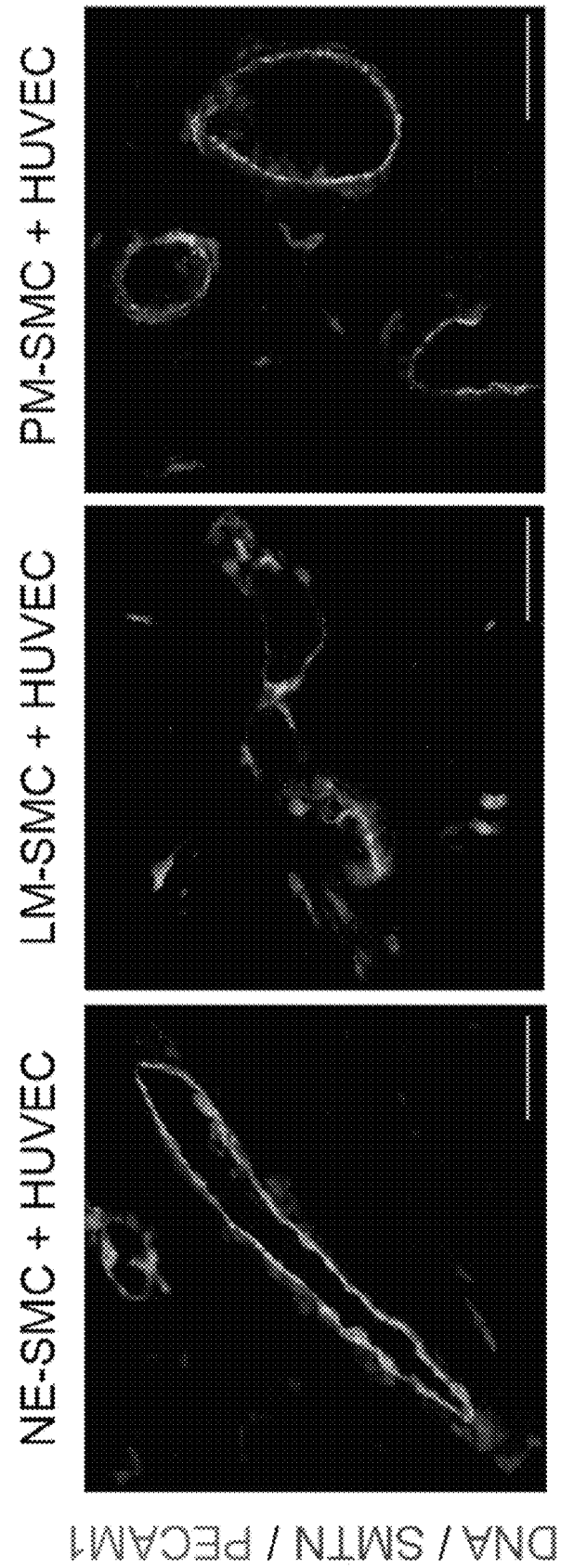
FIG. 18 shows immune-staining of histological sections of matrigel plugs harvested 2 weeks after the subcutaneous implantation of hPSC-derived SMCs and HUVECs (1:2) and double immunostained with human-specific SMTN and PECAM1 antibodies.
Figure 19:
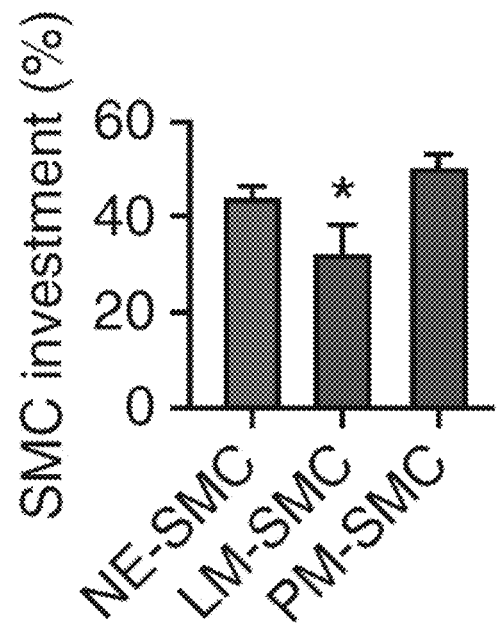
FIG. 19 shows SMC investment quantified based on the relative length of endothelial luminal structures that had SMC coverage in ten different optical fields of the sections shown in FIG. 18. Statistical test was performed by ANOVA (*, P<0.05). Scale bars, 50 μm. Data represent means±s.e.m.

To determine whether the hPSC-derived SMCs could contribute to vessel formation in vivo, we implanted Matrigel plugs with our SMCs and HUVECs (ratio 1:2) subcutaneously into immunodeficient mice for 2 weeks. Sections were immunostained using human-specific SMTN and PECAM1 antibodies. Luminal structures composed of HUVECs (PECAM1+) were observed (FIGS. 18 and 19). HPSC-derived SMCs (SMTN+) were recruited to peri-endothelial regions, reminiscent of their biological niche. There was 30-45% SMC coverage around the endothelial vessel structures with LM-SMCs displaying lower coverage levels (31.5±5.1%) than the other two groups (43.1±2.6% NE-SMC and 48.9±3.1% PM-SMC).

These results confirmed that the in vitro-derived SMCs were functional.

Figure 20:
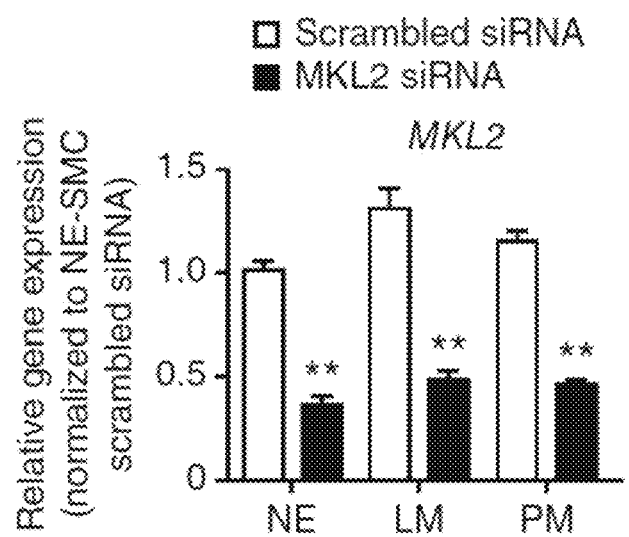
Figure 21:
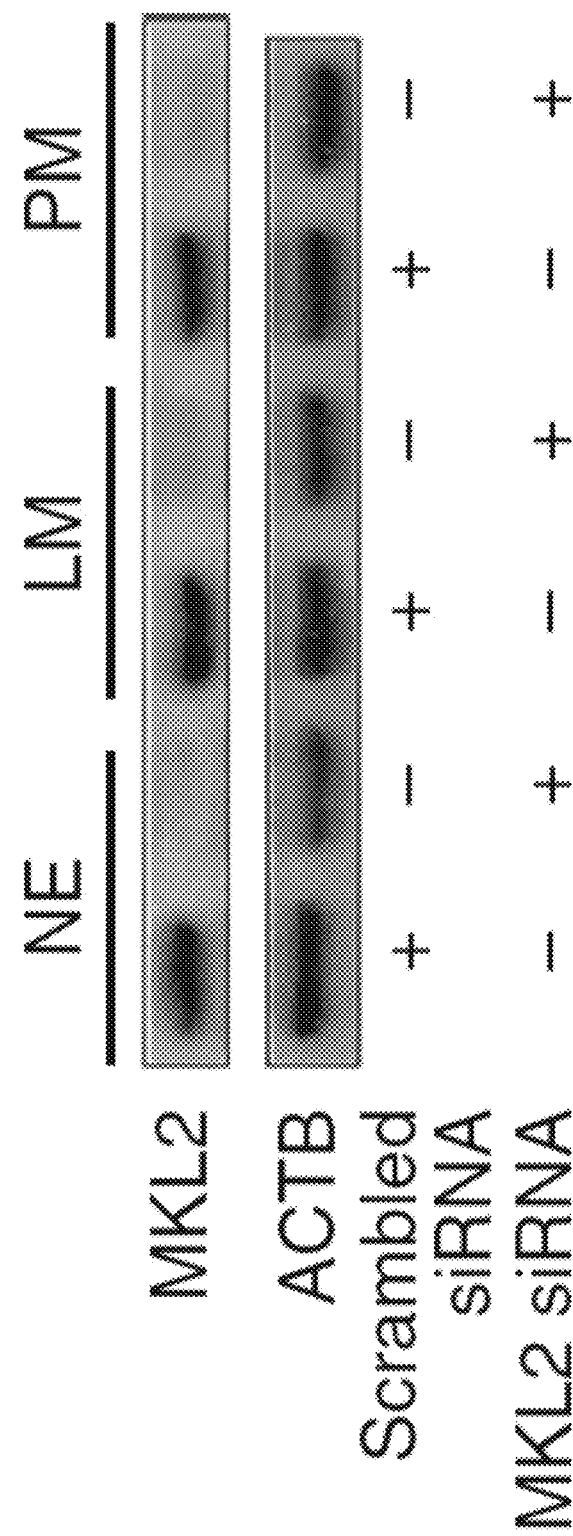
Figure 22:
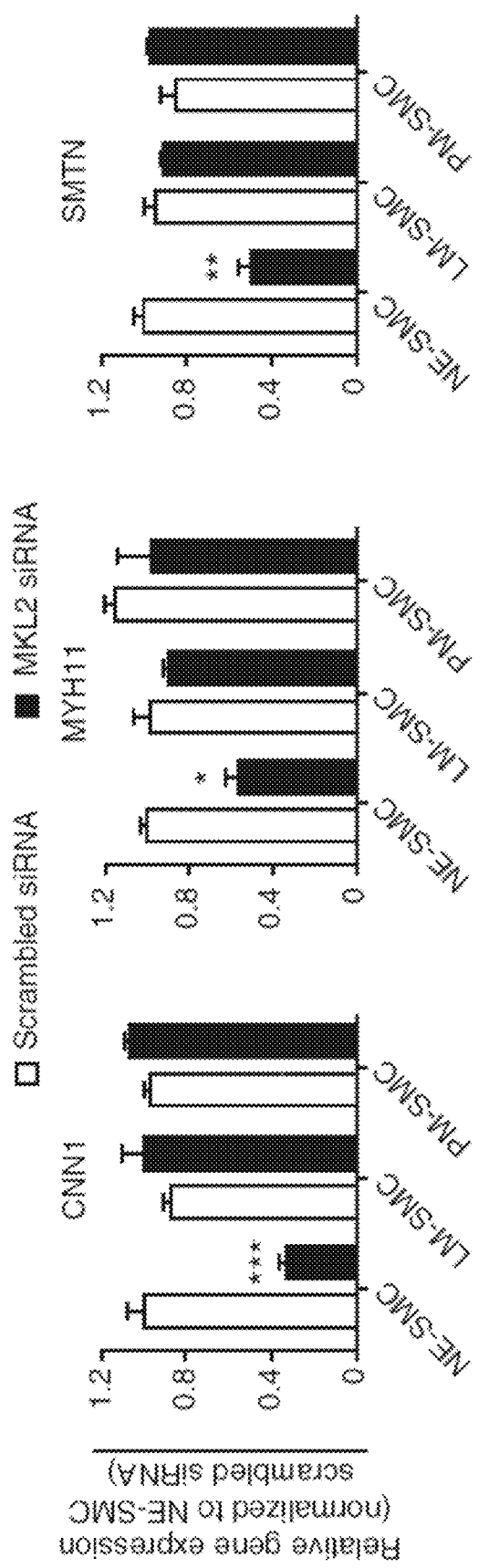
Figure 23:
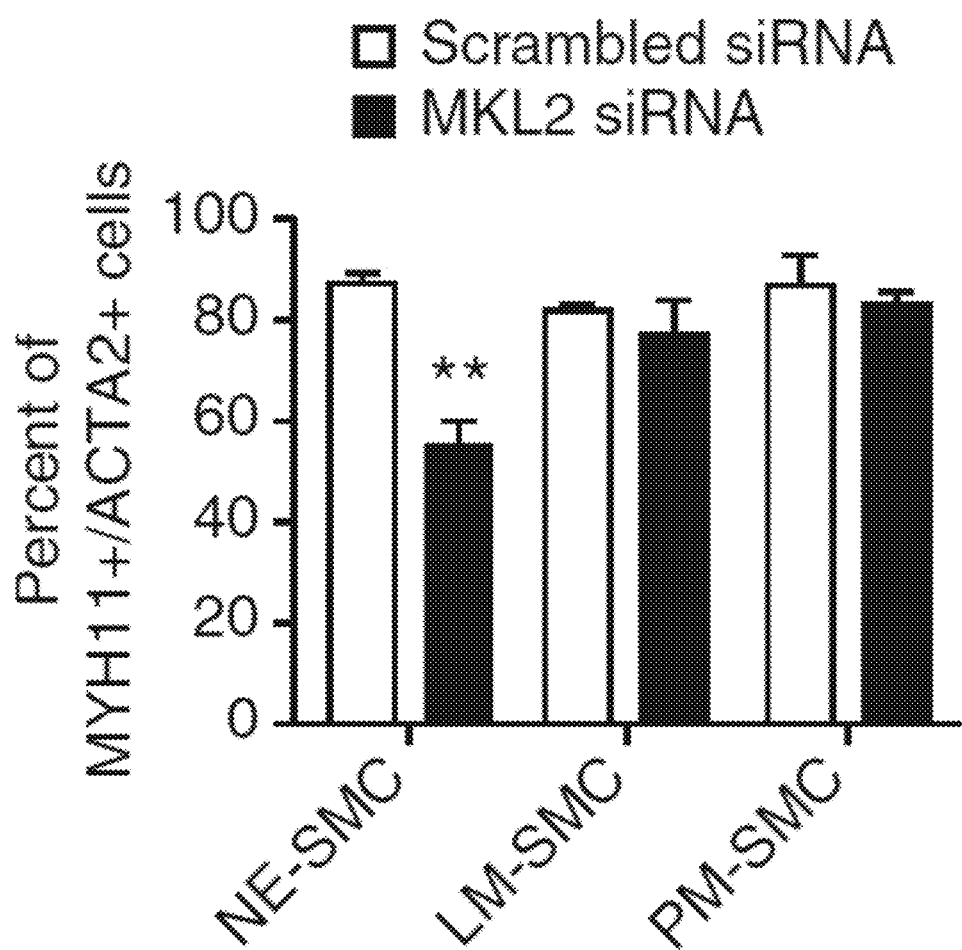

To determine whether our system reliably generated origin-specific SMCs from hPSCs, we validated our model against reported findings from developmental studies. MKL2 is a transcriptional co-activator for serum response factor that plays a role in early embryogenesis27. Previous in vivo studies revealed the unique requirement for Mkl2 during SMC differentiation from neural crest but not mesoderm. We postulated that MKL2 was essential only for NE-SMC specification and not for LM- or PM-SMC specification. To test this hypothesis, we silenced MKL2 using short interfering RNA (siRNA) in our intermediate populations (FIGS. 20 and 21). We then induced SMC differentiation and found that the MKL2 siRNA-treated cells showed a significant decrease in SMC gene expression in NE-SMCs (CNN1, P=0.0006; MYH11, P=0.015; SMTN, P=0.0023) compared to scrambled siRNA control, whereas LM-SMCs and PM-SMCs were unaffected (FIG. 22). Likewise, MKL2 knockdown resulted in a significant decrease in the percentage of MYH11+ACTA2+ NE-SMCs (55.0±4.8% MKL2 siRNA versus 86.7±2.1% scrambled control, P=0.0076, FIG. 23), but no reduction in SMCs derived from mesoderm origins.

Figure 24:
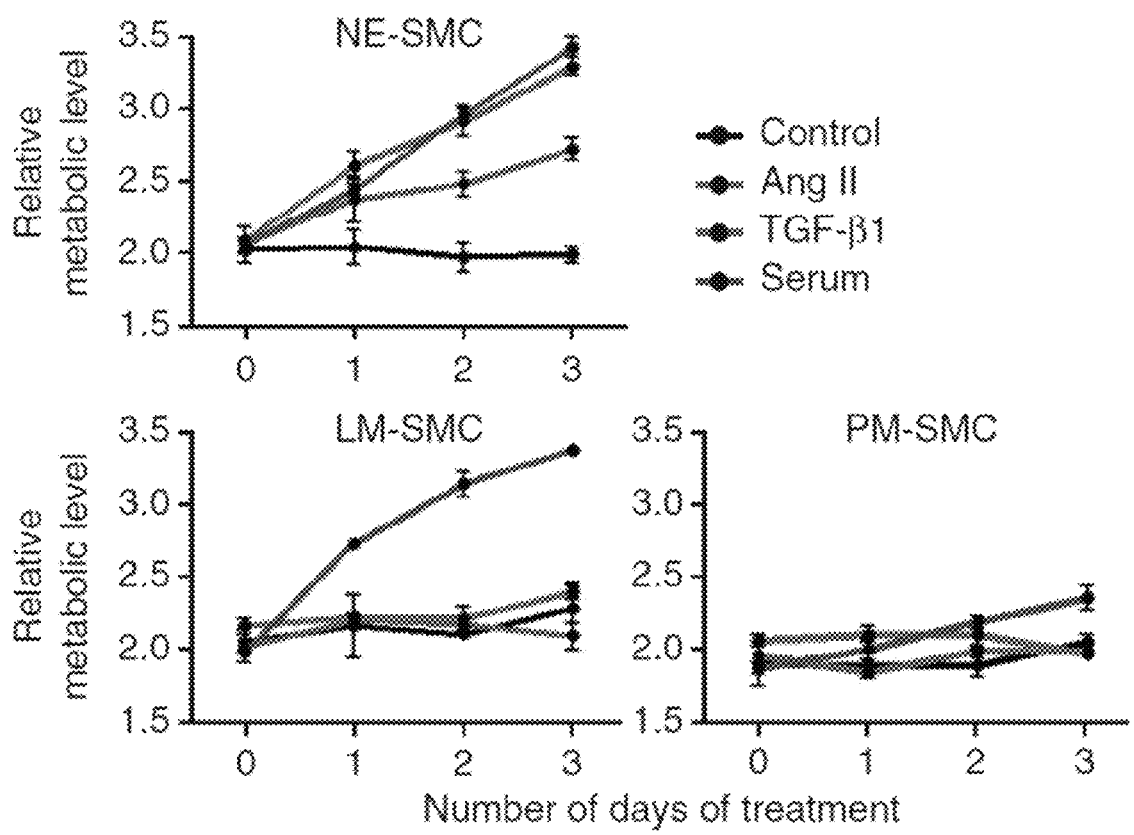
Figure 25A:
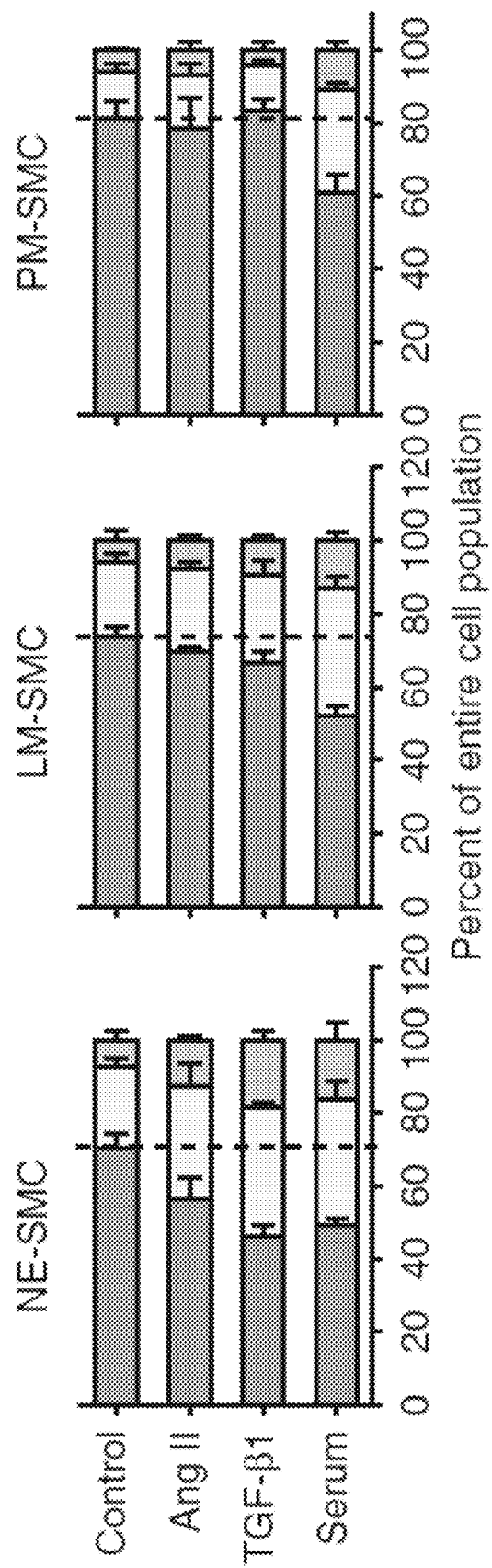
Figure 25B:
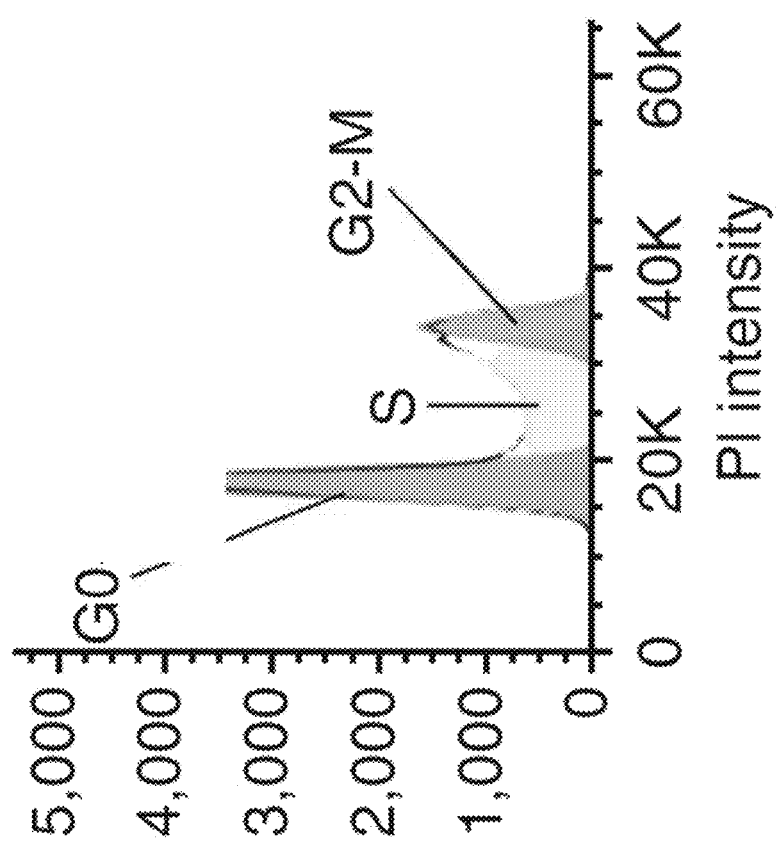

To confirm that we had generated origin-specific SMC subtypes, we used cytokines known to induce unique responses in aortic SMCs of distinct origins. Angiotensin II (Ang II) promotes medial hyperplasia in the ascending aorta (neuroectoderm derivative) but not the descending aorta (mesoderm derivative), TGF-β1 also encourages greater cell proliferation in SMCs of neuroectoderm origin compared to those of mesodermal origin. Consistent with the previous studies, NE-SMC proliferated in response to Ang II (1 μM, red lines) and TGF-β1 (5 ng/ml, green lines) over 3 d, but LM-SMC and PM-SMC did not (FIG. 24). Serum (10%, blue lines), a potent mitogen, induced proliferation in all the SMC subtypes although to a much lesser extent in PM-SMC. Cell cycle analysis confirmed that Ang II, TGF-β1 or serum each increased the proportion of NE-SMCs in S and G2-M phases compared to vehicle control after 24 h (FIGS. 25A and 25B). LM-SMC and PM-SMC showed higher S and G2-M populations only upon serum treatment.

Figure 26:
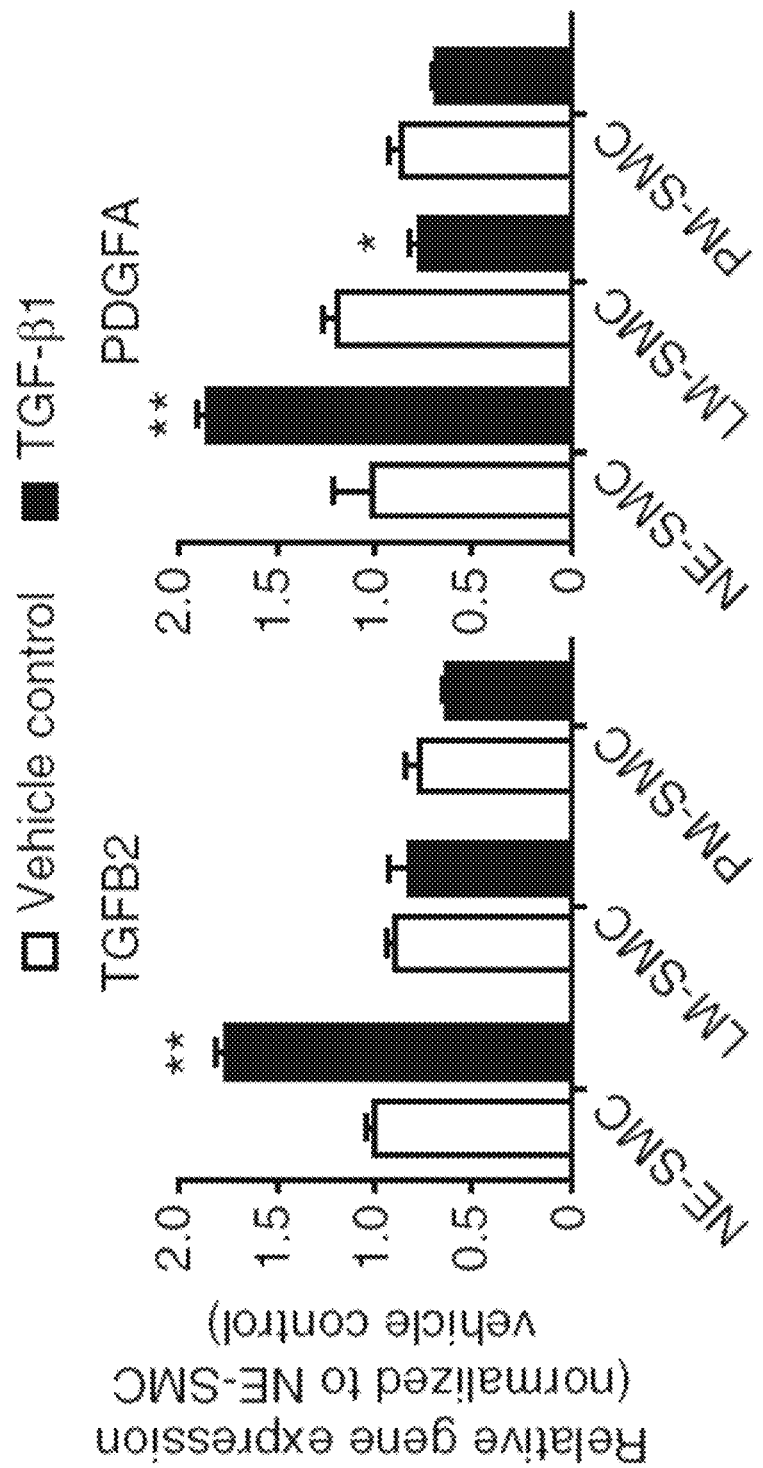
Figure 27:
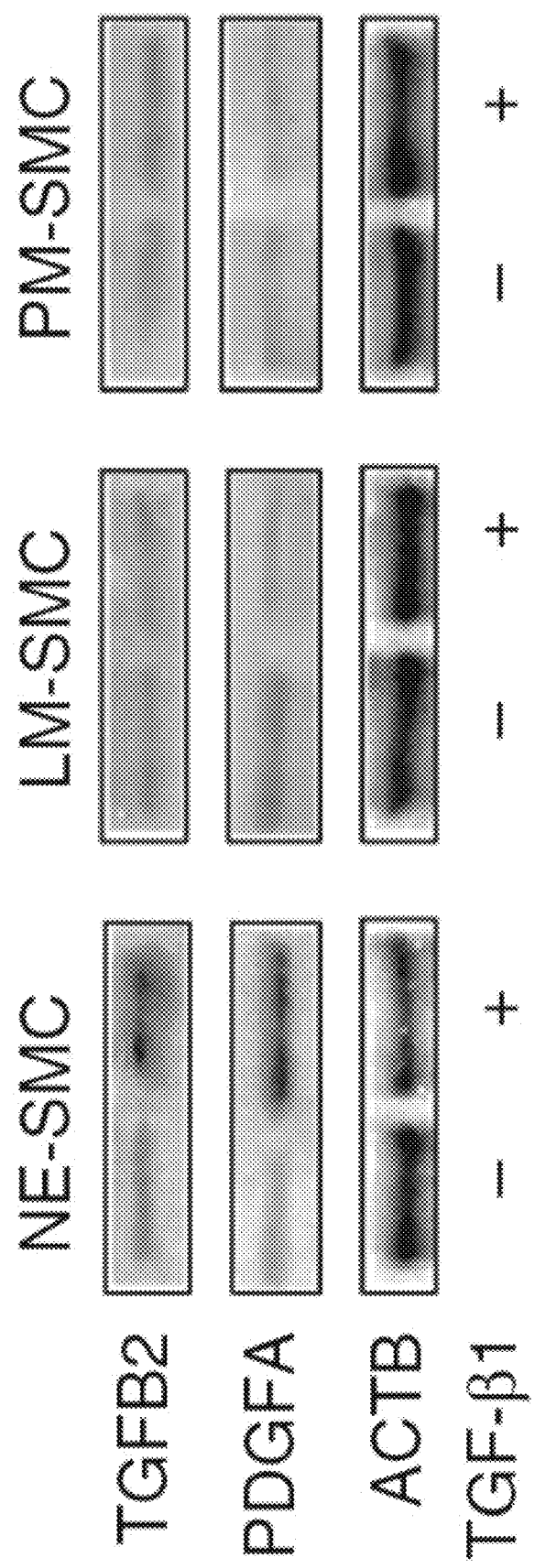
Figure 28A:
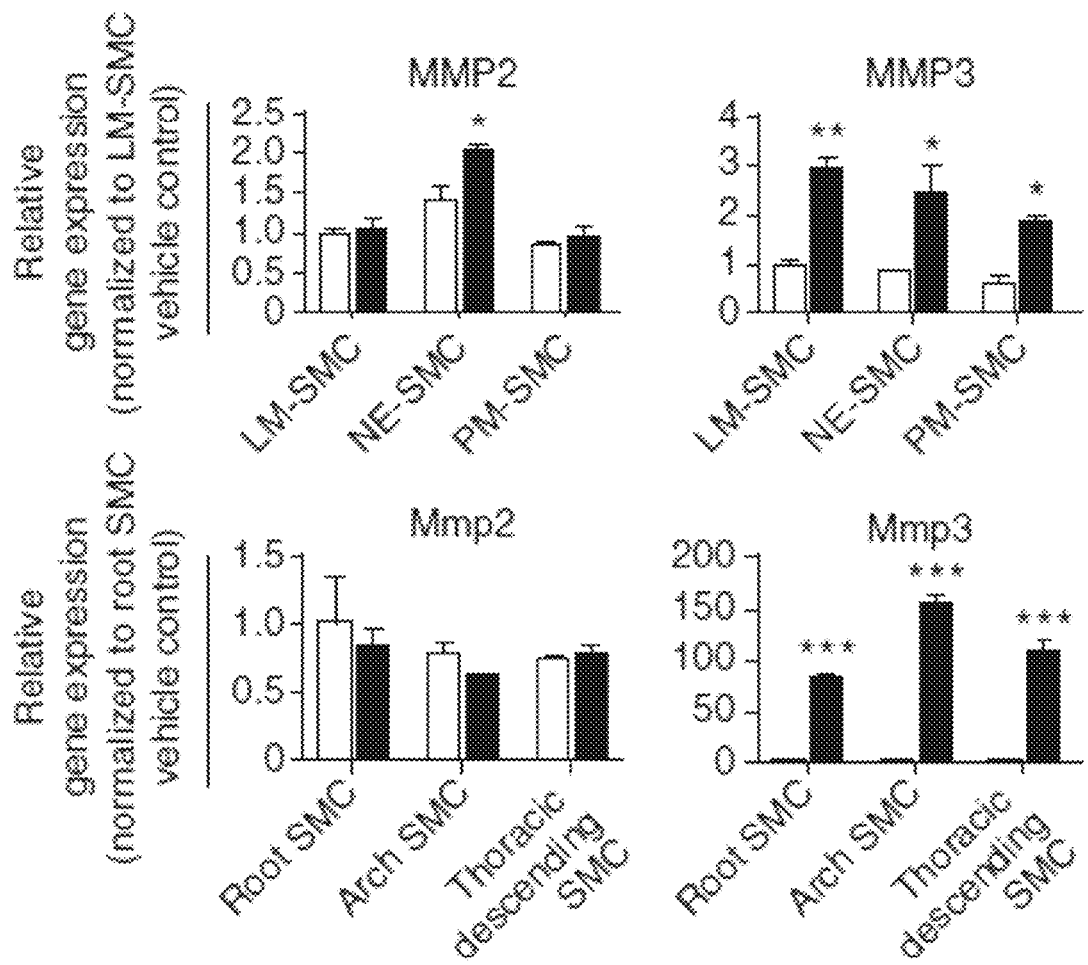
FIGS. 28A to 28C show Gene expression levels of MMPs (28A and 28B) and TIMPs (28C) in control and IL-1β-treated SMCs as determined by qRT-PCR after 6 h of treatment. Differential activation of MMP9 and TIMP1 expression was observed in both the hPSC-derived SMCs (top panels) and rat aortic SMCs (bottom panels).
Figure 28B:
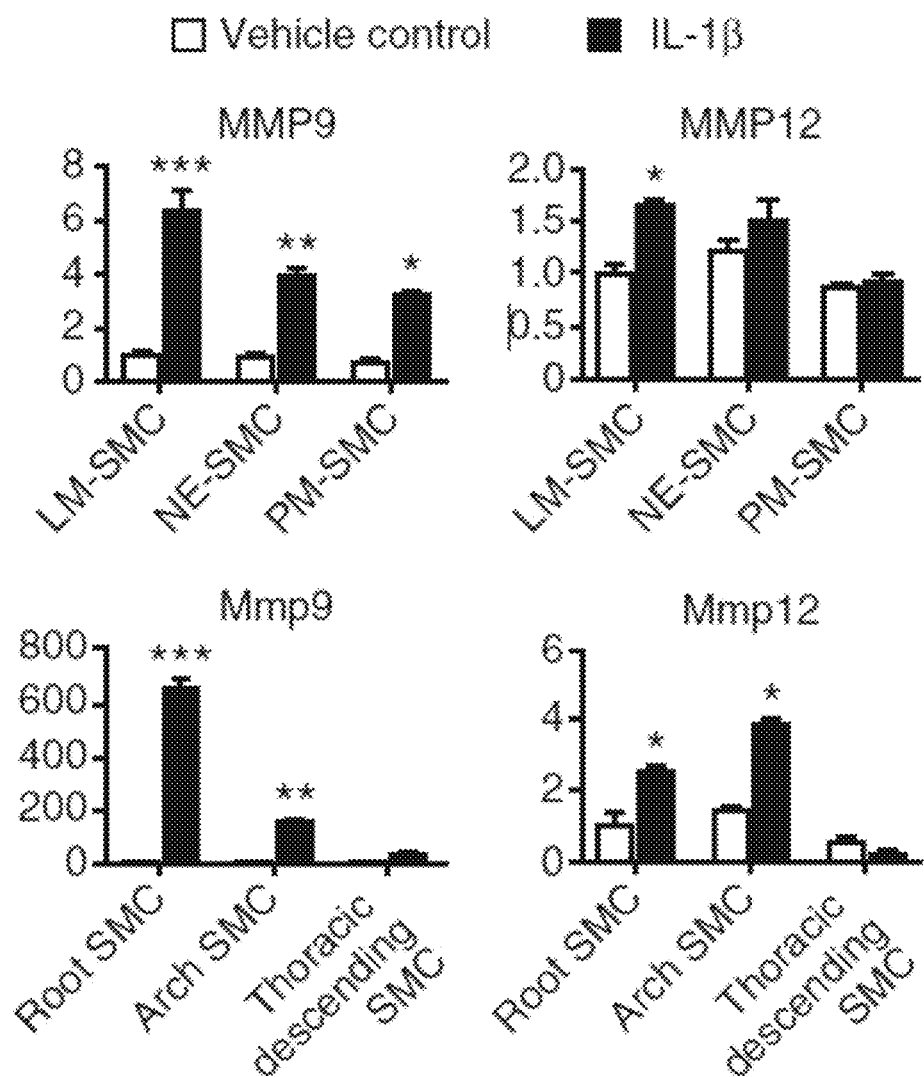
Figure 28C:
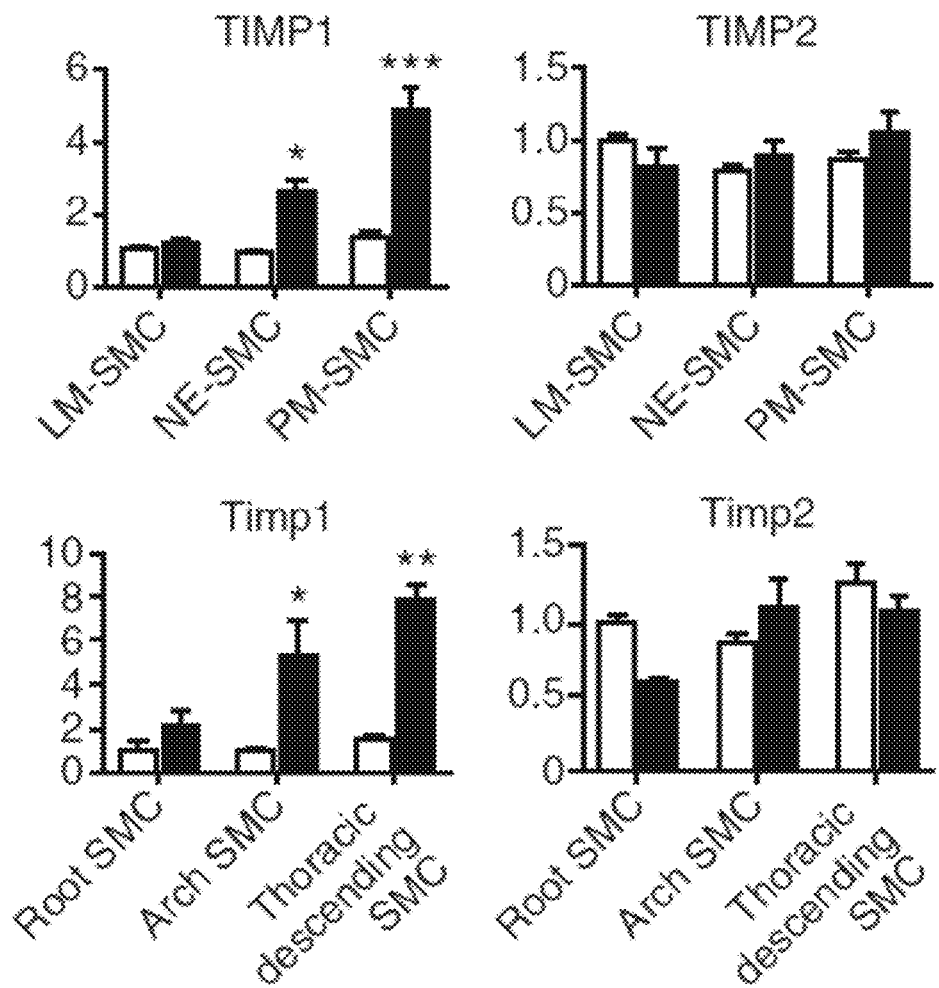
Figure 29:
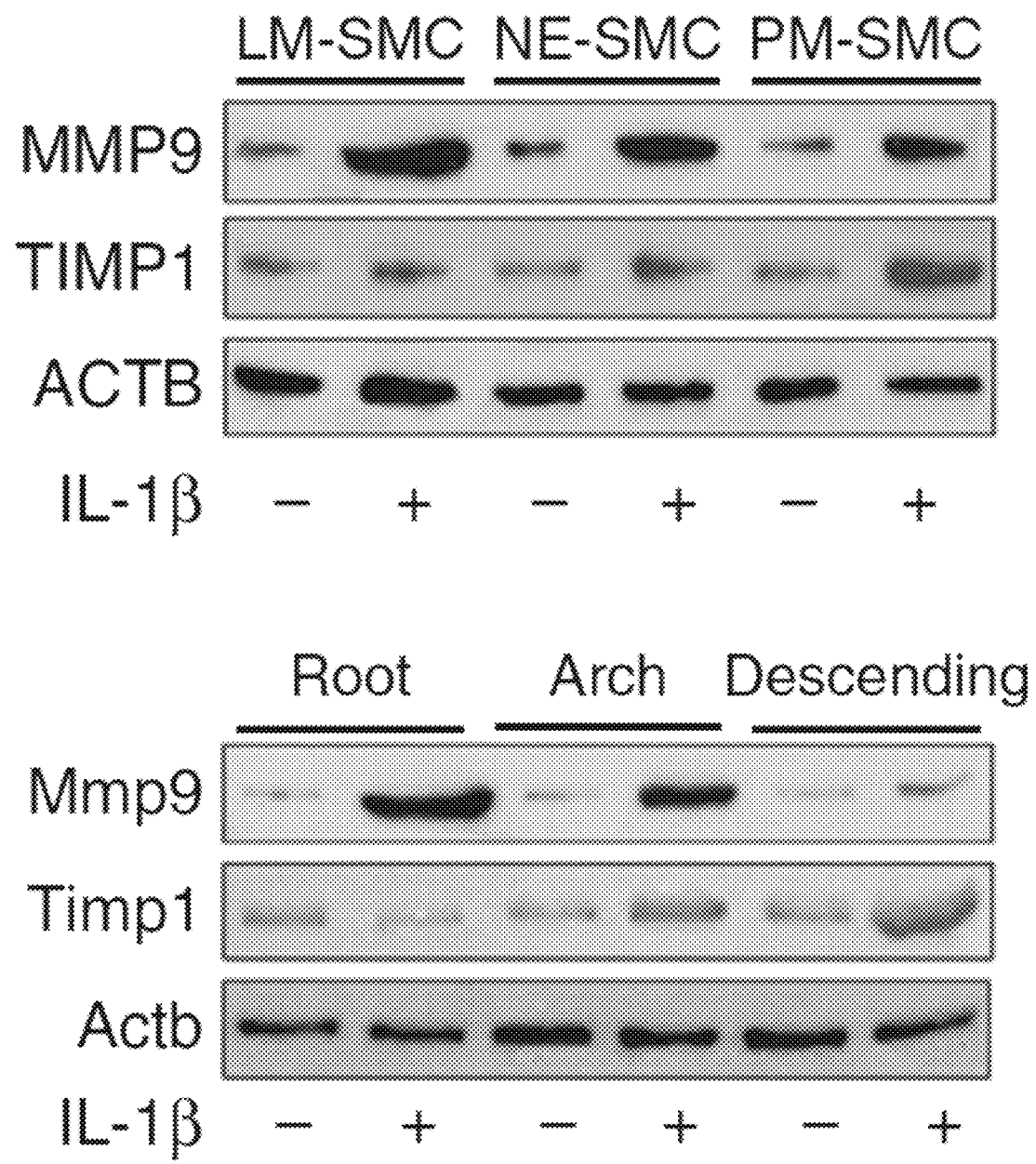
Figure 30:
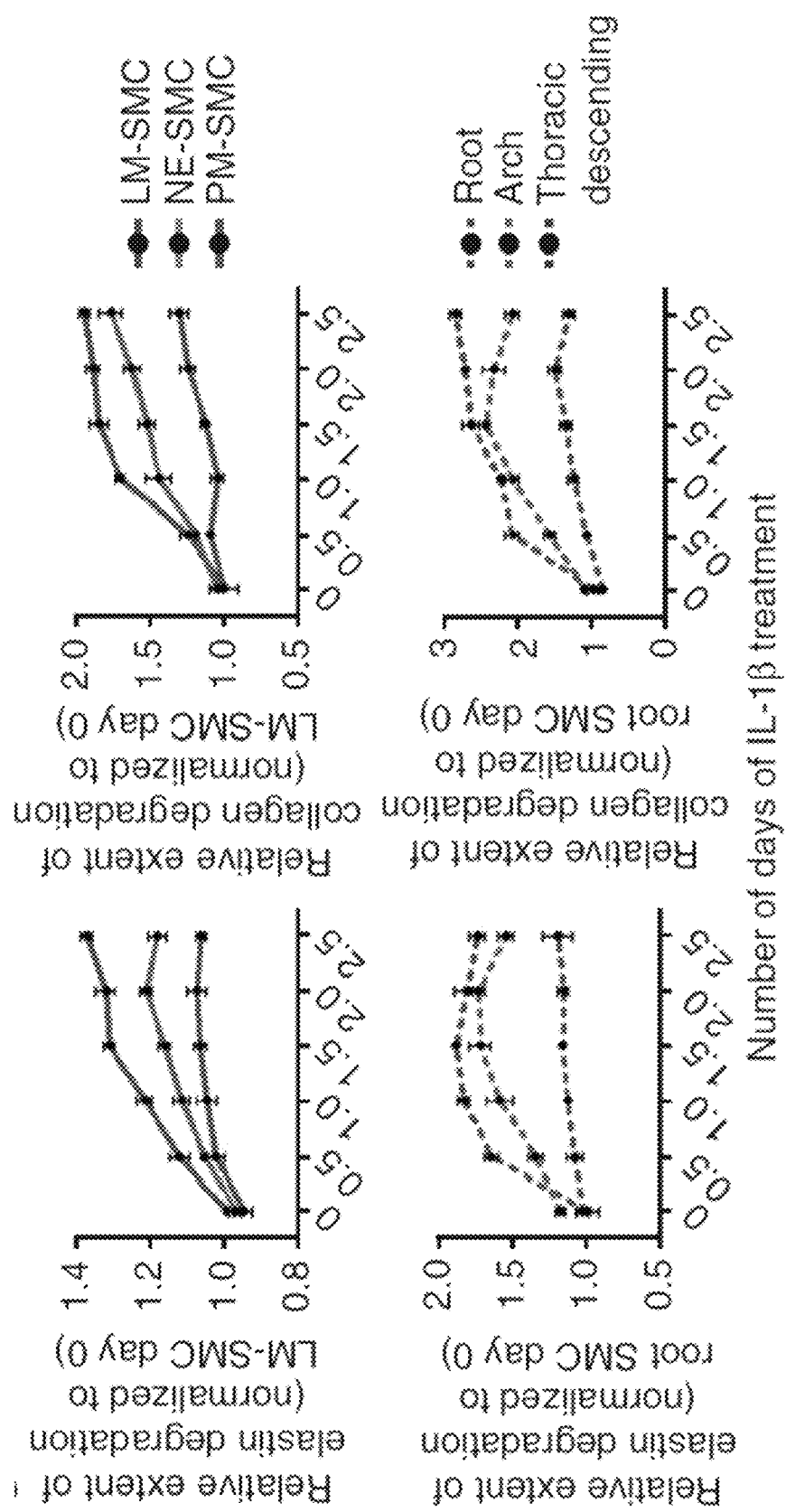

Only NE-SMCs proliferated in response to TGF-β1 (FIGS. 24, 25). TGF-β1 may have enhanced cell proliferation by autocrine production of TGF-β2 and PDGFA. We investigated whether TGF-β1 stimulated greater auto-induction of TGF-β2 and PDGFA in SMCs of a neuroectoderm origin. TGFB2 (P=0.002) and PDGFA (P=0.0015) expression was significantly upregulated only in NE-SMCs after 10 h of TGF-β1 (5 ng/ml) treatment compared with vehicle control (FIG. 26). Correspondingly, elevated TGFB2 and PDGFA protein levels were found in NE-SMC lysates after TGF-β1 treatment (FIG. 22). Taken together, the data on requirement for MKL2 and their unique proliferative and secretory responses validate the hypothesis that our different SMC subtypes are analogous to the distinct lineage-dependent SMC populations documented in vivo. To investigate a link between SMC developmental origins and susceptibility to vascular diseases, we treated our SMC subtypes with IL-1β (10 ng/ml), an atherogenic cytokine33. Rat SMCs isolated from various aortic regions were tested in parallel. A panel of MMP and TIMP markers, known to be implicated in human atherosclerosis and aneurysm formation34, was investigated. We discovered that, broadly, LM-SMCs, NE-SMCs and PM-SMCs modelled similar responses to IL-1β as the rat aortic SMCs (bottom panel) of corresponding origins-root, arch and thoracic descending (FIGS. 28A to 28C). In particular, MMP9 and TIMP1 expression levels were differentially activated in our SMC subtypes, as were rat SMCs of distinct origins. The induction of Mmp9 relative to control in the rat SMCs was ~100-fold greater than that in the hPSC-derived SMCs. This could be due to species-specific variations or different degrees of SMC maturity, either of which could reflect the differences in level of activation for certain genes. Western blot analysis confirmed that the hPSC-derived SMCs (top panel) could predict the differential levels of MMP9 and TIMP1 proteins in the rat aortic SMCs after exposure to the same stimulus (FIG. 29). The human SMC subtypes also predicted the differential elastin (left panel) and collagen (right panel) degradation demonstrated by the rat aortic SMCs (FIG. 30). In summary, these results provide indication that adult SMCs display heterogenous matrix remodeling responses due, in part, to their different origins. Notably, our in vitro-derived SMC subtypes are able to effectively model and predict the properties of their in vivo counterparts and consequently may have relevance in predicting origin-dependent disease responses.

Figure 31:
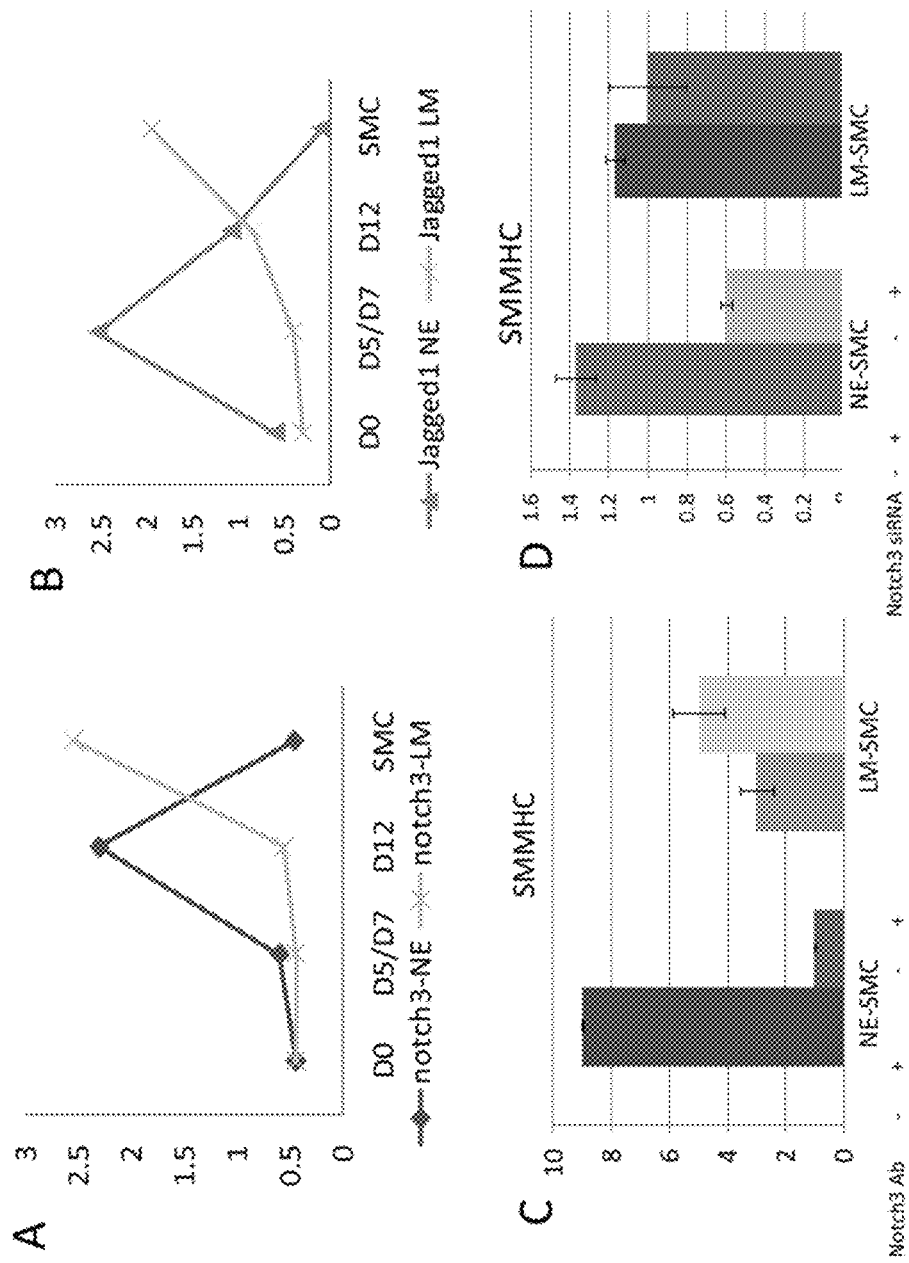
FIG. 31 shows the requirement for Notch3 signalling for NE-SMC differentiation. Panel A shows qRTPCR demonstrating differential expression of Notch3 and Panel B shows its ligand Jagged1, with early expression in NE-SMCs. Panels C and D show inhibition of Notch3 using a blocking or control antibody or Notch3 siRNA or scrambled control respectively.

Notch3 and its ligand Jagged were found to be differentially expressed in NE-SMCs and LM-SMCs, with early expression in NE-SMCs (FIGS. 31A and 31B). Inhibition of Notch-3 using an antibody or siRNA inhibited differentiation into NE-SMCs only (FIGS. 31C and 31D).

Figure 32:
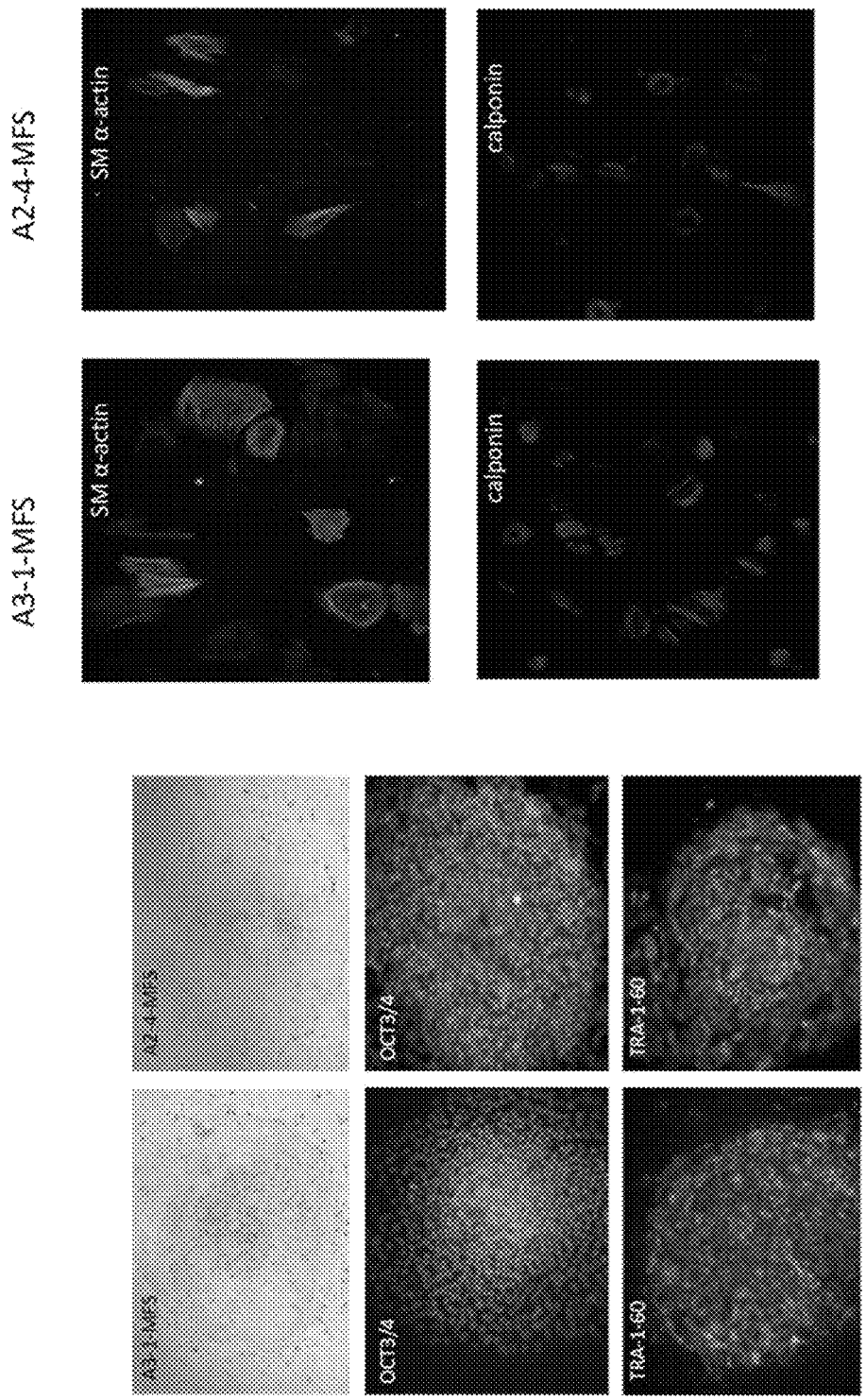
FIG. 32 shows SMCs Generated from Marfan Syndrome-derived Induced Pluripotent Stem (iPS) Cells. The LH panel shows staining for pluripotency markers Oct3/4 and Tra-1-60 in isolated iPS cell colonies derived from Marfan syndrome patient-derived fibroblasts transduced with retroviruses expressing Oct4, Sox2, KLF4 and c-Myc. The RH panel shows staining for the SMC markers, SM alpha-actin and calponin in SMCs generated from patient-derived iPS cells using the protocols described herein.

Marfan syndrome patient-derived fibroblasts were transduced with retroviruses expressing Oct4, Sox2. KLF4 and c-Myc. The reprogrammed iPS cell colonies were isolated and stained for the pluripotency markers Oct3/4 and Tra-1-60 (FIG. 32 LH panels). SMCs were generated from the patient-derived iPS cells using the protocols previously described in Cheung et al. Nature Biotech 2012, and stained for the SMC markers, SM alpha-actin and calponin (B). Origin specific SMCs were found to be generated from Marfan Syndrome-derived Induced Pluripotent Stem (iPS) Cells (FIG. 32 RH panel).

Figure 33:
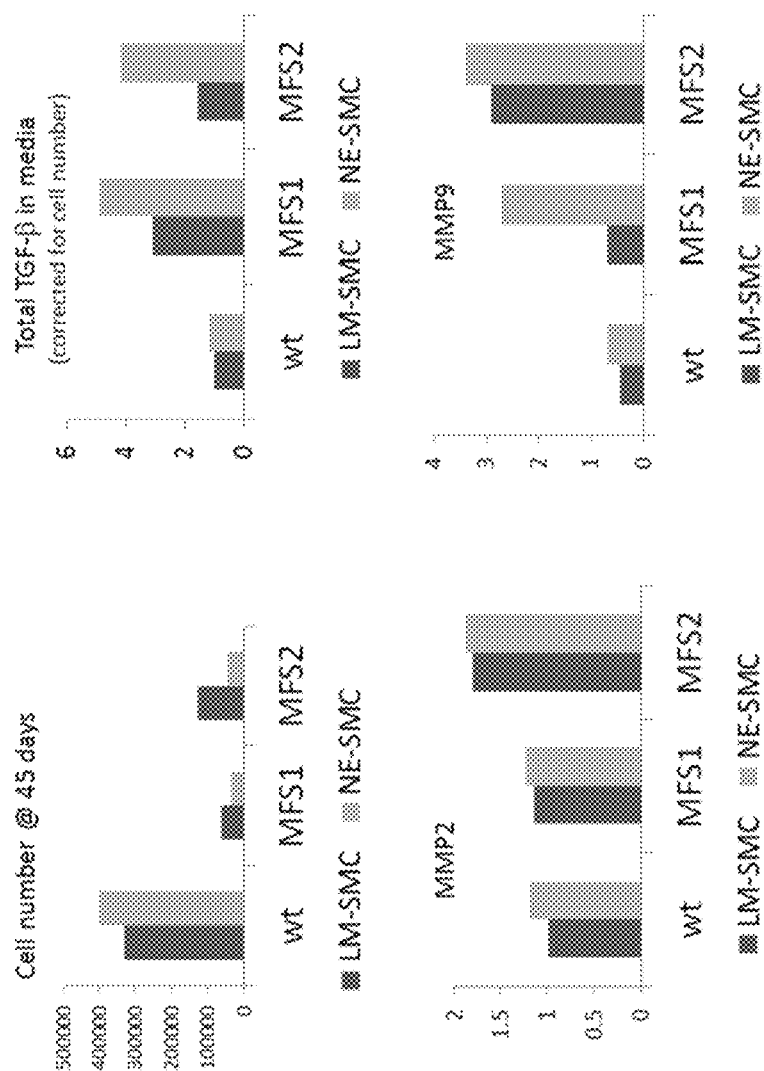
FIG. 33 shows cell numbers, TGF-β release and MMP2 and MMP9 expression compared to wild type controls in lateral plate mesoderm (LM-) or neuroectoderm (NE-) derived SMCs generated using iPS cells from Marfan patients and wild type controls.

Lateral plate mesoderm (LM-) or neuroectoderm (NE-) derived SMCs were generated using iPS cells from Marfan patients and wild type controls, as described above. SMC numbers were reduced in Marfan derived cultures while there was increased TGF-b release and MMP2 and MMP9 expression compared to wild type controls (FIG. 33). Abnormalities in cell numbers, TGF-β and MMPs were more pronounced in NE-SMCs than in LM-SMCs. These results provide indication that Marfan-derived SMCs preferentially display pathological in the neuroectoderm-derived lineage.

Figure 34:
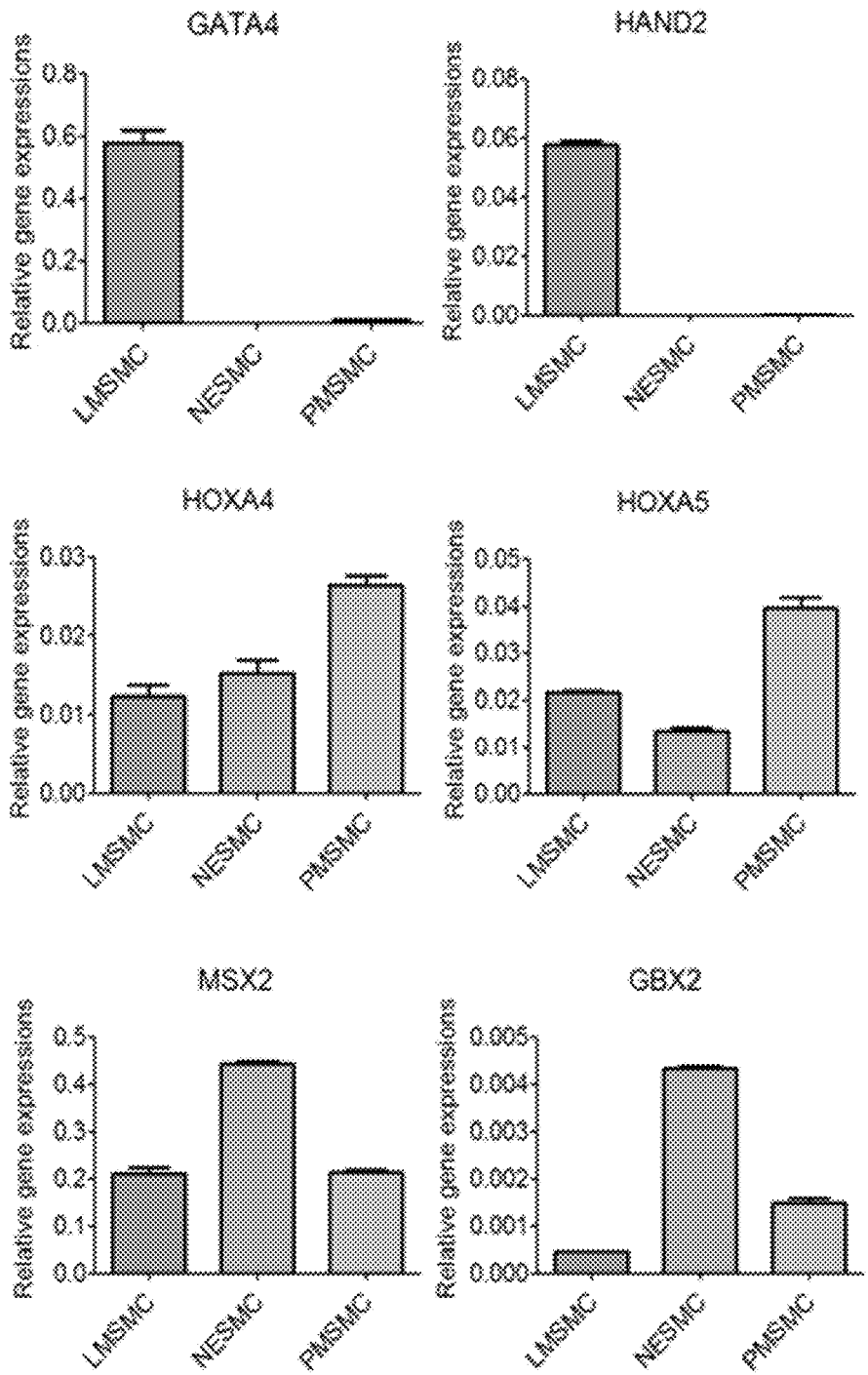
FIGS. 34 and 35 show that lineage specific SMCs have distinct transcriptional 'signatures'.
Figure 35:
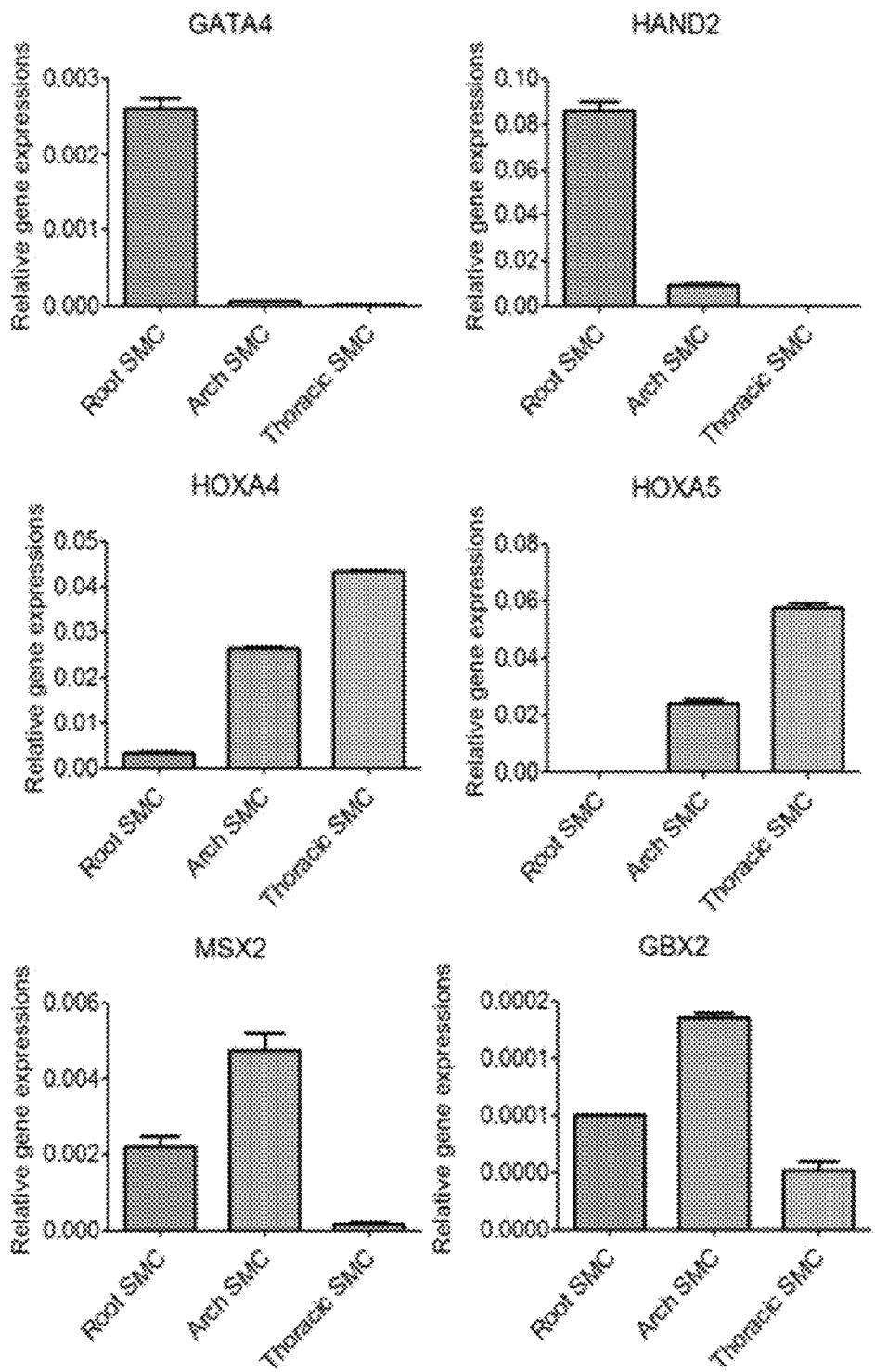

Human pluripotent stem cell-derived SMCs were assessed by RTQPCR for expression of selected genes. Distinct transcriptional signatures found in origin-specific SMC subtypes (FIG. 34. GATA4 and HAND2 were found to mark SMCs of lateral plate mesoderm origin; HOXA4 and HOXA5 mark SMCs of paraxial mesoderm origin; MSX2 and GBX2 mark SMCs of neuroectoderm origin. These transcriptional signatures were confirmed by similar expression profiles in human foetal aortic SMCs developed from corresponding origins (FIG. 35). Root SMCs originate from lateral plate mesoderm; arch SMCs originate from paraxial mesoderm; thoracic descending SMCs originate from neuroectoderm.

We have thoroughly evaluated the roles of various signalling factors (BMP4, FGF2, Activin A) and their inhibitors (Noggin or Dorsomorphin, SU5402 or UO126 or LY294002, and SB431542) at different concentrations and in chemical defined conditions. We have also determined the best time to add these various factors within a period of 5 days. In all, we discovered an efficient 36 h protocol to differentiate hESCs into early mesoderm, named FLyB from which by varying the amount of BMP4 and/or manipulating the PI3K pathway, we differentiated paraxial and lateral plate mesoderm. Differentiation of paraxial mesoderm can be induced by removal of BMP4 and blockage of the PI3K pathway. Differentiation of lateral plate mesoderm can be induced by increasing the levels of BMP4 as described above.

We have developed a chemically defined monolayer system to generate origin-specific vascular SMCs from hPSCs with high efficiency. Human ESCs and iPSCs were initially induced to form three populations of distinct developmental lineages, namely the lateral mesoderm, paraxial/somitic mesoderm and neuroectoderm, then followed by SMC differentiation of these intermediate populations. The derived SMCs were positive for smooth muscle markers and their functional properties were confirmed by calcium signalling and contraction in response to vasoconstrictors. Furthermore, our derived SMCs recapitulated the differential cell proliferation response to cytokines, such as interleukin-1β (IL-1β), as demonstrated in previous studies using cultured aortic SMCs of distinct origins.

The in vitro SMC differentiation system described herein defines conditions for generating SMCs from different embryological origins. Elucidating the molecular mechanisms underlying origin-dependent differences in SMC behaviour may provide clues to understanding how SMC origins influence a variety of vascular disease patterns. Furthermore, our ability to produce large amounts of SMC subtypes from hPSCs should be beneficial in far-reaching applications in vascular disease modelling and regenerative medicine. Genetic syndromes and hereditary influences seem to be closely linked to SMC dysfunction in the thoracic aorta. Congenital vascular diseases, such as cono-truncal defects or CADASIL, feature mutations that predominantly affect neural crest-derived SMCs. Disease modelling with the appropriate origin-specific SMCs generated from patient-derived iPSCs may therefore be useful for accurate assessment and therapeutic discovery. Patient-matched SMCs may also be used to construct bioengineered blood vessels for coronary and peripheral artery bypass or haemodialysis grafts. In tissue or whole-organ regeneration, optimal outcomes require adequate vascularization. Therefore, to maximize success in both disease modelling and regenerative medicine, it may be useful to focus on SMCs that are derived from the same embryonic lineage as in the affected tissue or organ. In conclusion, we have generated an in vitro system which has broad applications in modelling SMC heterogeneity; elucidating mechanisms of SMC related diseases, and vascular regenerative medicine.

REFERENCES

Cheung et al Nature Biotechnology (2012) 30 165-173
Ferreira L S et al Circ Res. 2007 Aug. 3; 101(3):286-94.
Goldman, D. C. et al (2009) Blood 114, 4393-4401.
Huang H, et al (2006) Biochemical and Biophysical Research Communications 351: 321-327.
Schneider, M. D. et al (2003). Cytokine Growth Factor Rev 14, 1-4.
Vallier L, et al J Cell Sci. 2005 Oct. 1; 118(Pt 19):4495-509.
Vallier, L. et al. (2009) PLoS One 4, e6082.
Vazao H, et al PLoS One. 2011 Mar. 10; 6(3):e17771.
Vo E, et al. Stem Cell Rev. 2010 June; 6(2):237-47.
Xie C Q et al (2007) Arteriosclerosis, Thrombosis, and Vascular Biology 27: e311-312.
Ku, R. H. et al (2002) Nat Biotechnol 20, 1261-1264.
Yang, L. et al (2008). Nature 453, 524-528.
Yook, J. Y. et al (2011) Stem Cells Dev 5, 5.
Yu, P. et al (2011). Cell Stem Cell 8, 326-334.
Zhang, P et al. (2008). Blood 111, 1933-1941.

The invention claimed is:

1. A method for producing a population of embryonic-lineage specific smooth muscle cells (SMCs) comprising;
   (i) providing a population of human pluripotent stem cells,
   (ii) culturing the population of human pluripotent stem cells in an early mesoderm induction medium to produce a population of early mesoderm cells,
   wherein the early mesoderm induction medium is a chemically defined medium (CDM) which has fibroblast growth factor activity, stimulates SMAD1, SMAD5 and SMAD9 mediated signalling pathways and inhibits phosphatidylinositol 3-kinase (PI3K) activity,
   (iii) either;
   a) culturing the population of early mesoderm cells in a lateral mesoderm induction medium to produce a population of lateral mesodermal progenitor cells,
   wherein the lateral mesoderm induction medium is a chemically defined medium (CDM) which has fibroblast growth factor activity and stimulates SMAD1, SMAD5 and SMAD9 mediated signalling pathways; or
   b) culturing the population of early mesoderm cells in a paraxial mesoderm induction medium to produce a population of paraxial mesodermal progenitor cells,
   wherein the paraxial mesoderm induction medium is a chemically defined medium (CDM) which has fibroblast growth factor activity and inhibits phosphatidylinositol 3-kinase (PI3K) activity, and;
   (iv) culturing the population of lateral or paraxial mesodermal progenitor cells in an SMC induction medium to produce a population of lateral or paraxial mesodermal SMCs of the embryonic lineage.

2. A method according to claim 1 wherein said early mesoderm induction medium consists of CDM supplemented with FGF, BMP and a phosphatidylinositol 3-kinase inhibitor.

3. A method according to claim 1 wherein the method comprises;
   (iii) culturing the population of early mesoderm cells in a lateral mesoderm induction medium to produce a population of lateral mesodermal progenitor cells,
   wherein the lateral mesoderm induction medium is a chemically defined medium (CDM) which has fibroblast growth factor activity and stimulates SMAD1, SMAD5 and SMAD9 mediated signalling pathways; and
   (iv) culturing the lateral mesodermal progenitor cells in the SMC induction medium to produce a population of lateral mesodermal SMCs.

4. A method according to claim 3 wherein said lateral mesoderm induction medium consists of CDM supplemented with FGF and BMP.

5. A method according to claim 3 wherein the early mesoderm cells are cultured in the lateral mesoderm induction medium for at least 2 days.

6. A method according to claim 1 wherein method comprises
   (iii) culturing the population of early mesoderm cells in a paraxial mesoderm induction medium to produce a population of paraxial mesodermal progenitor cells,
   wherein the paraxial mesoderm induction medium is a chemically defined medium (CDM) which has fibroblast growth factor activity and inhibits phosphatidylinositol 3-kinase (PI3K) activity; and
   (iv) culturing the paraxial mesodermal progenitor cells in the SMC induction medium to produce a population of paraxial mesodermal SMCs.

7. A method according to claim 6 wherein said paraxial mesoderm induction medium consists of CDM supplemented with FGF and an PI3K inhibitor.

8. A method according to claim 6 wherein the early mesoderm cells are cultured in the paraxial mesoderm induction medium for at least 2 days.

9. A method according to claim 1 wherein the SMC induction medium is a chemically defined medium (CDM) which has platelet derived growth (PDGF) factor activity and stimulates SMAD2 and SMAD3 mediated signalling pathways.

10. A method according to claim 9 wherein said SMC induction medium consists of CDM supplemented with PDGF and TGFβ1.

11. A method according to claim 1 comprising expanding, culturing, maintaining or storing the population of SMCs.

12. A method according to claim 1 wherein the human pluripotent stem cells are iPS cells.

13. A method according to claim 12 wherein the iPS cells are derived from cells obtained from an individual, optionally wherein the individual has a genetic disorder or condition characterised by or associated with diseased, damaged or dysfunctional vascular tissue or is in need of tissue vascularisation or re-vascularisation.

14. A population of isolated SMCs produced by a method according to claim 1.

15. A method of vascularising, re-vascularising or increasing the vascularisation of tissue or treating a patient with a damaged, diseased or dysfunctional vascular tissue comprising;
administering a population of SMCs according to claim 14 to an individual in need thereof.

16. A method for producing a population of embryonic-lineage specific smooth muscle cells (SMCs) comprising;
(i) providing a population of human pluripotent stem cells,
(ii) culturing the population of human pluripotent stem cells in a neuroectoderm induction medium to produce a population of neuroectodermal progenitor cells,
wherein the neuroectoderm induction medium is a chemically defined medium (CDM) which has fibroblast growth factor (FGF) activity and activin inhibition activity, and;
(iii) culturing the population of neuroectodermal progenitor cells in an SMC induction medium to produce a population of neuroectodermal SMCs.

17. A method according to claim 16 wherein said neuroectoderm induction medium consists of CDM supplemented with FGF and an activin antagonist.

18. A method according to claim 17 wherein the human pluripotent stem cells are cultured in the neuroectoderm induction medium for at least 3 days.

19. A method according to claim 16 wherein the progenitor cells are cultured in the SMC induction medium for at least 6 days.

* * * * *